(12) United States Patent
Zhu et al.

(10) Patent No.: US 7,459,450 B2
(45) Date of Patent: Dec. 2, 2008

(54) NEUROPEPTIDE RECEPTOR MODULATORS

(75) Inventors: Zhaoning Zhu, Plainsboro, NJ (US); Zhong-Yue Sun, Parlin, NJ (US); Yuanzan C. Ye, Edison, NJ (US); Deborra E. Mullins, New York, NY (US); Brian McKittrick, New Vernon, NJ (US); Andrew Stamford, Chatham, NJ (US); William J. Greenlee, Teaneck, NJ (US)

(73) Assignee: Schering Corporation, Kenilworth, NJ (US)

( * ) Notice: Subject to any disclaimer, the term of this patent is extended or adjusted under 35 U.S.C. 154(b) by 220 days.

(21) Appl. No.: 11/117,584

(22) Filed: Apr. 28, 2005

(65) Prior Publication Data

US 2006/0089351 A1    Apr. 27, 2006

Related U.S. Application Data

(60) Provisional application No. 60/566,845, filed on Apr. 30, 2004.

(51) Int. Cl.
*A61K 31/541* (2006.01)
*C07D 417/02* (2006.01)

(52) U.S. Cl. .................. 514/226.8; 544/53; 544/55

(58) Field of Classification Search ............... 544/53, 544/55; 514/226.8
See application file for complete search history.

(56) References Cited

FOREIGN PATENT DOCUMENTS

JP        10101658 A   *   4/1998

* cited by examiner

*Primary Examiner*—Kahsay T Habte
(74) *Attorney, Agent, or Firm*—Palaiyur S. Kalyanaraman; William Y. Lee

(57) ABSTRACT

The present invention discloses compounds, which are novel receptor antagonists for NPY Y1 as well as methods for preparing such compounds. In another embodiment, the invention discloses pharmaceutical compositions comprising such NPY Y1 receptor antagonists as well as methods of using them to treat obesity, metabolic disorders, eating disorders such as hyperphagia, and diabetes. The compounds are represented by the structural Formula 1,

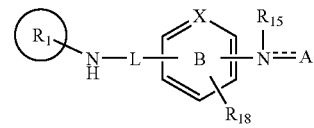

Formula 1 a prodrug thereof, or any pharmaceutically acceptable salt, solvate, isomer or racemic mixture of the compound or said prodrug wherein $R_1$ is heteroaryl, N-arylaminocarbonyl, N-heteroarylaminocarbonyl, benzimidazolyl or benzothiazolyl;

$R_{15}$ is present or not and if present is H, aryl, alkyl, arylalky or heteroarylalkyl;

A is aryl, heteroaryl, cycloalkyl, cycloalkylidene, heterocycloalkylidene or heterocycloalkyl wherein said aryl, heteroaryl, cycloalkyl, cycloalkylidene, heterocycloalkylidene and heterocycloalkyl moieties may be substituted or unsubstituted; and B, L, X and $R_{18}$ are defined herein.

29 Claims, No Drawings

NEUROPEPTIDE RECEPTOR MODULATORS

This application claims the benefit of priority of U.S. Ser. No. 60/566,845, filed Apr. 30, 2004.

FIELD OF THE INVENTION

The present invention relates to neuropeptide Y Y1 receptor antagonists which are particularly useful in the treatment of metabolic and eating disorders, pharmaceutical compositions containing the compounds, and methods of treatment using the compounds.

BACKGROUND OF THE INVENTION

Neuropeptide Y (NPY) is a 36 amino acid neuropeptide that is widely distributed in the central and peripheral nervous systems. NPY is a member of the pancreatic polypeptide family that also includes peptide YY and pancreatic polypeptide (Wahlestedt, C., and Reis, D., Ann. Rev. Toxicol., 32, 309, 1993). NPY elicits its physiological effects by activation of at least six receptor subtypes designated Y1, Y2, Y3, Y4, Y5 and Y6 (Gehlert, D., Proc. Soc. Exp. Biol. Med., 218, 7, 1998; Michel, M. et al., Pharmacol. Rev., 50, 143, 1998). Central administration of NPY to animals causes dramatically increased food intake and decreased energy expenditure (Stanley, B. and Leibowitz, S., Proc. Natl. Acad. Sci. USA 82: 3940, 1985; Billington et al., Am J. Physiol., 260, R321, 1991). These effects are believed to be mediated at least in part by activation of the NPY Y1 receptor subtype.

In addition to the treatment of metabolic and eating disorders, NPY Y1 receptor antagonists have potential therapeutic utility in the areas of pain, sexual dysfunction, congestive heart failure, cerebral hemorrhage, anxiety, depression, epileptic seizures, sleep disorders, migraine and allergic rhinitis. Thus, NPY Y1 and its regulatory pathways make compelling targets for a wide range of therapies and particularly in the development of obesity therapies.

Substituted phenyl compounds having activity against formation of nitrogen monoxide (NO) have been reported in Japanese Kokai Patent Application No. Hei 10[1998]-101658. Disclosed are compounds having the formula:

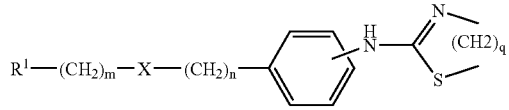

where the various elements are defined therein. An illustrative compound of that series is:

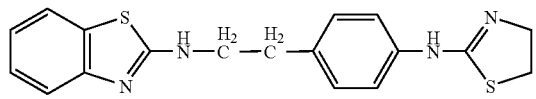

SUMMARY OF THE INVENTION

In its many embodiments, the invention provides a novel class of NPY Y1 antagonists, methods of preparing such compounds, pharmaceutical compositions comprising one or more such compounds, methods of preparing pharmaceutical formulations comprising one or more such compounds and methods of treatment, prevention, inhibition or amelioration of one or more diseases associated with the NPY pathway using the compounds and compositions of the invention.

In one embodiment, this invention provides novel compounds having NPY Y1 receptor antagonist activity, prodrugs thereof or pharmaceutically acceptable salts or solvates of the compounds. These compounds are represented in part by structural Formula 1:

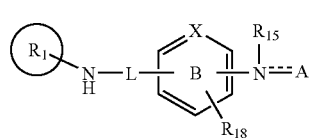

Formula 1 or a pharmaceutically acceptable salt or solvate thereof, wherein:

$R_1$ is heteroaryl, N-arylaminocarbonyl, N-heteroarylaminocarbonyl, benzimidazolyl or benzothiazolyl, and wherein the benzimidazolyl and benzothiazolyl are each optionally independently unsubstituted or substituted with 1 to 5 substituents and each substituent is independently selected from the group consisting of: halogen, alkyl, cycloalkyl, alkoxy, alkylsulfonyl, thio, alkoxyalkyl, cycloalkylalkyl, heterocycloalkyl, heterocycloalkylalkyl, arylalkyl, heteroarylalkyl, aryl, heteroaryl, —$OR_{20}$, —CN, —$NO_2$, —$NR_{20}R_{21}$, —$C(O)R_{20}$, —$C(O)OR_{20}$, —$C(O)NR_{20}R_{21}$, —$S(O)_{0-2}$ $NR_{20}R_{21}$, —$CF_3$, —$OCF_3$, —$CF_2CF_3$, —$C(=N-OR_{20})$ $R_{21}$, —$N(R_{20})S(O)_{0-2}R_{21}$, —$N(R_{20})C(O)(R_{21})$, —$N(R_{20})C$ $(O)NR_{21}R_{22}$, —$C(O)N(R_{20})(R_{21})$, —$SO_2R_{20}$ and —$SO_2N$ $(R_{20})(R_{21})$;

$R_{20}$, $R_{21}$ and $R_{22}$ are independently alkyl, cycloalkyl, heterocycloalkyl, cycloalkylalkyl, hetercycloalkylalkyl, arylalkyl, heteroarylalkyl, aryl or heteroaryl, wherein each alkyl, cycloalkyl, cycloalkylalkyl, hetercycloalkylalkyl, arylalkyl, heteroarylalkyl, aryl and heteroaryl are unsubstituted or optionally independently substituted with 1-5 substituents which are the same or different and are independently selected from the group consisting of: halogen, —$CF_3$, —CN, —COOH, —C(O)Oalkyl, —C(O)Ocycloalkyl, —C(O)O-arylalkyl, —C(O)O-heteroarylalkyl, —C(O)$NH_2$, —C(O)N (H)(alkyl), —C(O)N(H)(arylalkyl), —C(O)N(H)(heteroarylalkyl), —C(O)N(H)(cycloalkyl), —C(O)N(H)(aryl), —C(O)N(H)(heteroaryl), —C(O)N(H)(arylalkyl), —C(O)N (H)(heteroarylalkyl), —C(O)N(alkyl)(alkyl), —C(O)N (alkyl)(aryl), —C(O)N(alkyl)(heteroaryl), —S-alkyl, —S-aryl, —S-arylalkyl, —S-heteroarylalkyl, —$S(O)_2$ (alkyl), —$S(O)_2$(aryl), —$S(O)_2$(arylalkyl), —$S(O)_2$(heteroaryl), —$S(O)_2$(heteroarylalkyl), —$S(O)_2$(cycloalkyl), —$S(O)_2N(H)$(heterocycloalkyl), —$S(O)NH_2$, —S(O)N (alkyl)(alkyl), —S(O)N(H)(alkyl), —S(O)N(H)(aryl), —S(O)N(alkyl)(alkyl), —$S(O)_2NH_2$, —$S(O)_2N(H)$(alkyl), —$S(O)_2N(H)$(aryl), —$S(O)_2N(H)$(arylalkyl), —$S(O)_2N(H)$ (heteroarylalkyl), —$S(O)_2N(H)$(cycloalkyl), —$S(O)_2N$ (alkyl)(aryl), —$S(O)_2N$(alkyl)(alkyl), OH, —O($C_1$-$C_6$)alkyl, —O-cycloalkyl, —O-heterocycloalkyl, —O-Cycloalkylalkyl, —O-heterocycloalkylalkyl, —O-arylalkyl, —O-heteroarylalkyl, —O-Aryl, —O-heteroaryl, —$NH_2$, —N(H) (alkyl), —N(H)(aryl), —N(H)(heteroaryl), —N(H)arylalkyl, —N(H)(heteroarylalkyl), —N(alkyl)(alkyl), —N(arylalkyl) (arylalkyl), —N(heteroarylalkyl)(arylalkyl), —N(H)C(O)-alkyl, —N(H)C(O)-arylalkyl, —N(H)C(O)-heteroarylalkyl, —N(H)C(O)-heteroaryl, —N(H)C(O)-aryl, —N(H)C(O) $NH_2$, —N(H)C(O)N(H)(alkyl), —N(H)C(O)N(alkyl)(alkyl), —N(alkyl)C(O)N(H)(alkyl), —N(alkyl)C(O)N(alkyl)(alkyl), —N(H)S(O)₂-alkyl, —N(H)S(O)₂-arylalkyl, —N(H)S(O)₂-heteroarylalkyl, —N(H)S(O)₂-aryl, —N(H)S(O)₂-heteroaryl, —N(H)S(O)₂N(H)(alkyl), —N(H)S(O)₂N(alkyl)(alkyl), —N(alkyl)S(O)₂N(H)(alkyl) and —N(alkyl)S(O)₂N(alkyl)(alkyl);

X is —CH or N;

L is an aliphatic or heteroaliphatic linker chain optionally independently linked with one or more selected from the group consisting of: alkyl, aryl, cycloalkyl, spiroalkyl, heteroaryl and combinations thereof;

$R_{15}$ is present or absent and if present is H, aryl, alkyl, arylalkyl, heterocycloalkyl or heteroarylalkyl;

$R_{18}$ is H, halogen, alkyl, cycloalkyl, cycloalkylalkyl, heterocycloalkyl, heterocycloalkylalkyl, arylalkyl, heteroarylalkyl, aryl, heteroaryl, —OR$_{20}$, —CN, —NO$_2$, —NR$_{20}$R$_{21}$, —C(O)R$_{20}$, —C(O)OR$_{20}$, —C(O)NR$_{20}$R$_{21}$, —S(O)$_{0-2}$NR$_{20}$R$_{21}$, —CF$_3$, —OCF$_3$, —CF$_2$CF$_3$, —C(=N—OR$_{20}$)R$_{21}$, —N(R$_{20}$)S(O)$_{0-2}$R$_{21}$, —N(R$_{20}$)C(O)(R$_{21}$), —N(R$_{20}$)C(O)NR$_{21}$R$_{22}$, —C(O)N(R$_{20}$)(R$_{21}$), —SO$_2$R$_{20}$ or SO$_2$N(R$_{20}$)(R$_{21}$);

A is represented by the structural Formula 2:

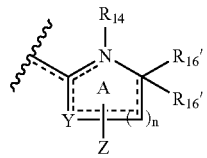

Formula 2

$R_{14}$ is present or absent and if present is H, aryl, alkyl, arylalkyl, carboxyl, alkylaryl, acyl, alkenyl, heteroarylalkyl, alkoxycarbonyl, heteroaryl, cycloalkyl, alkenyl or arylcarbonyl;

or $R_{14}$ taken together with $R_{16}$ or $R_{16'}$ is heteroaryl, heterocycloalkyl, heterocycloalkenyl, heterocyclenyl, heteroarylcycloalkenyl, heteroarylalkyl, heteroarylalkenyl, heterocycloalkenylaryl, heterocycloalkylaryl, heteroarylcycloalkyl, cycloalkylheteroaryl or heterocycloalkylheteroaryl;

$R_{16}$ and $R_{16'}$ are independently present or absent, are the same or different and are independently selected from the group consisting of: H, aryl, alkyl, arylalkyl, heteroaryl, carboxyl, substituted carboxyl, aroyl, heteroarylalkyl, cyclohexanyl, cycloalkyl, alkylthio, alkoxycarbonyl, cycloalkylalkyl, alkylaminocarbonyl, haloaryl, haloalkyl, phenylalkyl, alkoxy, acyl, aroyl, alkylcarboxyl, alkylcycloalkyl, alkylamino, adamantyl, alkylthioether, biphenyl, alkanol, dialkylisocyanate and alkylimidiazole, with the proviso that at least one of $R_{16}$ and $R_{16'}$ is present;

or $R_{16}$ and $R_{16'}$ taken together forms a spiroalkyl group, heterospiroalkyl group or =O;

Y is S, O, N or C with the proviso that (1) when Y is N, N is unsubstituted or substituted with alkyl, arylalkyl, heteroarylalkyl, alkenyk, arylcarbonyl, alkoxycarbonyl or a substituent selected from the group consisting of:

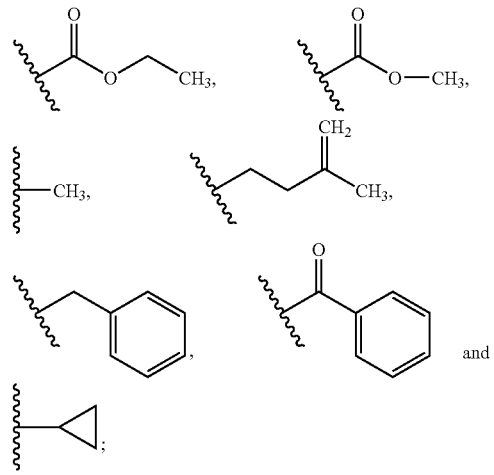

or (2) when Y is N, the substituents of N taken together with Z form a heterocycloalkyl moiety, or (3) when Y is C, C is unsubstituted, or optionally independently substituted with one or two substituents which are the same or different and are independently selected from the group consisting of: alkyl, arylalkyl, heteroarylalkyl, aryl and heteroaryl;

Z is either present or absent and if present is H, aryl, alkyl, alkoxy, arylalkyl, phenylalkyl, cycloalkyl, spiroalkyl, alkylaryl, alkylaminocarbonyl, haloaryl, haloalkyl, (CH$_3$)$_2$NC(O)—, alkylcarboxyl, acyl, heteroarylalkyl, alkoxycarbonyl, carboxyl, alkylcycloalkyl, alkylamino, alkylthioether, biphenyl, alkanol, dialkylisocyanate, alkylimidiazole or =O;

or

Z taken together with $R_{16}$ is aryl, heteroaryl, cycloalkyl, cycloalkenyl, heterocyclenyl, heterocycloalkyl, arylcycloalkenyl, heteroarylalkyl, heteroarylalkenyl, cycloalkenylaryl, arylcycloalkyl, cycloalkylaryl, heteroarylcycloalkyl or cycloalkylheteroaryl;

or

Z linked together with Y is heterocycloalkyl;

B is a six membered ring;

and n is 1, 2 or 3;

with the proviso that when either condition (i) or condition (ii) is satisfied, then at least one of $R_{16}$, $R_{16'}$, $R_{18}$ and Z is present and is a substituent other than H;

condition (i) is satisfied when the compound of Formula 1 is

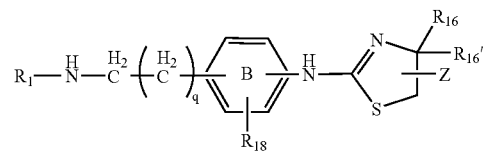

wherein $R_1$ is selected from the following structures:

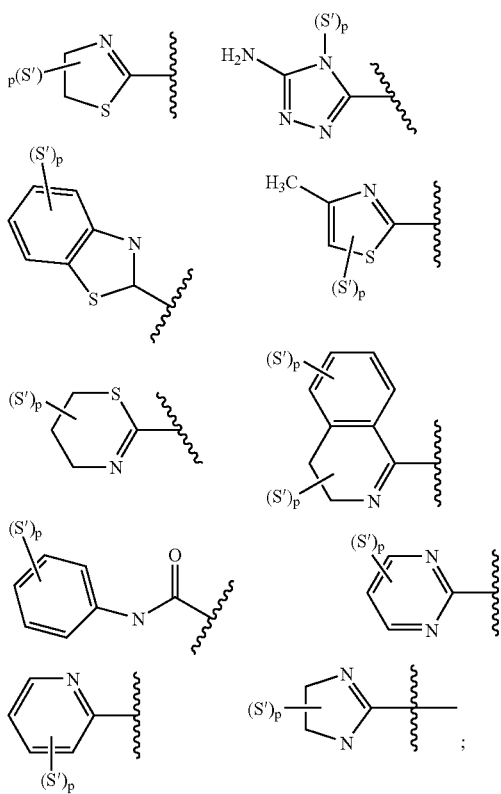

q is 1 or 2;
p is an integer from 1 to 5; and
S' is independently selected from the group consisting of: H, alkyl, halogen, methoxy, carboxyaminomethyl, alkoxycarbonyl and alkanoylaminomethyl;
condition (ii) is satisfied when the compound of Formula 1 is

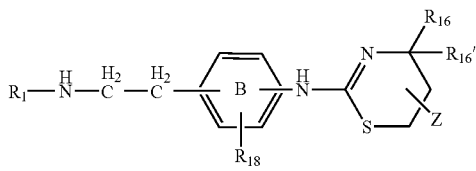

wherein $R_1$ is optionally substituted or unsubstituted and selected from the following structures:

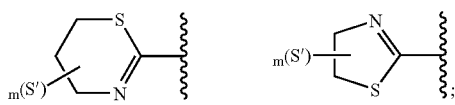

m is an integer from 1 to 5;

and

S' is independently selected from the group consisting of: H, alkyl, halogen, methoxy, carboxyaminomethyl, alkoxy, carbonyl and alkanoylaminomethyl.

A further feature of the invention is a pharmaceutical composition containing as active ingredient at least one compound of Formula 1 together with at least one pharmaceutically acceptable carrier or excipient.

The invention also provides methods for preparing compounds of Formula 1, as well as methods of treatment, prevention, inhibition or amelioration of one or more diseases associated with the NPY pathway. The methods for treating comprise administering to a patient suffering from a disease or diseases associated with the NPY pathway a therapeutically effective amount of at least one compound of Formula 1, or a pharmaceutical composition comprising at least one compound of Formula 1.

Also disclosed is the use of a compound of Formula 1 for the manufacture of a medicament for treating one or more diseases associated with the NPY pathway Also disclosed is a method of treatment of one or more diseases associated with the NPY pathway, comprising administering an effective amount of one or more of the inventive compounds.

Also disclosed is a method of treating, preventing, or ameliorating one or more symptoms of hepatitis C, comprising administering an effective amount of one or more of the inventive compounds.

DETAILED DESCRIPTION

The present invention relates to compounds represented by structural Formula 1, a prodrug or a pharmaceutically acceptable salt or solvate thereof, wherein the various moieties are as described above.

The compounds of Formula 1 can be administered as racemic mixtures or enantiomerically pure compounds.

In an embodiment of the compounds of formula 1, A is selected from the group consisting of:

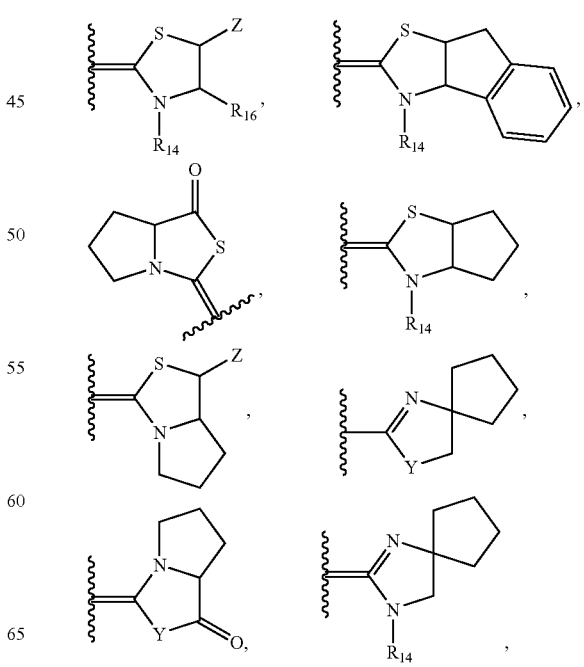

-continued
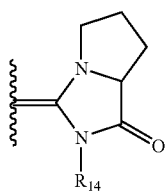 and 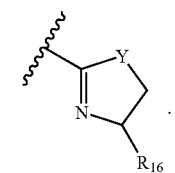.
In another embodiment, $R_{14}$ is present or absent and if present is selected from the group consisting of: H,
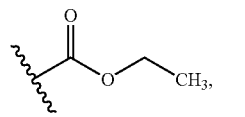 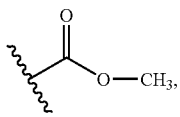,
 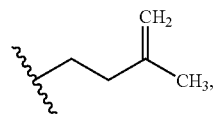,
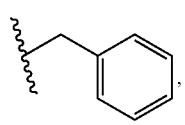 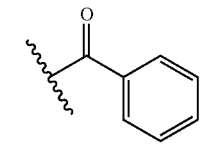 and
.
In another embodiment, $R_{14}$ and/or $R_{15}$ is H.
In another embodiment, $R_{16}$ and $R_{16'}$ are selected from the group consisting of:
H,
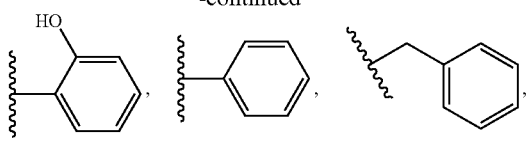
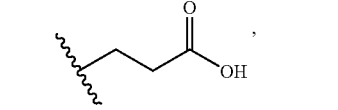
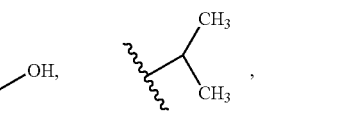
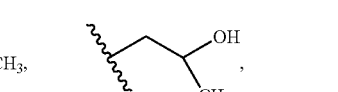
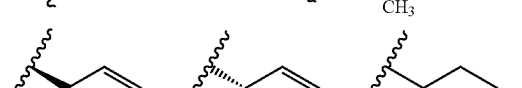
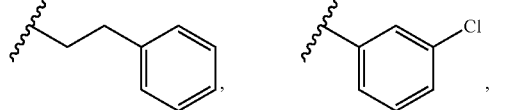
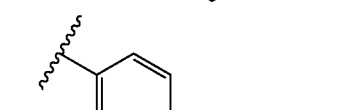
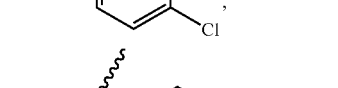
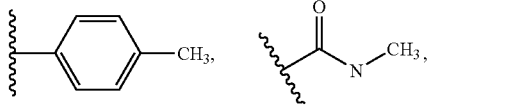
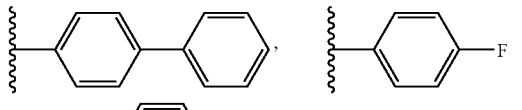
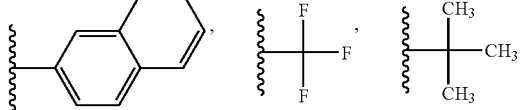
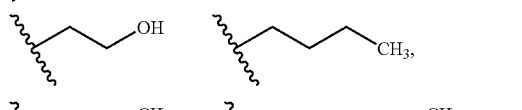
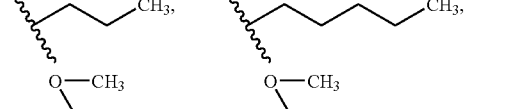
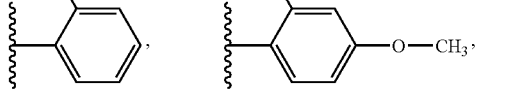

-continued
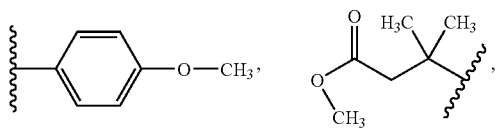
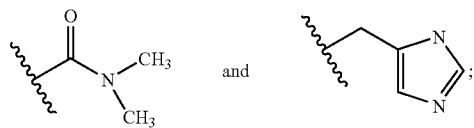
or
R$_{16}$ and R$_{16'}$ taken together is
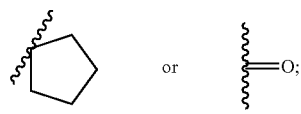
or
R$_{16}$ and Z taken together are
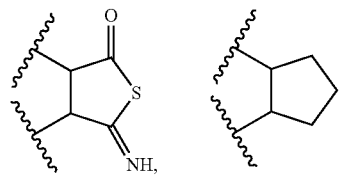
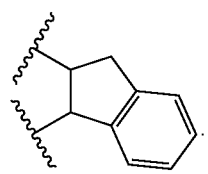
In an additional embodiment, R$_{16}$ and R$_{16'}$ are selected from the group consisting of:
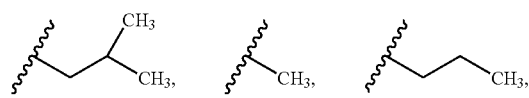
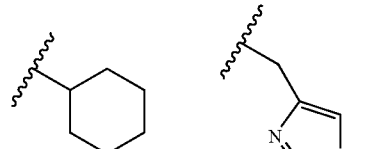
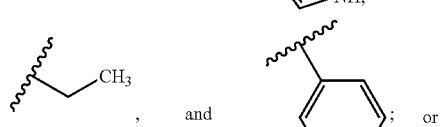
R$_{16}$ and R$_{16'}$ taken together is
; or
R$_{16}$ and Z taken together is
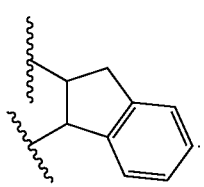.
In another embodiment, Z is present or absent and if present is selected from the group consisting of: H,
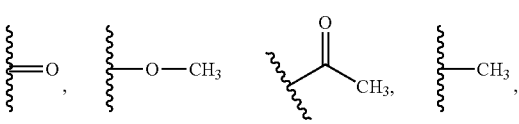
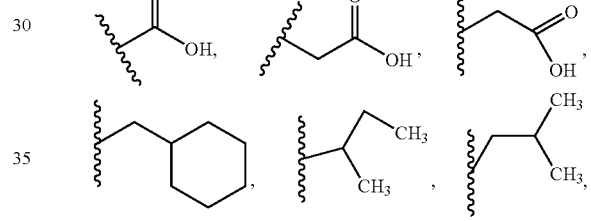
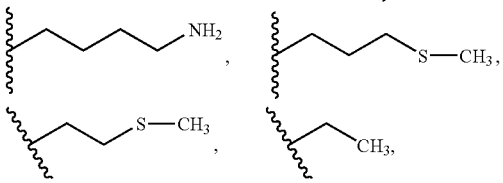
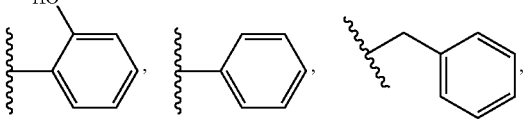
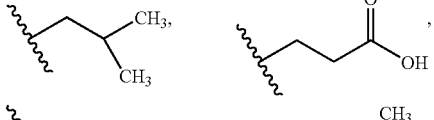
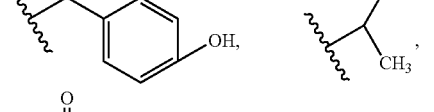
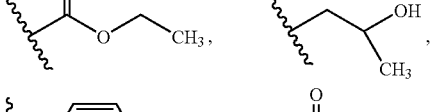
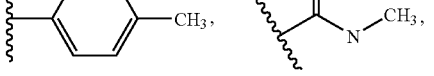

-continued

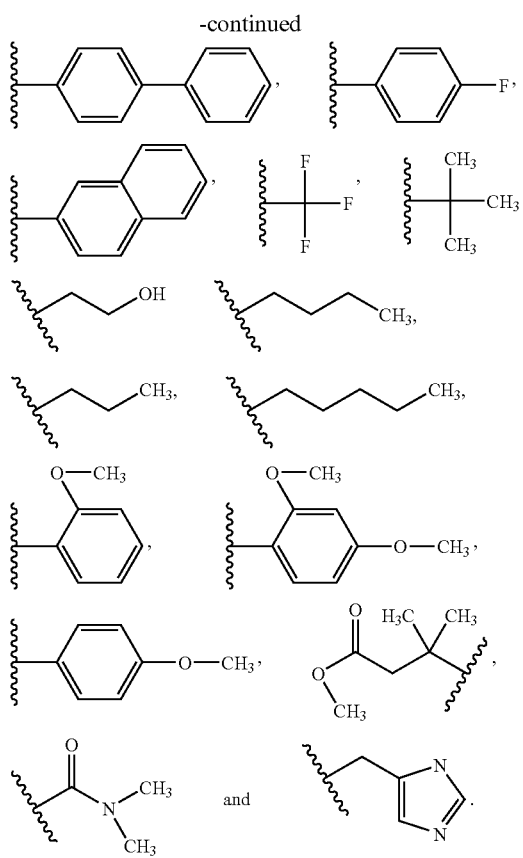

In an additional embodiment, Z is selected from the group consisting of: H,

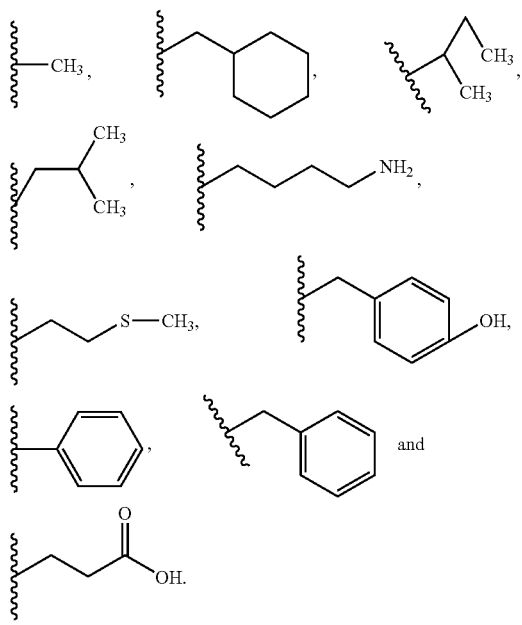

In additional embodiments, Y is S or C; n is 0, 1 or 2; L is alkyl or more specifically, L is —CH$_2$CH$_2$—; X is —CH and R$_{18}$ is H.

In a still another additional embodiment, R$_1$ is

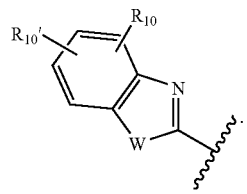

R$_{10}$ and R$_{10}'$ are the same or different and are independently selected from the group consisting of: H, halogen, alkyl, aryl, arylalkyl, heteroaryl, heteroarylalkyl, alkoxyalkyl, hydroxy, nitro, cyano, thio, alkylcarbonyl, alkylsulfonyl and alkoxy;

and

W is S, O or N and when W is N, N is unsubstituted or substituted with alkyl, arylalkyl, heteroarylalkyl, aryl or heteroaryl. More particular embodiments include those compounds wherein W is S'

R$_{10}$ is selected from the group consisting of: H

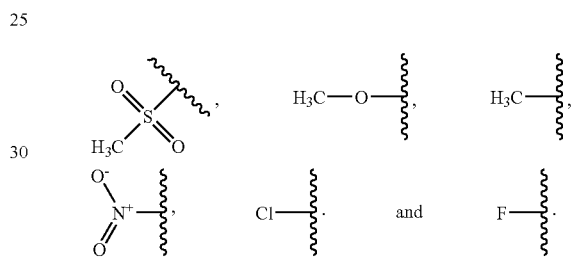

Even more particular are those compounds wherein R$_{10}'$ is H or Cl.

In a still additional embodiment, is a compound of structural Formula 3:

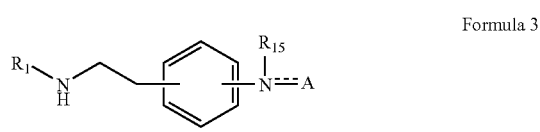

Formula 3 wherein R$_1$, R$_{15}$ and A are herein defined.

In a still additional embodiment, is a compound of structural Formula 4:

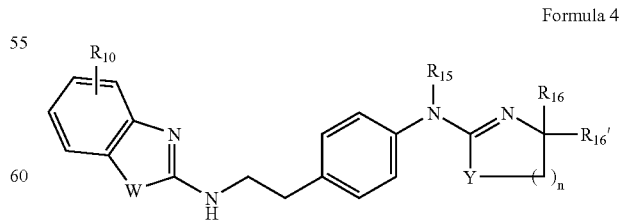

Formula 4 wherein R$_{10}$ is selected from the group consisting of: H, halogen, alkyl, aryl, arylalkyl, heteroaryl, heteroarylalkyl, alkoxyalkyl, hydroxy, nitro, cyano, thio, alkylcarbonyl, alkylsulfonyl and alkoxy; and W is S, O or N with the proviso that when W is N, N is substituted with H, alkyl, arylalkyl, heteroarylalkyl, aryl or heteroaryl.

In a still additional embodiment, is a compound of structural Formula 5:

Formula 5

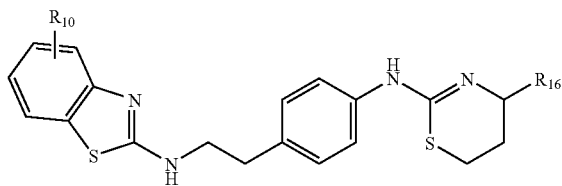

wherein $R_{10}$ and $R_{16}$ are herein defined. More particularly, $R^{16}$ is selected from the group consisting of: $CH_3$,

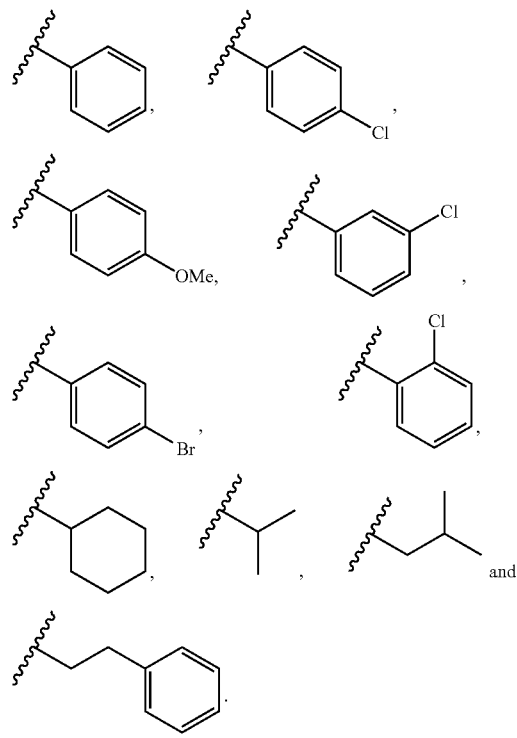

In a still additional embodiment, is a compound of structural Formula 6:

Formula 6

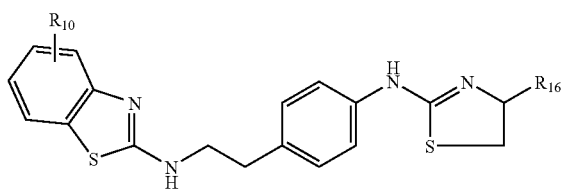

wherein $R_{10}$ and $R_{16}$ are herein defined. More particularly, $R_{16}$ is:

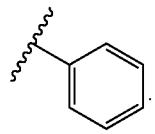

In a still additional embodiment, $R_1$ is

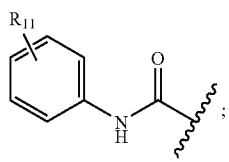

and $R_{11}$ is selected from the group consisting of: H, halogen, alkyl, aryl, aralkyl, heteroaryl, heteroarylalkyl, alkoxyalkyl, hydroxy, nitro, cyano, thio and alkylcarbonyl.

In a still additional embodiment, is a compound of structural Formula 7:

Formula 7

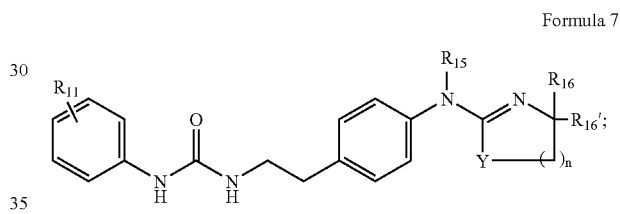

and $R_{11}$ is selected from the group consisting of: H, halogen, alkyl, aryl, aralkyl, heteroaryl, heteroarylalkyl, alkoxyalkyl, hydroxy, nitro, cyano, thio and alkylcarbonyl.

In yet an additional embodiment, is a compound represented by structural Formula 8:

Formula 8

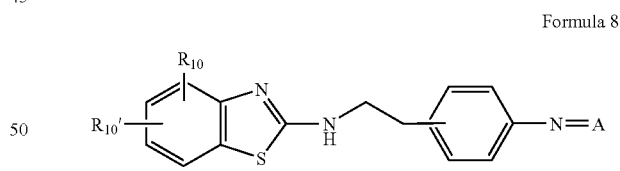

wherein:
$R_{10}$ is H, $-OCH_3$, $-CH_3$, Cl or F;
$R_{10'}$ is H or Cl;
and
A is selected from the following structures:

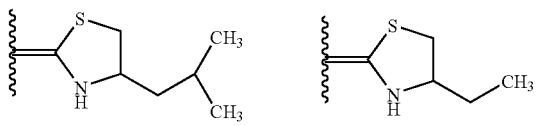

-continued

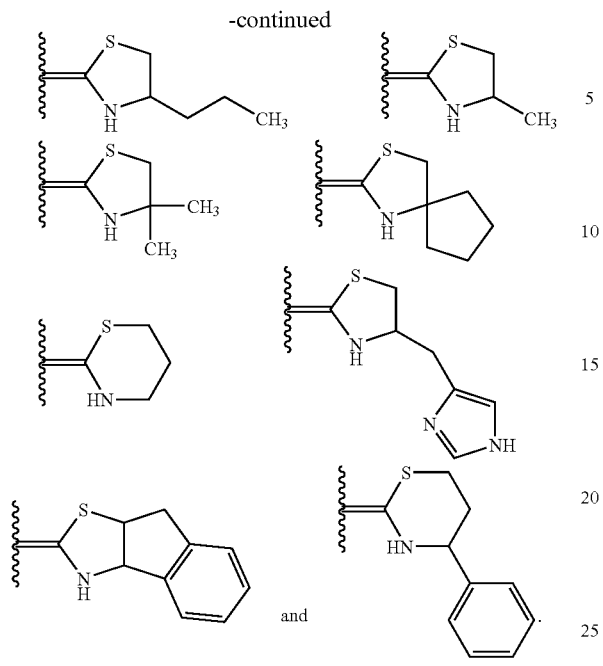

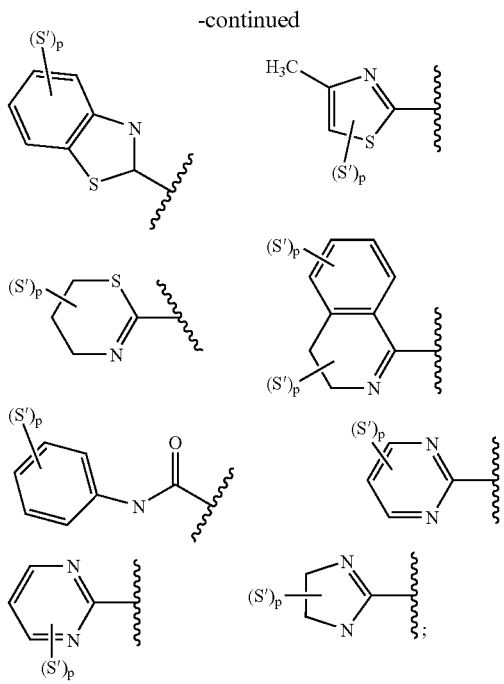

More particular embodiments, are those compounds of structural Formulas 9, 10 and 11 below:

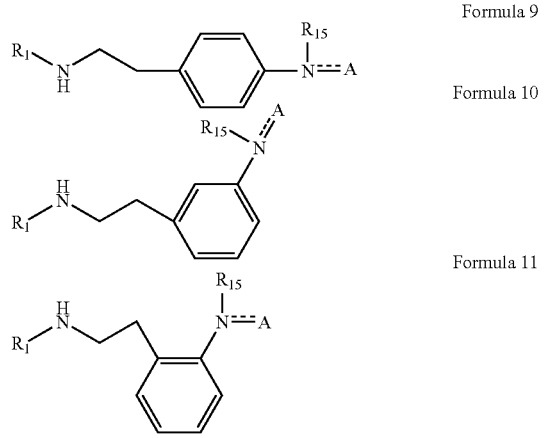

In yet an additional embodiment, is compound of Formula 1, with the proviso that when either condition (iii) or condition (iv) is satisfied, then at least one of $R_{16}$, $R_{16'}$, $R_{18}$, and Z is present and is a substituent other than H;

condition (iii) is satisfied when the compound of Formula 1 is

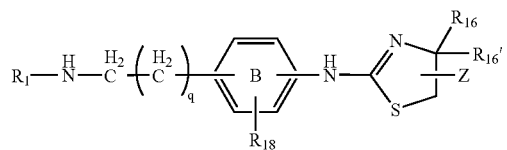

wherein $R_1$ is selected from the following structures:

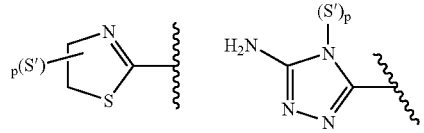

q is 1 or 2;
p is an integer from 1 to 5;

and

S' is independently selected from the group consisting of: H, halogen, alkyl, cycloalkyl, cycloalkylalkyl, alkoxy, thio, alkylsulfonyl, alkoxyalkyl, heterocycloalkyl, heterocycloalkylalkyl, arylalkyl, heteroarylalkyl, aryl, heteroaryl, —$OR_{20}$, —CN, —$NO_2$, —$NR_{20}R_{21}$, —$C(O)R_{20}$, —$C(O)OR_{20}$, —$C(O)NR_{20}R_{21}$, —$S(O)_{0-2}NR_{20}R_{21}$, —$CF_3$, —$OCF_3$, —$CF_2CF_3$, —$C(=N-OR_{20})R_{21}$, —$N(R_{20})S(O)_{0-2}R_{21}$, —$N(R_{20})C(O)(R_{21})$, —$N(R_{20})C(O)NR_{21}R_{22}$, —$C(O)N(R_{20})(R_{21})$, —$SO_2R_{20}$ and —$SO_2N(R_{20})(R_{21})$;

condition (iv) is satisfied when the compound of Formula 1 is

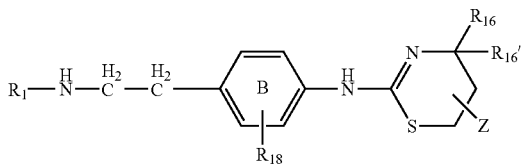

wherein $R_1$ is optionally substituted or unsubstituted and selected from the following structures:

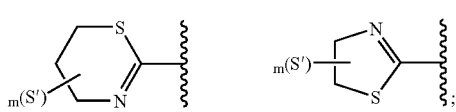

m is an integer from 1 to 5; and
S' is independently selected from the group consisting of: H, halogen, alkyl, cycloalkyl, cycloalkylalkyl, alkoxy, thio, alkylsulfonyl, alkoxyalkyl, heterocycloalkyl, heterocycloalkylalkyl, arylalkyl, heteroarylalkyl, aryl, heteroaryl, —$OR_{20}$, —CN, —$NO_2$, —$NR_{20}R_{21}$, —$C(O)R_{20}$, —$C(O)OR_{20}$, —$C(O)NR_{20}R_{21}$, —$S(O)_{0-2}NR_{20}R_{21}$, —$CF_3$, —$OCF_3$, —$CF_2CF_3$, —$C(=N-OR_{20})R_{21}$, —$N(R_{20})S(O)_{0-2}R_{21}$, —$N(R_{20})C(O)(R_{21})$, —$N(R_{20})C(O)NR_{21}R_{22}$, —$C(O)N(R_{20})(R_{21})$, —$SO_2R_{20}$ and —$SO_2N(R_{20})(R_{21})$. More particular embodiments, are those compounds of structural Formulas 12, 13, 14, 15 and 16.

Formula 12

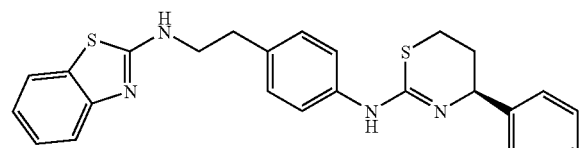

Formula 13

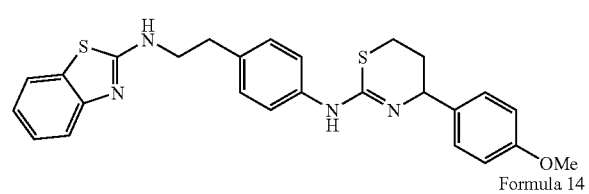

Formula 14

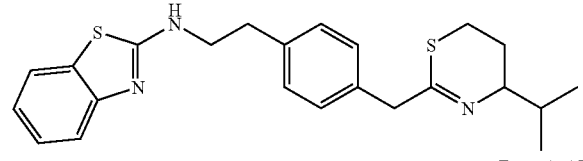

Formula 15

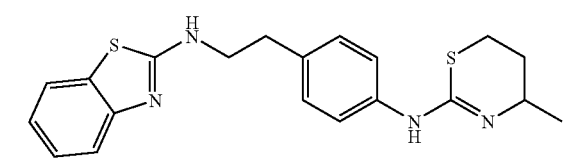

Formula 16

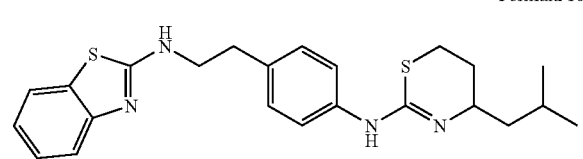

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "heteroarylalkyl", "—$N(R^6)C(O)Oalkyl$, etc.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula 1 or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

Polymorphic forms of the compounds of Formula 1 and of the salts, solvates and prodrugs of the compounds of Formula 1, are intended to be included in the present invention.

"Patient" includes both human and animals.

"Mammal" means humans and other mammalian animals.

"Spiroalkyl" means an alkyl ring system such that at least one carbon atom is shared by the ring and parent moiety. The spiroalkyl group can be optionally substituted with one or more "ring system substituents" which may be the same or different, and are as defined herein.

"Carbonyl" means and includes carbonyl moieties optionally substituted with alkyl, aryl, or other moieties linked to the parent moiety through the carbonyl carbon atom.

"Insulin" (including orally bioavailable insulin preparations), an insulin mimetic, metformin, acarbose.

"Diluent" means substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy, —C(O)O-alkyl and —S(alkyl). Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain.

Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group may be substituted by one or more substituents which may be the same or different, each substituent being independently selected from the group consisting of alkyl. aryl and cycloalkyl.

"Alkylene" means a difunctional group obtained by removal of a hydrogen atom from an alkyl group that is defined above. Non-limiting examples of alkylene include methylene, ethylene and propylene.

"Aryl" (sometimes abbreviated "ar") means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting examples of suitable alkylaryl groups include o-tolyl, p-tolyl and xylyl. The bond to the parent moiety is through the aryl.

"Alkylamino" means an —$NH_2$ or —$NH_3^+$ group in which one or more of the hydrogen atoms on the nitrogen is replaced by an alkyl group as defined above.

"Alkylaminocarbonyl" means an alkylamino group as defined above linked to an adjacent moiety through a carbonyl group. The alkylaminocarbonyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocycloalkyl.

"Arylamino" means an —$NH_2$ or —$NH_3^+$ group in which one or more of the hydrogen atoms on the nitrogen is replaced by an aryl group as defined above.

"Arylaminocarbonyl" means an arylamino group as defined above linked to an adjacent moiety through a carbonyl group. The arylaminocarbonyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocycloalkyl. A non-limiting example of arylaminocarbonyl is N-arylaminocarbonyl.

"Heteroarylamino" means a heteroaryl as defined above linked to an adjacent moiety through an amino group. The heteroarylamino can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocycloalkyl.

"Heteroarylaminocarbonyl" means a heteroarylamino as defined above linked to an adjacent moiety through a carbonyl group. The heteroarylaminocarbonyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocycloalkyl. A non-limiting example of heteroarylaminocarbonyl is N-heteroarylaminocarbonyl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, indanyl, adamantyl and the like. The abbreviation "cy" represents cyclohexyl.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Haloalkyl" means an alkyl as defined above wherein one or more hydrogen atoms on the alkyl is replaced by a halo group defined above.

"Haloaryl" means an aryl as defined above wherein one or more hydrogen atoms on the aryl is replaced by a halo group as defined above.

"Ring system substituent" means a substituent attached to an aromatic or non-aromatic ring system which, for example, replaces an available hydrogen on the ring system. Ring system substituents may be the same or different, each being independently selected from the group consisting of alkyl, aryl, heteroaryl, aralkyl, alkylaryl, $OCF_3$, OCOalkyl, OCOaryl, $CF_3$, aralkenyl, heteroaralkyl, alkylheteroaryl, heteroaralkenyl, hydroxy, hydroxyalkyl, alkoxy, aryloxy, aralkoxy, acyl, aroyl, halogen, nitro, cyano, carboxy, alkoxycarbonyl, aryloxycarbonyl, aralkoxycarbonyl, ketone, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocycloalkyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl. "Ring system substituent" also means a cyclic ring of 3 to 7 ring atoms of which 1-2 may be a heteroatom, attached to an alkyl, aryl, heteroaryl, heterocycloalkyl or heterocyclenyl ring by simultaneously substituting two ring hydrogen atoms on said aryl, heteroaryl, heterocycloalkyl or heterocyclenyl ring. Non-limiting examples include:

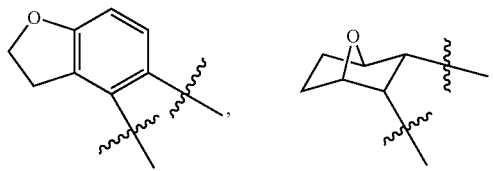

and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocycloalkyl" (or heterocyclyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Arylcycloalkenyl" means a group derived from a fused aryl and cycloalkenyl as defined herein by removal of a hydrogen atom from the cycloalkenyl portion. Preferred arylcycloalkenyls are those wherein aryl is phenyl and the cycloalkenyl consists of about 5 to about 6 ring atoms. The arylcycloalkenyl can be optionally substituted by one or more ring system substituents, wherein "ring system substituent" is as defined above. Non-limiting examples of suitable arylcycloalkenyls include 1,2-dihydronaphthalene, indene, and the like. The bond to the parent moiety is through a non-aromatic carbon atom.

"Cycloalkenylaryl" means a group derived from a fused arylcycloalkenyl as defined herein by removal of hydrogen atom from the aryl portion. Non-limiting examples of suitable cycloalkenylaryls are as described herein for a arylcycloalkenyl, except that the bond to the parent moiety is through an aromatic carbon atom.

"Arylcycloalkyl" means a group derived from a fused aryl and cycloalkyl as defined herein by removal of a hydrogen atom from the cycloalkyl portion. Preferred arylcycloalkyls are those wherein aryl is phenyl and the cycloalkyl consists of about 5 to about 6 ring atoms. The arylcycloalkyl can be optionally substituted by one or more ring system substituents, wherein "ring system substituent" is as defined above. Non-limiting examples of suitable arylcycloalkyls include indanyl, 1,2,3,4-tetrahydronaphthyl, and the like. The bond to the parent moiety is through a non-aromatic carbon atom.

"Cycloalkylaryl" means a group derived from a fused aryl-cycloalkyl as defined herein by removal of a hydrogen atom from the aryl portion. Non-limiting examples of suitable cycloalkylaryls are as described herein for an arylcycloalkyl group, except that the bond to the parent moiety is through an aromatic carbon atom.

"Heteroarylcycloalkyl" means a group derived from a fused heteroaryl and cycloalkyl as defined herein by removal of a hydrogen atom from the cycloalkyl portion. Preferred heteroarylcycloalkyls are those wherein the heteroaryl thereof consists of about 5 to about 6 ring atoms and the cycloalkyl consists of about 5 to about 6 ring atoms. The prefix aza, oxa or thia before heteroaryl means that at least a nitrogen, oxygen or sulfur atom is present respectively as a ring atom. The heteroarylcycloalkyl can be optionally substituted by one or more ring system substituents, wherein "ring system substituent" is as defined above. The nitrogen atom of the heteroaryl portion of the heteroarylcycloalkyl can be optionally oxidized to the corresponding N-oxide. Non-limiting examples of suitable heteroarylcycloalkyls include 5,6,7,8-tetrahydroquinolinyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like. The bond to the parent moiety is through a non-aromatic carbon atom.

"Cycloalkylheteroaryl" means a group derived from a fused beteroarylcycloalkyl as defined herein by removal of a hydrogen atom from the heteroaryl portion. Non-limiting examples of suitable cycloalkylheteroaryls are as described herein for heteroarylcycloalkyl, except that the bond to the parent moiety is through an aromatic carbon atom.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Aralkynyl" means an aryl-alkynyl- group in which the aryl and alkynyl are as previously described. Preferred aralkynyls contain a lower alkynyl group. The bond to the parent moiety is through the alkynyl. Non-limiting examples of suitable aralkynyl groups include phenacetylenyl and naphthylacetylenyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl- group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Alkylamino" means an —$NH_2$ or —$NH_3^+$ group in which one or more of the hydrogen atoms on the nitrogen is replaced by an alkyl group as defined above.

"Arylamino" means an —$NH_2$ or —$NH_3^+$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—C(O)— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O)_2$— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-$S(O)_2$— group. The bond to the parent moiety is through the sulfonyl.

"Arylsulfinyl" means an aryl-S(O)— group. The bond to the parent moiety is through the sulfinyl.

The term "optionally substituted" means optional substitution with the specified groups, radicals or moieties, in available position or positions.

Those skilled in the art will appreciate that the term "neurodegenerative disease" has its commonly accepted medical meaning and describes diseases and conditions resulting from abnormal function of neurons, including neuronal death and abnormal release of neurotransmitters or neurotoxic substances. In this instance it also includes all diseases resulting from abnormal levels of beta amyloid protein. Examples of such diseases include, but are not limited to, Alzheimer's disease, age-related dementia, cerebral or systemic amyloidosis, hereditary cerebral hemorrhage with amyloidosis, and Down's syndrome.

Lines drawn into the ring systems indicate that the indicated bond may be attached to any of the substitutable ring carbon atoms.

As is well known in the art, a bond drawn from a particular atom wherein no moiety is depicted at the terminal end of the bond indicates a methyl group bound through that bond to the atom. For example:

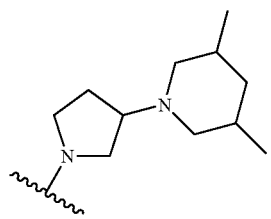 represents

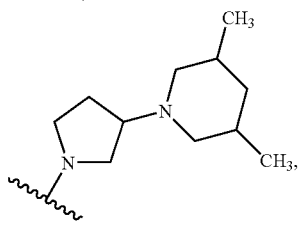

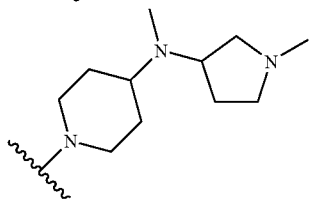 represents

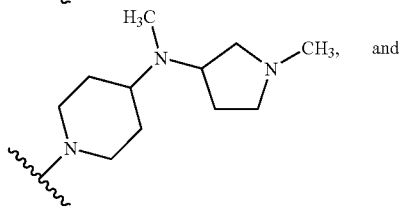 and

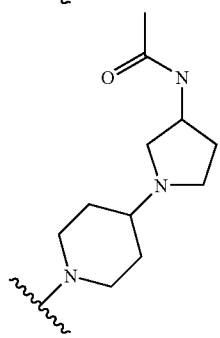 represents

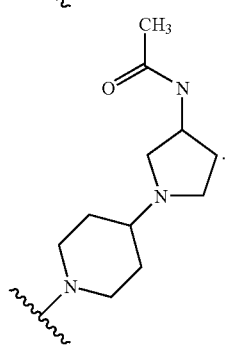

Further wherein the substituents listed above can be linked together in combinations to form one substituent. For example, an arylcycloakyl group would be a substituent comprising and aryl group attached to the parent moiety via a cycloalkyl group. Another example is an alkylthioamino group which is an alkyl group attached to a thio group which is attached to an amino group wherein the alkylthioamino substituent is connected to the parent moiety via the amino group. Also, the definitions above apply regardless of whether a term is used by itself or in combination with other terms. Hence the definition of "alkyl" applies to "alkyl" as well as to the "alkyl" portions of "alkoxy", "alkylamino" etc.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

As used herein, the term "composition" is intended to encompass a product comprising the specified ingredients in the specified amounts, as well as any product which results, directly or indirectly, from combination of the specified ingredients in the specified amounts.

The wavy line ∼∼∼ as a bond generally indicates a mixture of, or either of, the possible isomers, e.g., containing (R)- and (S)-stereochemistry. For example,

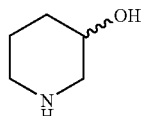 means containing both

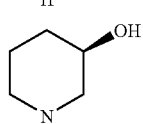 and 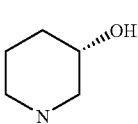

Lines drawn into the ring systems, such as, for example:

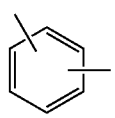

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

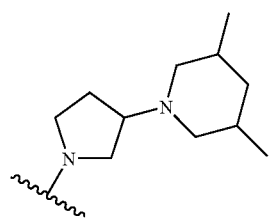 represents

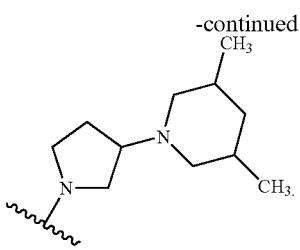

It should also be noted that any carbon or heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula 1 or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

Solvates of the compounds of the invention are also contemplated herein. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound of the present invention effective to treat a mammal (e.g., human) having a disease or condition mediated by Y Y1, and thus producing the desired therapeutic effect.

The compounds of formula 1 form salts which are also within the scope of this invention. Reference to a compound of formula 1 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula 1 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula 1 may be formed, for example, by reacting a compound of formula 1 with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Wash., D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula 1, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Polymorphic forms of the compounds of Formula 1, and of the salts, solvates and prodrugs of the compounds of Formula 1, are intended to be included in the present invention.

"Substituted" means that one or more hydrogens on the designated atom, moiety, group or molecule is replaced with a selection from the indicated group, provided that normal valency under the existing circumstances is not exceeded, and that the substitution results in a stable compound. Combinations of substituents and/or variables are permissible only if such combinations result in stable compounds, "Stable compound" or "stable structure" means a compound that is sufficiently robust to survive isolation to a useful degree of purity from a reaction mixture, and formulation into an efficacious therapeutic agent.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

It should also be noted that any Formula, compound, moiety or chemical illustration with unsatisfied valences in the present specification and/or claims herein is assumed to have the hydrogen atom to satisfy the valences.

When any variable (e.g., aryl, heterocycle, $R^2$, etc.) occurs more than one time in any constituent or in Formula 1, its definition on each occurrence is independent of its definition at every other occurrence. Also, combinations of substituents and/or variables are permissible only if such combinations result in stable compounds.

In its many embodiments, the present invention is directed to pharmaceutical compositions for the treatment of metabolic disorders such as obesity, and eating disorders such as hyperphagia. In one aspect, this invention is also directed to pharmaceutical compositions for the treatment of obesity which comprise an obesity treating amount of a compound of Formula 1,

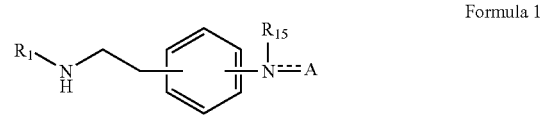

Formula 1

A group of representative compounds, and associated Ki values, are listed in Table 1 below:

TABLE 1

| EX. No. | Structure | Ki(nM) |
| --- | --- | --- |
| 1 | 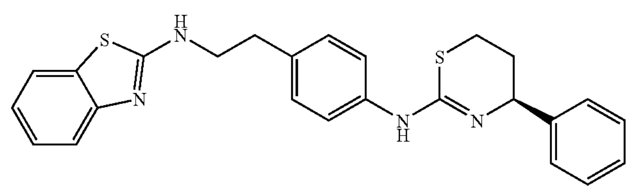 | 24 |
| 2 | 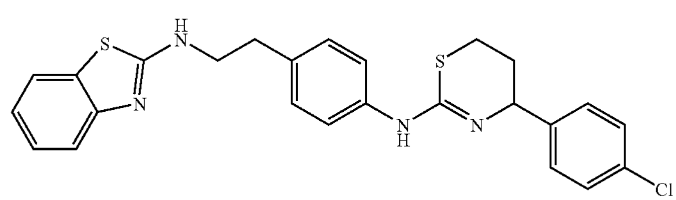 | A |
| 3 | 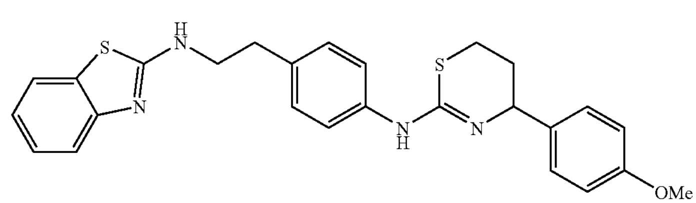 | A |
| 4 | 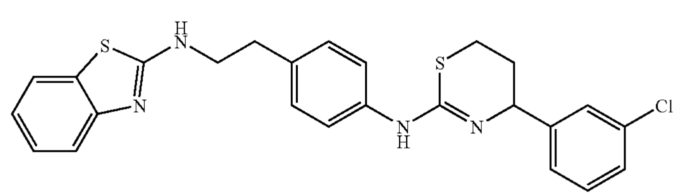 | A |

TABLE 1-continued

| EX. No. | Structure | Ki(nM) |
|---|---|---|
| 5 | benzothiazole-NH-CH2CH2-C6H4-NH-[4-(4-bromophenyl)-5,6-dihydro-4H-1,3-thiazin-2-yl] | A |
| 6 | benzothiazole-NH-CH2CH2-C6H4-NH-[6-phenyl-3,4,5,6-tetrahydropyridin-2-yl] | A |
| 7 | benzothiazole-NH-CH2CH2-C6H4-NH-[(4S)-4-phenyl-4,5-dihydro-1,3-thiazol-2-yl] | A |
| 8 | benzothiazole-NH-CH2CH2-C6H4-NH-[(4R)-4-phenyl-4,5-dihydro-1,3-thiazol-2-yl] | B |
| 9 | benzothiazole-NH-CH2CH2-C6H4-NH-[4-cyclohexyl-5,6-dihydro-4H-1,3-thiazin-2-yl] | A |
| 10 | benzothiazole-NH-CH2CH2-C6H4-NH-[4-isopropyl-5,6-dihydro-4H-1,3-thiazin-2-yl] | A |
| 11 | benzothiazole-NH-CH2CH2-C6H4-NH-[4-methyl-5,6-dihydro-4H-1,3-thiazin-2-yl] | A |
| 12 | benzothiazole-NH-CH2CH2-C6H4-NH-[4-isobutyl-5,6-dihydro-4H-1,3-thiazin-2-yl] | A |

TABLE 1-continued

| EX. No. | Structure | Ki(nM) |
|---|---|---|
| 13 | 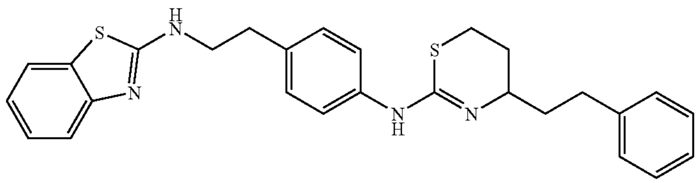 | A |

Compounds of Formula 1 can be useful as highly selective, high affinity NPY Y1 receptor antagonists useful for the treatment of obesity.

In addition to the "direct" effect of the compounds of this invention on the NPY Y1 receptor, these are diseases and conditions that can benefit from the weight loss such as insulin resistance, impaired glucose tolerance, Type II Diabetes, hypertension, hyperlipidemia, cardiovascular disease, gall stones, certain cancers, and sleep apnea.

Compounds of Formula 1, which can be useful as highly selective, high affinity NPY Y1 receptors antagonists, may be used in combination with other compounds including other "different" compounds that are also useful as NPY Y1 receptor antagonists. When the term "different" is used, it is intended that these other compounds are chemically different from the compounds of Formula 1.

Another aspect of this invention is a method of treating a mammal (e.g., human) having a disease or condition mediated by NPY Y1 receptor antagonist by administering a therapeutically effective amount of at least one compound of Formula 1, or a pharmaceutically acceptable salt or solvate of said compound to the mammal.

Another aspect of this invention is directed to a method of treating obesity comprising administering to a mammal in need of such treatment a therapeutically effective amount of at least one compound of Formula 1, or a pharmaceutically acceptable salt or solvate of said compound.

Another aspect of this invention is directed to a method for treating eating and metabolic disorders such as bulimia, hyperphagia and anorexia comprising administering to a mammal a therapeutically effective amount of at least one compound of Formula 1, or a pharmaceutically acceptable salt or solvate of said compound.

Another aspect of this invention is directed to a method for treating hyperlipidemia comprising administering to a mammal a therapeutically effective amount of at least one compound of Formula 1, or a pharmaceutically acceptable salt or solvate of said compound.

Another aspect of this invention is directed to a method for treating cellulite and fat accumulation comprising administering to a mammal a therapeutically effective amount of at least one compound of Formula 1, or a pharmaceutically acceptable salt or solvate of said compound.

Another aspect of this invention is directed to a method for treating type II diabetes comprising administering to a mammal a therapeutically effective amount of at least one compound of Formula 1, or a pharmaceutically acceptable salt or solvate of said compound.

This invention is also directed to pharmaceutical compositions which comprise at least one compound of Formula 1, or a pharmaceutically acceptable salt or solvate of said compound and at least one pharmaceutically acceptable carrier.

This invention is also directed to pharmaceutical compositions for the treatment of obesity which comprise an obesity treating amount of at least one compound of Formula 1, or a pharmaceutically acceptable salt or solvate of said compound and at least one pharmaceutically acceptable carrier.

This invention is also directed to pharmaceutical compositions which comprise at least one compound of Formula 1, or a pharmaceutically acceptable salt or solvate of said compound and at least one pharmaceutically acceptable carrier.

This invention is also directed to pharmaceutical compositions for the treatment of obesity which comprise an obesity treating amount of at least one compound of Formula 1, or a pharmaceutically acceptable salt or solvate of said compound and at least one pharmaceutically acceptable carrier.

Yet another aspect of this invention are combinations of a compound of Formula 1 or a pharmaceutically acceptable salt or solvate of said compound and other compounds as described below.

One such aspect of this invention is a method for treating obesity comprising administering to a mammal (e.g., a female or male human):

a. an amount of at least one first compound, said first compound being a Formula 1 compound or a pharmaceutically acceptable salt or solvate of said compound; and b. an amount of at least one second compound, said second compound being at lease one anti-obesity and/or anorectic agent such as a $\beta_3$ agonist, thyromimetic agent, anorectic agent, or NPY antagonist different from the first compound wherein the amounts of the first and second compounds result in a therapeutic effect.

Yet another aspect of this invention are combinations of a compound of Formula 1, or a pharmaceutically acceptable salt or solvate of said compound and other compounds as described below.

This invention is also directed to a pharmaceutical combination composition comprising: a therapeutically effective amount of a composition comprising:

a. at least one first compound, said first compound being a compound of Formula 1, or a pharmaceutically acceptable salt or solvate of said compound;

b. at least one second compound, said second compound being at least one antiobesity and/or anorectic agent such as a $\beta B_3$ agonist, thyromimetic agent, anorectic, or an NPY antagonist different from the first compound; and/or c. optionally a pharmaceutical carrier, vehicle or diluent.

Another aspect of this invention is a kit comprising:

a. an amount of a compound of Formula 1, or a pharmaceutically acceptable salt or solvate of said compound and a pharmaceutically acceptable carrier, vehicle or diluent in a first unit dosage form;

b. an amount of an antiobesity and/or anorectic agent such as a $\beta_3$ agonist, thyromimetic agent, anorectic agent, or NPY antagonist different from the compound of Formula 1 and a pharmaceutically acceptable carrier, vehicle or diluent in a second unit dosage form; and c. means for containing said first and second dosage forms wherein the amounts of the first and second compounds result in a therapeutic effect.

Another aspect of this invention is a method treating diabetes comprising administering to a mammal (e.g., a female or male human):

a. an amount of a first compound, said first compound being a compound of Formula 1, or a pharmaceutically acceptable salt or solvate of said compound; and b. an amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising:

a first compound, said first compound being a compound of Formula 1, or a pharmaceutically acceptable salt or solvate of said compound;

a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and optionally a pharmaceutical carrier, vehicle or diluent.

Another aspect of this invention is a kit comprising:

a. an amount of a compound of Formula 1, or a pharmaceutically acceptable salt or solvate of said compound and a pharmaceutically acceptable carrier, vehicle or diluent in a first unit dosage form;

b. an amount of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, mefformin, acarbose, a PPAR-gamma ligand such as troglitazone, rosaglitazone, pioglitazone, or GW-1929, a sulfonylurea, glipazide, glyburide, or chlorpropamide and a pharmaceutically acceptable carrier, vehicle or diluent in a second unit dosage form; and c. means for containing said first and second dosage forms wherein the amounts of the first and second compounds result in a therapeutic effect.

Still another aspect of this invention is a method of treating a metabolic disorder, an eating disorder or diabetes comprising administering to a mammal in need of such treatment a therapeutically effective amount of at least one compound represented by the structural Formula 1:

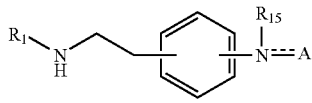

Formula 1

The compounds of Formula 1 can exhibit NPY Y1 receptor antagonizing activity, which has been correlated with pharmaceutical activity for treating eating disorders, such as obesity and hyperphagia, and diabetes.

The compounds of Formula 1 display pharmacological activity in a test procedure designed to demonstrate NPY Y1 receptor antagonist activity. The compounds are non-toxic at pharmaceutically therapeutic doses.

Preferred antiobesity and/or anorectic agents (taken singly or in any combination thereof) in the above combination methods, combination compositions and combination kits are:

phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as or list at). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent compound of Formula 1. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 50 mg, more preferably from about 1 mg to about 25 mg, according to the particular application.

A useful dosage is about 0.001 to 100 mg/kg of body weight/day of the compound of Formula 1. A preferred dosage is about 0.01 to 25 mg/kg of body weight/day of a compound of Formula 1, or a pharmaceutically acceptable salt or solvate of said compound.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

Another embodiment of the invention discloses a method of making the compounds disclosed herein. The compounds may be prepared by several techniques known in the art. The invention disclosed herein is then further exemplified by representative preparative examples which are followed by additional example compounds made therefrom which should not be construed to limit the scope of the invention which is defined in the appended claims. If applicable, the Ki values for compounds shown in the tables below are rated, "A" for Ki values less than 1000 nanomolar (nM), "B" for Ki values greater than and including 1000 nM to and including 10,000 nM and "C" for Ki values greater than 10,000 nM. (Starting materials are prepared by known methods and/or methods described in the Preparations.) Alternative mechanistic pathways and analogous structures will be apparent to those skilled in the art. For example, compounds of Formula 1, can be produced by processes known to those skilled in the art using either solution phase or solid phase synthesis as shown in the following reaction schemes, preparations and examples below. Combinatorial libraries of compounds of Formula 1 can also be prepared using solid phase chemistry as shown in the procedures below.

All NMR data was collected on a 400 MHz NMR spectrometer unless otherwise indicated. LC-Electrospray-Mass spectroscopy was used to determine the molecular mass and retention time. LCMS data was acquired with a C-18 column eluting with 5% to 95% MeCN in water.

The following constituents, solvents and reagents may be referred to by their abbreviations in parenthesis:

ADDP (1,1'-(Azodicarbonyl)dipiperidine);
Boc (tert-butoxycarbonyl);
$CH_3NH_2$ (methylamine);
$CH_3CN$ (acetonitrile);
$CH_2Cl_2$ (methylene dichloride);
DBU (1,8-diazabicyclo[5,4,0]undec-7-ene);
DCM (dichloromethane);
DIEA diisopropylethylamine;
DIPEA (N,N'-diisopropylethylamine);
DME (1,2-dimethoxyethane);
DMF (N,N'-Dimethylformamide);
EDCl (1-(3-Dimethylaminopropyl)-3-ethylcarbodiimide hydrochloride);
eq (Equivalent);
EtOAc (ethyl acetate);
$Et_3N$ (triethylamine);
Fmoc (9-fluorenylmethoxycarbonyl);
g (Gram);
h (hour)
HOAc (Acetic acid);
MeOH (methanol);
mL (Milliliter);
Min (Minutes);
mg (Milligram);
MW (Molecular Weight);
$NaBH(OAc)_3$ (sodium triacetoxyborohydride);
$Na_2SO_4$ (sodium sulfate);
$NaHCO_3$ (sodium bicarbonate);
NMP (1-Methyl-2-pyrrolidinone);
$R_t$ (Retention Time);
rt (Room Temperature);
TEA (triethylamine);
TFA (Trifluoroacetic acid);
TLC (thin-layer chromatography);
THF (tetrahydrofuran); and
TMAD (N,N,N', N',-Tetramethylazodicarboxamide).

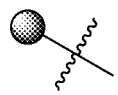

represents a resin for solid phase synthesis.

GENERAL PREPARATIVE SCHEMES AND PROCEDURES FOR PREPARATIVE EXAMPLES

Additional Compounds of Formula 1 can be prepared by the following Procedures:

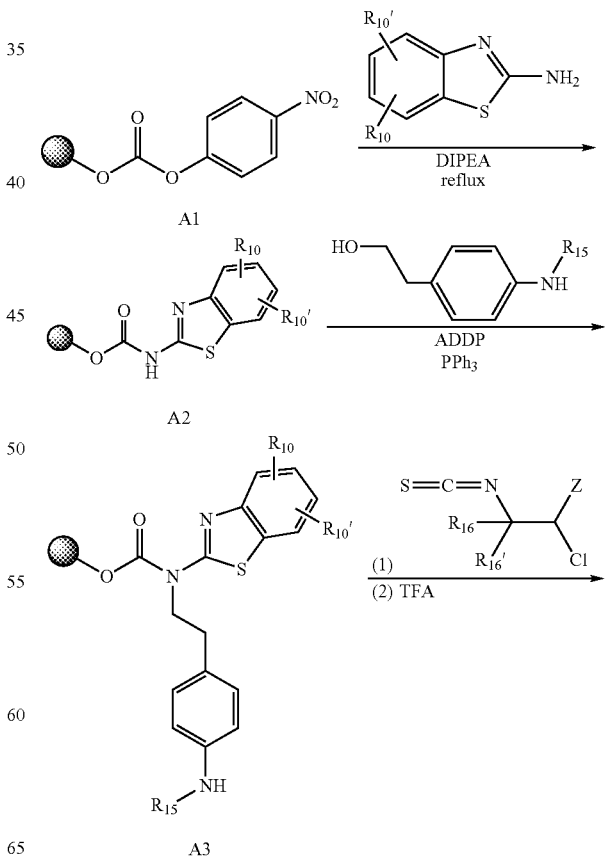

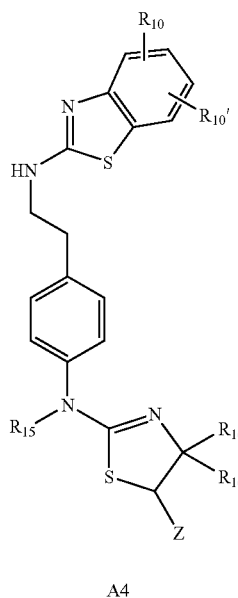

A4

Procedure A, Step 1:

6-Fluoro-2-aminobenzothiazole (44.5 mmol, 10 eq) and 2 M diisopropylethylamine in NMP (13.35 mL, 26.7 mmol, 6 eq) were added to pnitrophenolcarbonate Wang resin (5 g, 0.89 mmol/g) suspended in anhydrous DMF (37.5 mL). The mixture was shaken at 60° C. overnight. The resin was washed with DMF (4×) and then treated with 5% DBU in a 1:1 solvent mixture of $CH_3OH:DMF$ (3×5 min). The resin was washed with DMF (4×), 5% HOAc in DCM (3×), 1:1 solvent mixture of $DMF:H_2O$ (3×), $CH_3OH$ (3×), THF (3×) and DCM (3×) to afford resin A2 where $R_{10}$ is 6-fluoro and $R_{10'}$ is H.

Procedure A, Step 2:

The resin A2 where $R_{10}$ is 6-fluoro and $R_{10'}$ is H (17.8 mmol) was suspended in an 1:1 solvent mixture of anhydrous THF:DCM (310 mL). p-Aminophenethyl alcohol (12.21 g, 89 mmol) and triphenylphospine (23.32 g, 89 mmol) were added to the suspension. The reaction mixture was agitated until all of the triphenylphosphine was dissolved. A solution of 1,1'-(Azodicarbonyl)dipiperidine (22.5 g, 89 mmol) in 50 mL of DCM was added dropwise to the suspension under $N_2$ (g). The reaction mixture was shaken overnight. The resin was washed with a 1:1 solvent mixture of anhydrous THF:DCM (4×) and then treated with 5% HOAc in a 1:1 solvent mixture of anhydrous THF:DCM. After one hour, the resin was rinsed with DMF (1×), 5% diisopropylethylamine in a 3:1 DMF:THF solvent mixture, DMF (3×), THF (3×), $CH_3OH$ (3×) and DCM (3×) to yield resin A3 where $R_{10}$ is 6-fluoro, $R_{10'}$ is H and $R_{15}$ is H.

Procedure A, Step 3:

2-Chloroethyl isothiocyanate (3 eq) was added to pre-swelled resin A3 ($R_{10}$ is 6-fluoro, $R_{10'}$ is H, and $R_{15}$ is H) in anhydrous DCM. The reaction mixture was agitated overnight. The resin was washed with THF (4×) and DCM (4×). The resin was cleaved with 50% TFA in DCM (2 h) and the filtrate was concentrated to yield A4 where $R_{10}$ is 6-fluoro, $R_{10'}$ is H, $R_{15}$ is H, $R_{16}$ is H, $R_{16'}$ is H, and Z is H.

The following compounds were prepared using analogous methods:

| Ex. No. | Structure | Ki | Exact Mass (g/mol) | Obs. Mass (M + 1) |
|---|---|---|---|---|
| 14 | 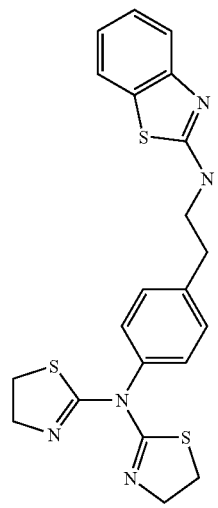 | C | 439 | 440.11 |

-continued

| Ex. No. | Structure | Ki | Exact Mass (g/mol) | Obs. Mass (M + 1) |
|---|---|---|---|---|
| 15 | *(structure)* | B | 432 | 433.11 |
| 16 | *(structure)* | B | 384 | 385.1 |
| 17 | *(structure)* | B | 368 | 369.09 |
| 18 | *(structure)* | B | 399 | 400.1 |

-continued

| Ex. No. | Structure | Ki | Exact Mass (g/mol) | Obs. Mass (M + 1) |
|---|---|---|---|---|
| 19 | 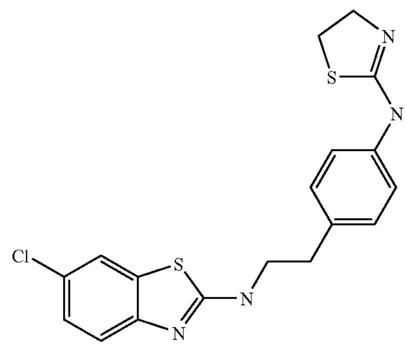 | B | 388 | 389.1 |
| 20 | 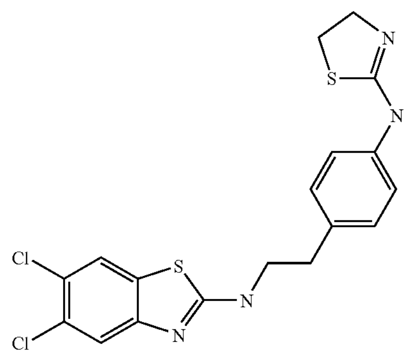 | B | 422 | 423.1 |
| 21 | 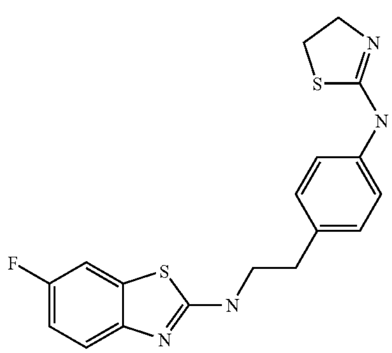 | B | 372 | 373.09 |
| 22 | 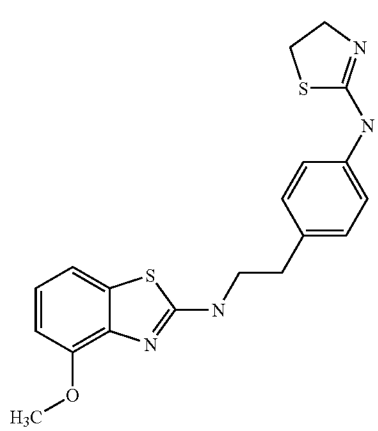 | B | 384 | 385.1 |

-continued
| Ex. No. | Structure | Ki | Exact Mass (g/mol) | Obs. Mass (M + 1) |
|---|---|---|---|---|
| 23 | 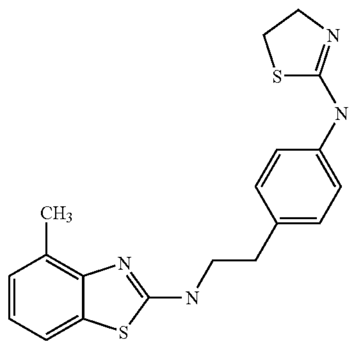 | B | 368 | 369.09 |
| 24 | 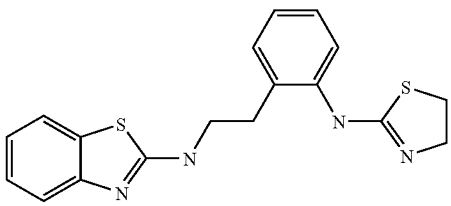 | C | 354 | 355.09 |
| 25 | 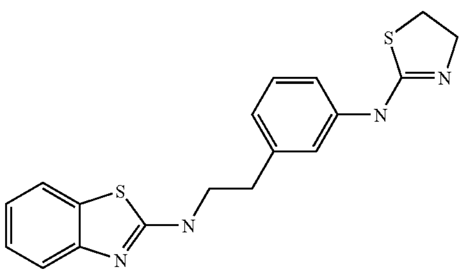 | C | 354 | 355.09 |
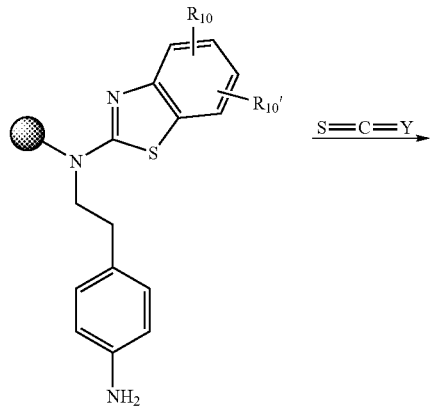
Procedure B
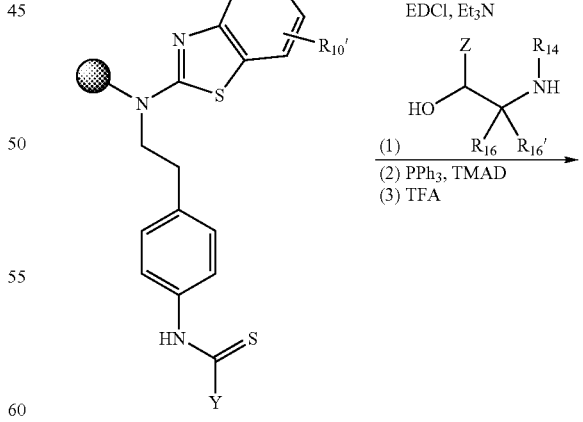

-continued

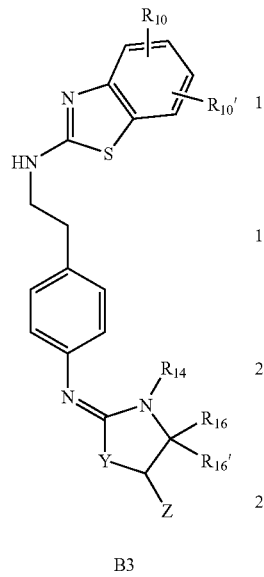

B3

Procedure B, Step 1:

Ethyloxycarbonyl isothiocyanate (295 mg, 2.25 mmol) was added to resin B1 ($R_{10}$ is H, and $R_{10'}$ is H) (500 mg) suspended in DCM (6 mL). The mixture was shaken overnight at RT. The resin was washed with THF (5×) and DCM (5×) to afford B2 where $R_{10}$ is H, $R_{10'}$ is H, and Y is $NHCO_2CH_2CH_3$.

Procedure B, Step 2:

Aminoethanol (16.3 mg, 0.267 mmol) and triethylamine (50 µL, 0.36 mmol) were added to B2 ($R_{10}$ is H, $R_{10'}$ is H, and Y is $NHCO_2CH_2CH_3$) (100 mg) in NMP (2 mL). 1-(3-Dimethylaminopropyl)-3-ethylcarbodiimide hydrochloride (51.2 mg, 0.267 mmol) was added to the mixture and the reaction was shaken overnight. The resin was washed with DMF (3×), THF (4×) and DCM (4×). Triphenylphospine (58 mg, 0.22 mmol) was added to the resin (50 mg) suspended in a 1:1 mixture of anhydrous THF:DCM (0.5 mL) and the mixture was shaken until the solid dissolved. A solution of TMAD (38 mg, 0.22 mmol) in a 1:1 mixture of THF:DCM (0.5 mL) was added and the reaction mixture was shaken. After 5 h, the resin was washed with DMF (3×), THF (4×), and DCM (4×). The resin was cleaved with 50% TFA in DCM for 1.5 h. The filtrate was concentrated to afford B3 ($R_{10}$ is H, $R_{10'}$ is H, $R_{14}$ is H, Z is H, $R_{16}$ is H, $R_{16'}$ is H, and Y is $NHCO_2CH_2CH_3$).

The following compounds were prepared using analogous methods:

| Ex. No. | Structure | Ki | Exact Mass (g/mol) | Obs. Mass (M + 1) |
|---|---|---|---|---|
| 26 | 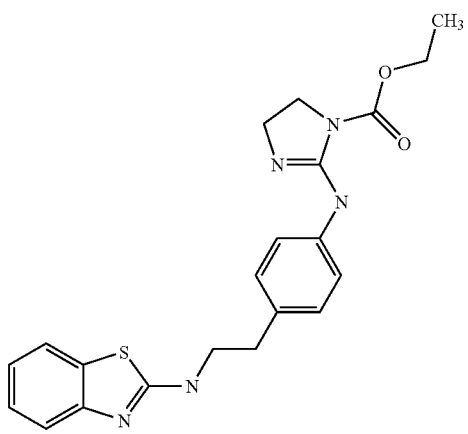 | C | 409 | 410.1 |

-continued

| Ex. No. | Structure | Ki | Exact Mass (g/mol) | Obs. Mass (M + 1) |
|---|---|---|---|---|
| 27 | 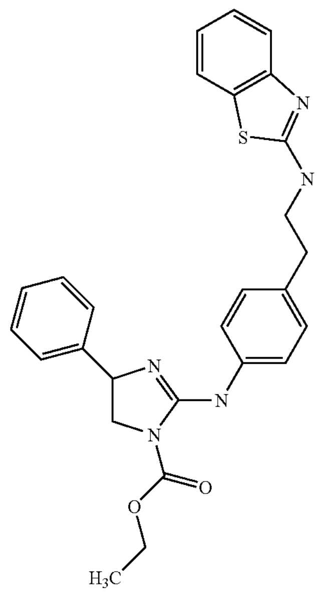 | C | 485 | 486.12 |
| 28 | 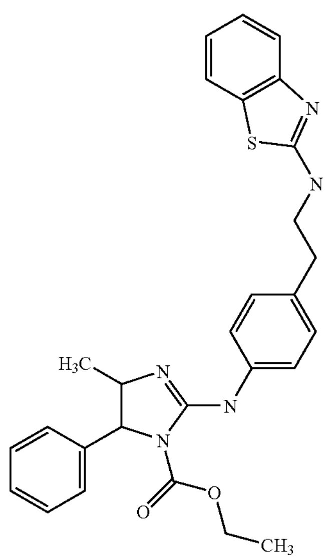 | C | 499 | 500.12 |
| 29 | 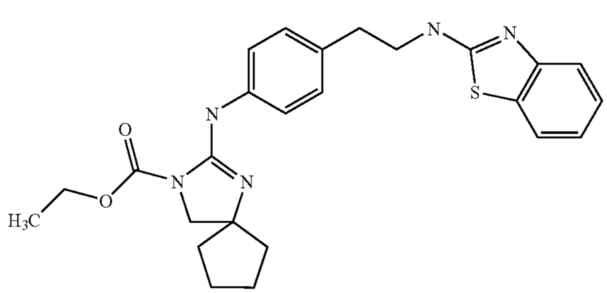 | C | 463 | 464.11 |

-continued
| Ex. No. | Structure | Ki | Exact Mass (g/mol) | Obs. Mass (M + 1) |
|---|---|---|---|---|
| 30 | 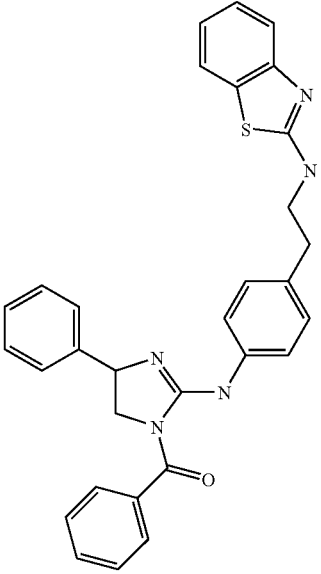 | C | 517 | 518.12 |
| 31 | 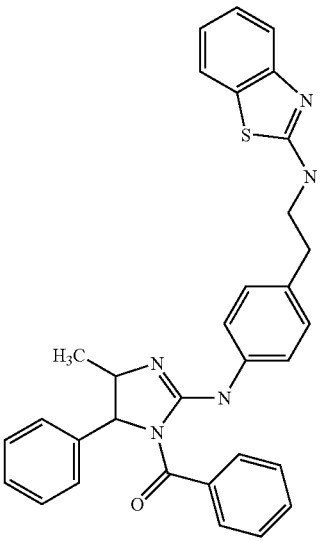 | C | 531 | 532.13 |
| 32 | 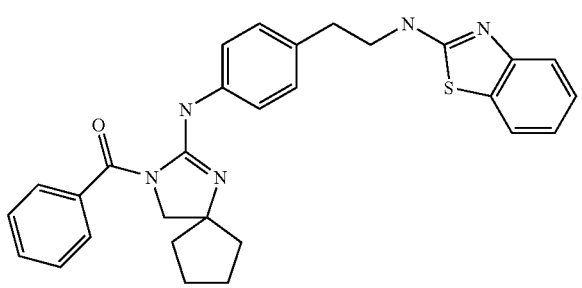 | C | 495 | 496.12 |

-continued

| Ex. No. | Structure | Ki | Exact Mass (g/mol) | Obs. Mass (M + 1) |
|---|---|---|---|---|
| 33 | 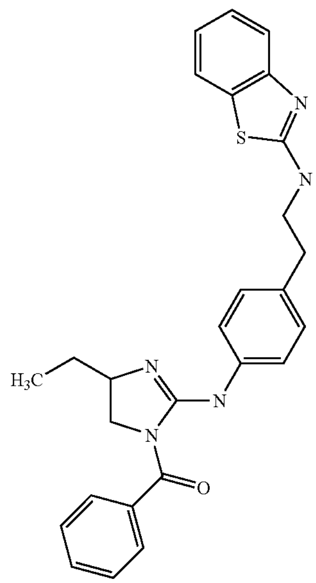 | C | 469 | 470.11 |
| 34 | 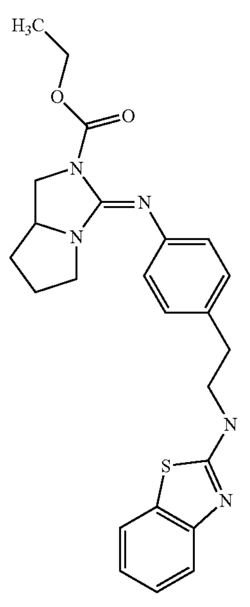 | C | 449 | 450.11 |

-continued
| Ex. No. | Structure | Ki | Exact Mass (g/mol) | Obs. Mass (M + 1) |
|---|---|---|---|---|
| 35 | 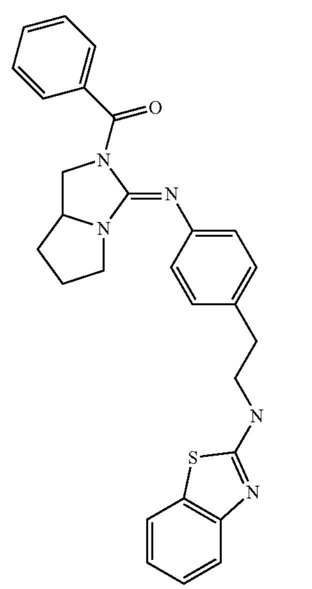 | C | 481 | 482.12 |
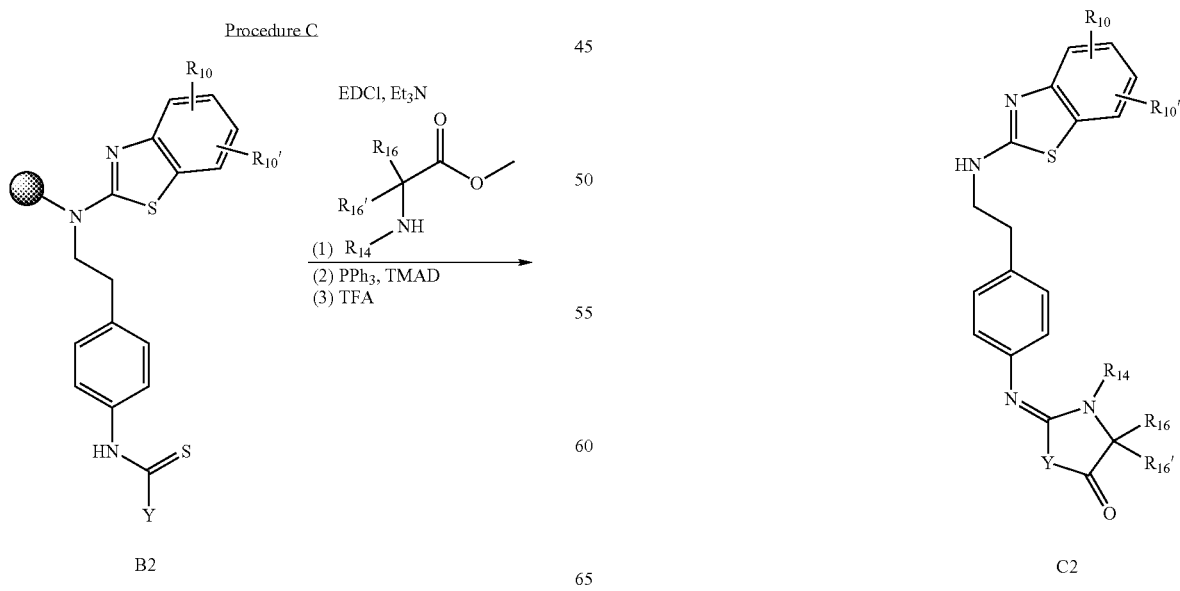

Procedure C, Step 1:

Alanine methyl ester hydrochloride (52.2 mg, 0.37 mmol) and triethylamine (138 μL, 0.992 mmol) were added to B2 ($R_{10}$ is H, $R_{10'}$ is H, and Y is $NHCO_2CH_2CH_3$) (140 mg) in NMP (3 mL). The mixture was shaken for 15 min. EDCl (71.5 mg, 0.374 mmol) was added and the reaction was shaken overnight. The resin was washed with DMF (4×), THF (4×), and DCM (4×). A 21% solution of sodium ethoxide/ethanol (9 μL, 0.02 mmol) in DCM (1.0 mL) was added to the resin (70 mg) suspended in DCM (1 mL). After shaking for 5 h, the resin was washed with DCM (1×), $H_2O$ (1×), THF (4×), and DCM (5×). The resin was cleaved with 20% TFA in DCM for 2 h and the filtrate was concentrated to afford C2 ($R_{10}$ is H, $R_{10'}$ is H, $R_{14}$ is H, $R_{16}$ is H, $R_{16'}$ is H, and Y is $NHCO_2CH_2CH_3$).

The following compounds were prepared using analogous methods:

| Ex. No. | Structure | Ki | Exact Mass (g/mol) | Obs. Mass (M + 1) |
|---|---|---|---|---|
| 36 | 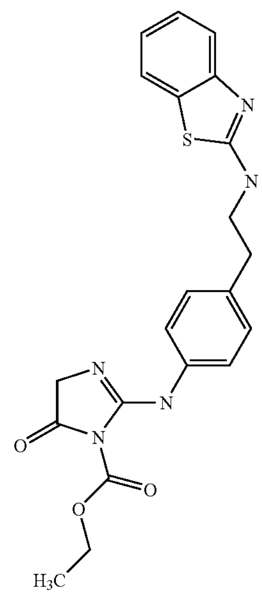 | C | 423 | 424.1 |
| 37 | 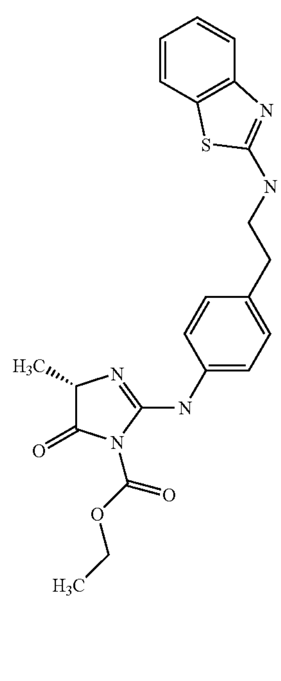 | C | 437 | 438.11 |

| Ex. No. | Structure | Ki | Exact Mass (g/mol) | Obs. Mass (M + 1) |
|---|---|---|---|---|
| 38 | 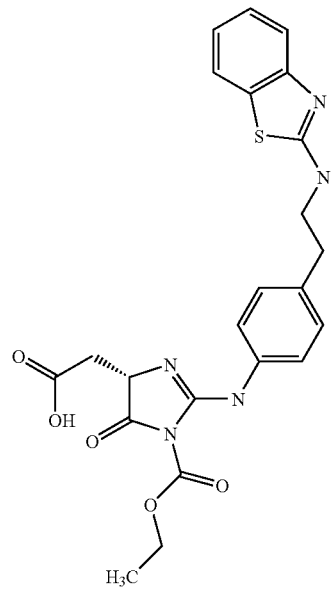 | C | 481 | 482.12 |
| 39 | 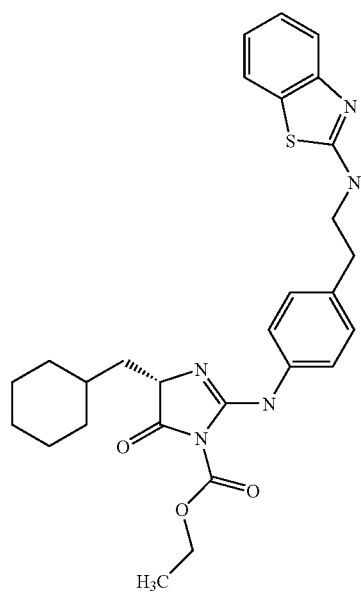 | C | 519 | 520.12 |

-continued
| Ex. No. | Structure | Ki | Exact Mass (g/mol) | Obs. Mass (M + 1) |
|---|---|---|---|---|
| 40 | 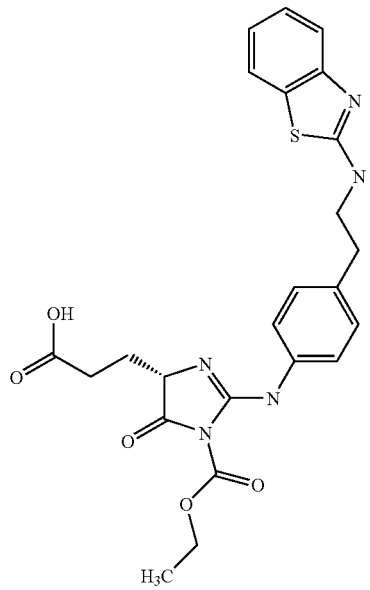 | C | 495 | 496.12 |
| 41 | 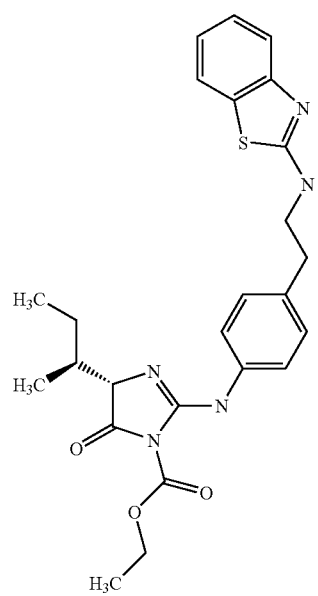 | C | 479 | 480.12 |

-continued
| Ex. No. | Structure | Ki | Exact Mass (g/mol) | Obs. Mass (M + 1) |
|---|---|---|---|---|
| 42 | 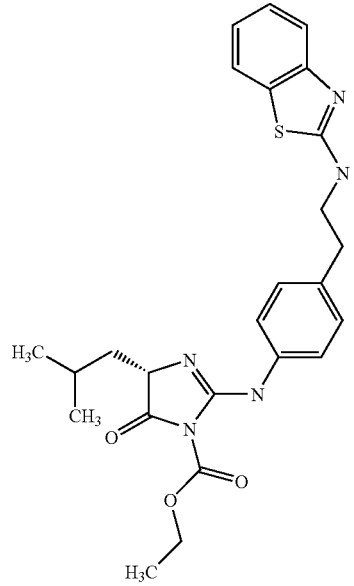 | | 479 | 480.12 |
| 43 | 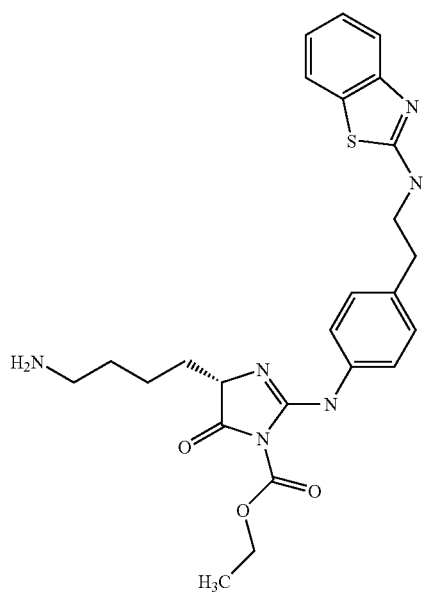 | | 494 | 495.12 |

-continued
| Ex. No. | Structure | Ki | Exact Mass (g/mol) | Obs. Mass (M + 1) |
|---|---|---|---|---|
| 44 | 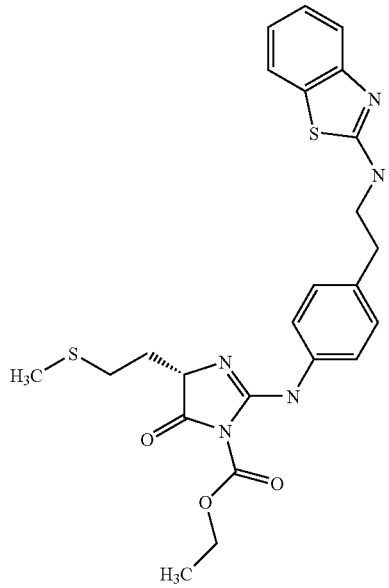 | | 497 | 498.12 |
| 45 | 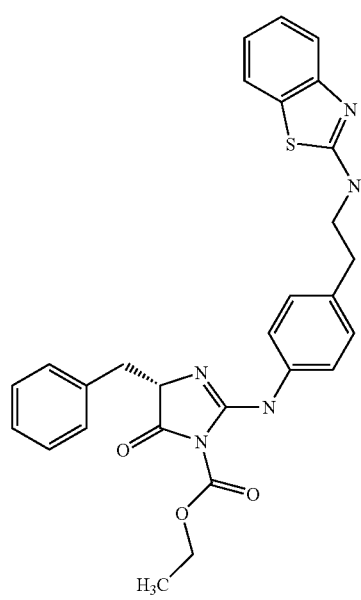 | | 513 | 514.12 |

-continued
| Ex. No. | Structure | Ki | Exact Mass (g/mol) | Obs. Mass (M + 1) |
|---|---|---|---|---|
| 46 | 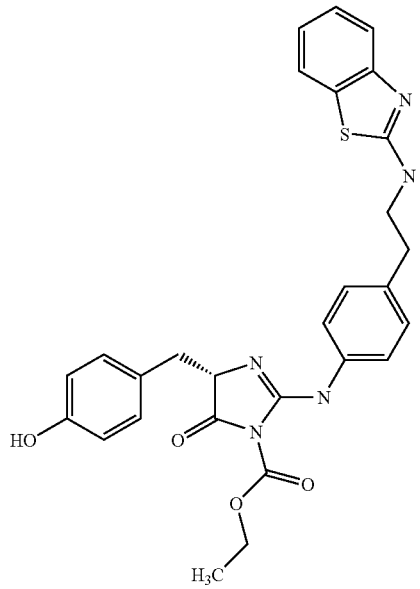 | | 529 | 530.13 |
| 47 | 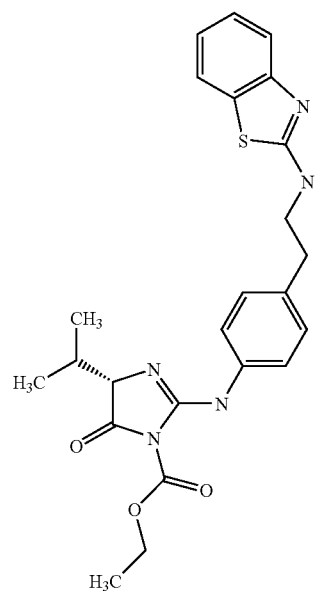 | | 465 | 466.11 |

-continued
| Ex. No. | Structure | Ki | Exact Mass (g/mol) | Obs. Mass (M + 1) |
|---|---|---|---|---|
| 48 | 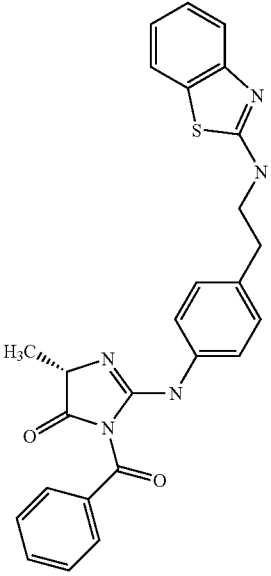 | | 469 | 470.11 |
| 49 | 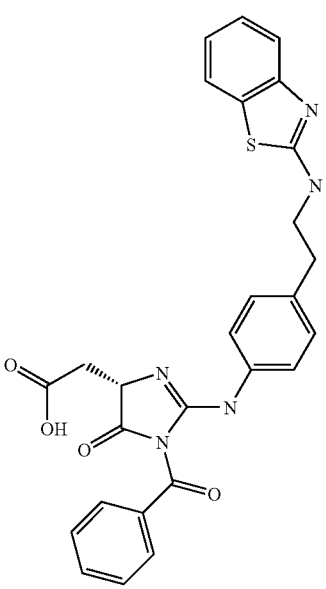 | C | 513 | 514.12 |

-continued
| Ex. No. | Structure | Ki | Exact Mass (g/mol) | Obs. Mass (M + 1) |
|---|---|---|---|---|
| 50 | 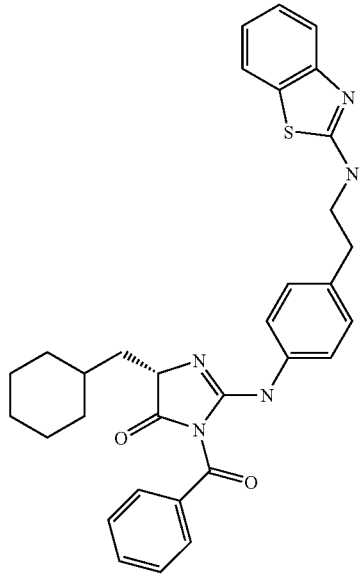 | C | 551 | 552.13 |
| 51 | 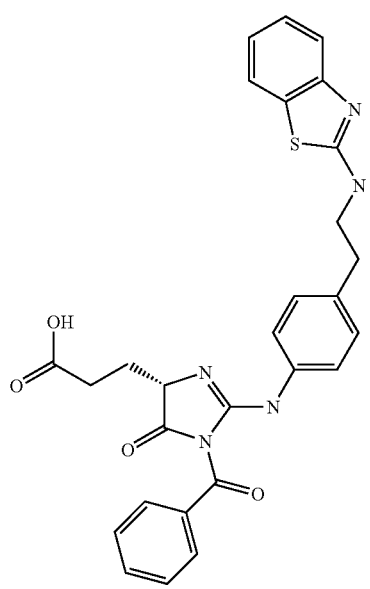 | C | 527 | 528.13 |

-continued

| Ex. No. | Structure | Ki | Exact Mass (g/mol) | Obs. Mass (M + 1) |
|---|---|---|---|---|
| 52 | 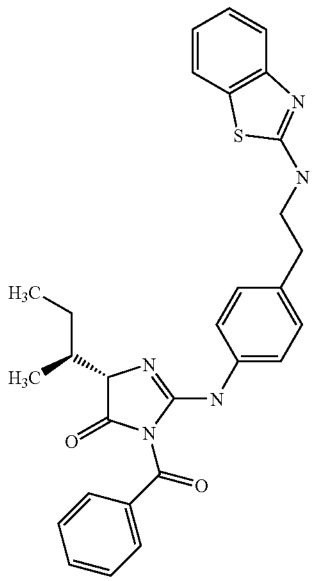 | C | 511 | 512.12 |
| 53 | 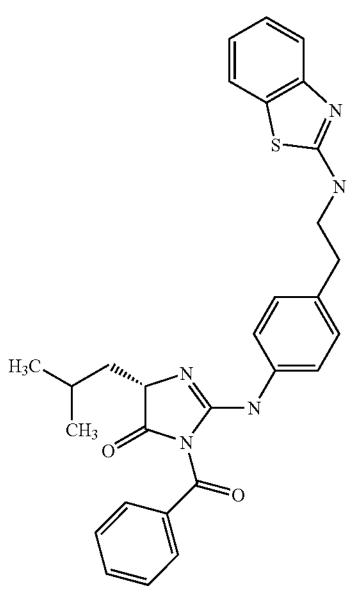 | C | 511 | 512.12 |

-continued
| Ex. No. | Structure | Ki | Exact Mass (g/mol) | Obs. Mass (M + 1) |
|---|---|---|---|---|
| 54 | 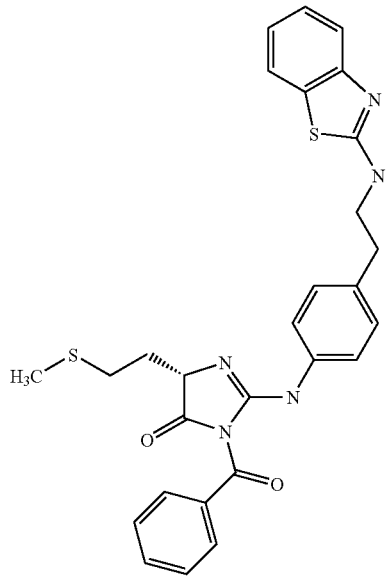 | C | 529 | 530.13 |
| 55 | 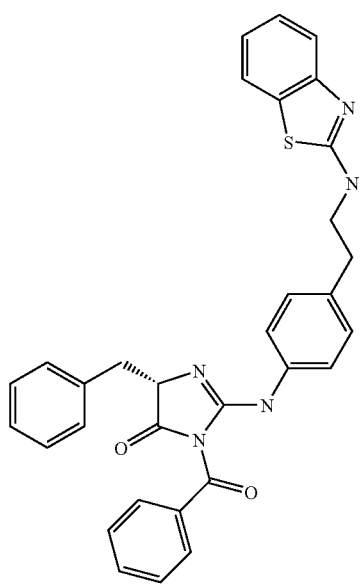 |  | 545 | 546.13 |

-continued
| Ex. No. | Structure | Ki | Exact Mass (g/mol) | Obs. Mass (M + 1) |
|---|---|---|---|---|
| 56 | 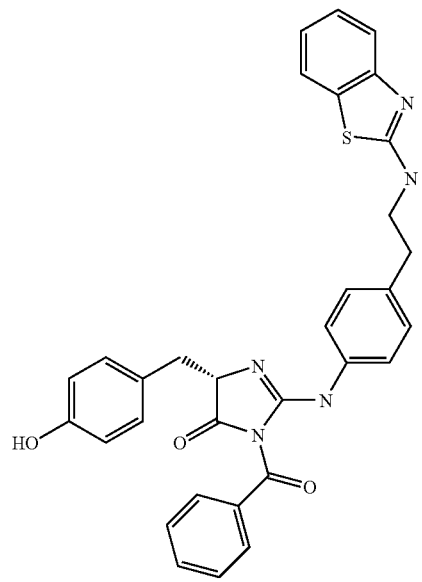 | | 561 | 562.13 |
| 57 | 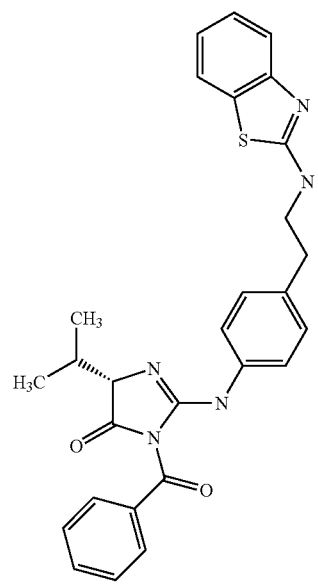 | | 497.6 | 498.12 |

-continued
| Ex. No. | Structure | Ki | Exact Mass (g/mol) | Obs. Mass (M + 1) |
|---|---|---|---|---|
| 58 | 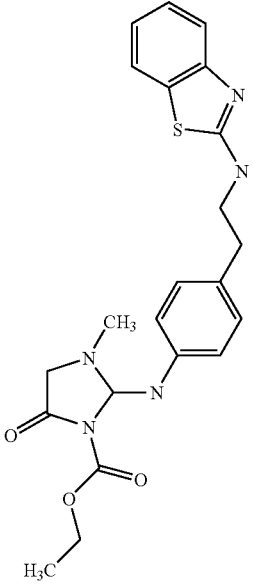 | | 437 | 438.11 |
| 59 | 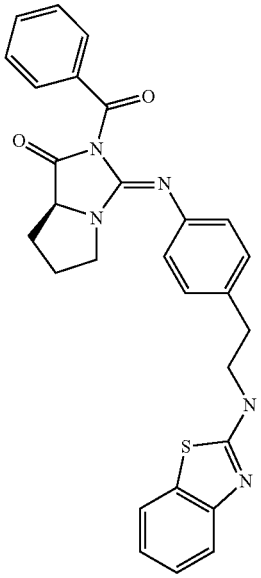 | | 495 | 496.12 |

-continued
| Ex. No. | Structure | Ki | Exact Mass (g/mol) | Obs. Mass (M + 1) |
|---|---|---|---|---|
| 60 | 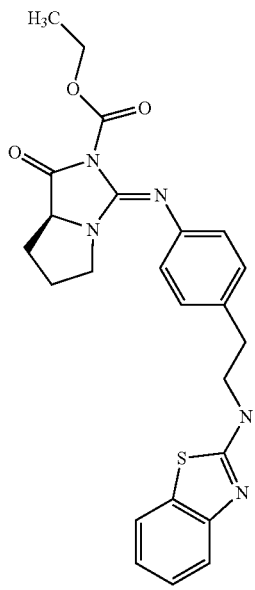 | | 463 | 464.11 |
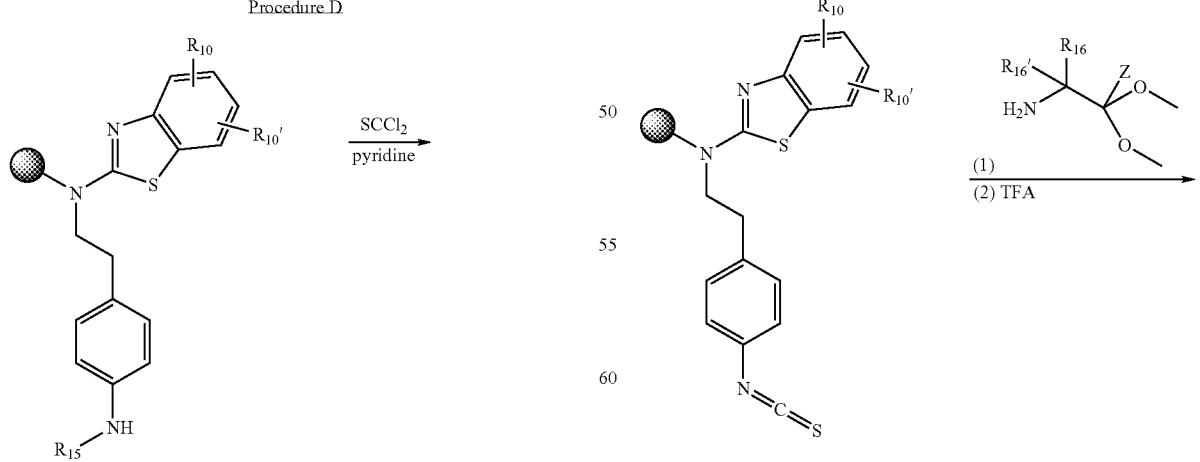

-continued

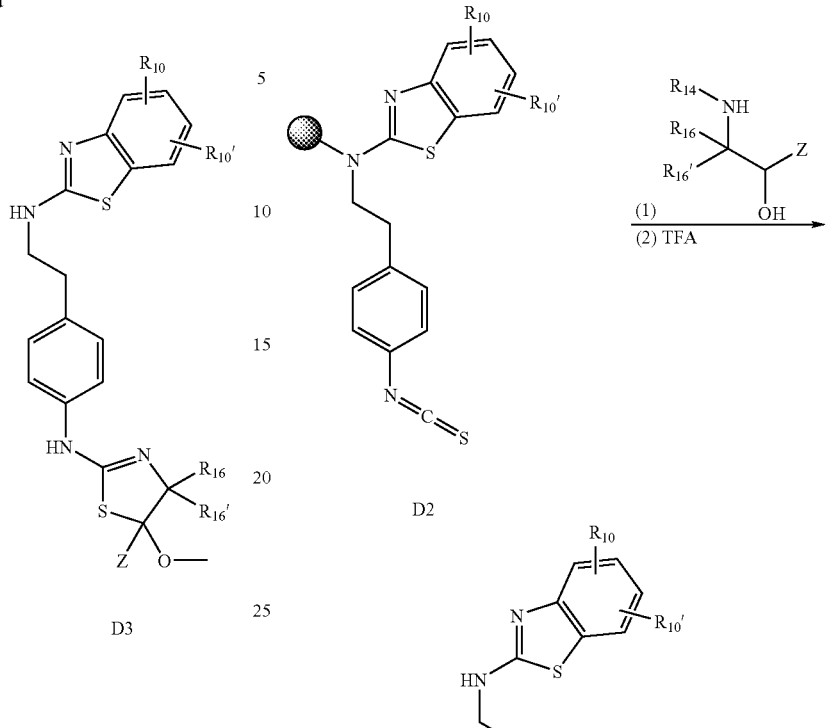

Procedure D, Step 1:

Anhydrous pyridine (0.35 mL, 4.45 mmol) was added to preswelled resin A3 ($R_{10}$ is H, $R_{10'}$ is H and $R_{15}$ is H) (500 mg) suspended in DCM (2 mL). Thiophosgene (0.1 mL, 1.34 mmol) was added and the reaction was shaken for 2 h. The resin was washed with anhydrous DCM and dried to yield D2 ($R_{10}$ is H and $R_{10'}$ is H).

Procedure D, Step 2:

Aminoacetaldehyde dimethyl acetal (1 mL, 9.2 mmol) was added to resin D2 ($R_{10}$ is H and $R_{10'}$ is H) (250 mg) suspended in DCM (2 mL). The reaction was agitated at RT. The resin was cleaved with 30% TFA in DCM. The filtrate was filtered through a plug of silicia gel and concentrated to yield D3 ($R_{10}$ is H, $R_{10'}$ is H, $R_{16}$ is H, $R_{16'}$ is H, and Z is H).

| Ex. No. | Structure | Ki | Exact Mass (g/mol) | Observed Mass (M + 1) |
|---|---|---|---|---|
| 61 | 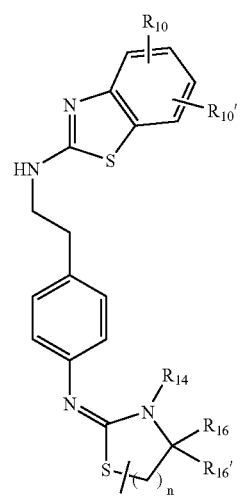 | B | 384 | 385.1 |

Procedure E, Step 1:

2-Amino-1-phenylethanol (100 mg) was added to pre-swelled resin D2 ($R_{10}$ is H and $R_{10'}$ is H) (60 mg) in DCM and shaken overnight at RT. The resin was washed with DCM (4×), THF (4×), and DCM (4×). The resin was cleaved with 20% TFA in DCM for 2 h. The filtrate was evaporated and the resulting material was treated with 100% TFA overnight. The solution was evaporated and the material was treated once again with 100% TFA overnight. If the compound(s) was still not cyclized, then the compound(s) was heated with 100% TFA at 70 to 80° C. overnight. The solution was concentrated to afford the product E2 ($R_{10}$ is H, $R_{10'}$ is H, $R_{14}$ is H, $R_{16}$ is H, $R_{16'}$ is H, Z is phenyl, and n is 2).

The following compounds were prepared using analogous methods:

| Ex. No. | Structure | Ki | Exact Mass (g/mol) | Obs. Mass (M + 1) |
|---|---|---|---|---|
| 62 | 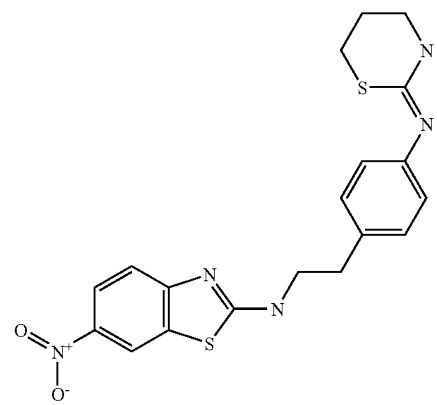 | C | 413 | 414.1 |
| 63 | 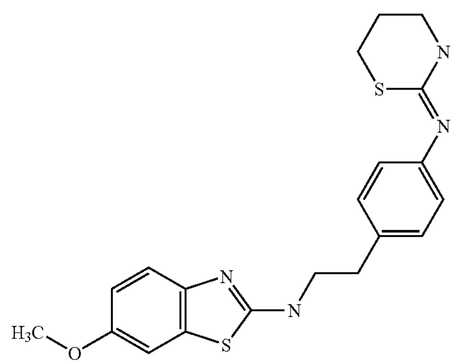 | B | 398 | 399.10 |
| 64 | 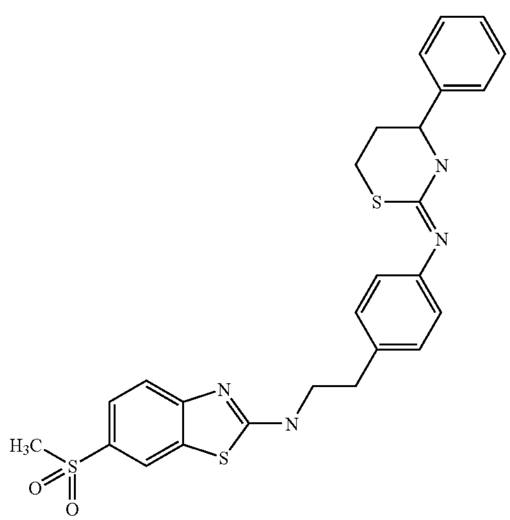 | B | 522 | 523.12 |

-continued

| Ex. No. | Structure | Ki | Exact Mass (g/mol) | Obs. Mass (M + 1) |
|---|---|---|---|---|
| 65 | 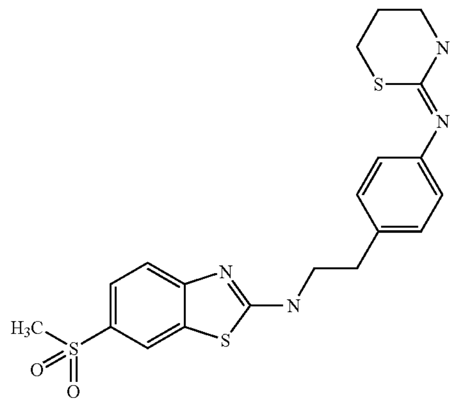 | B | 446 | 447.11 |
| 66 | 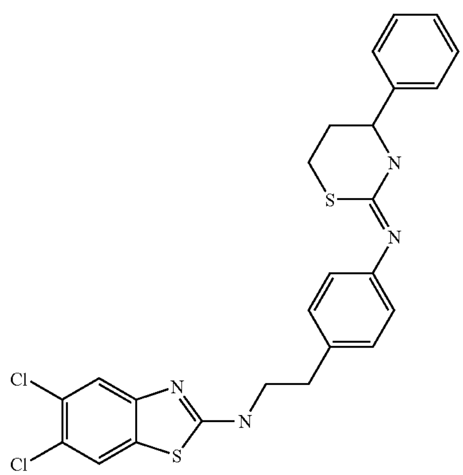 | C | 512 | 513.12 |
| 67 | 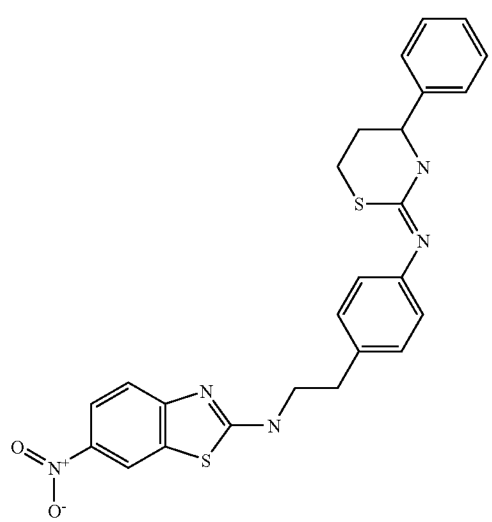 | C | 489 | 490.12 |

| Ex. No. | Structure | Ki | Exact Mass (g/mol) | Obs. Mass (M + 1) |
|---|---|---|---|---|
| 68 | 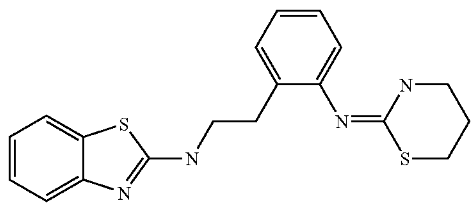 | C | 368 | 369.09 |
| 69 | 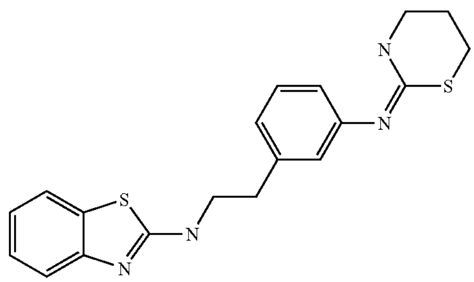 | C | 368 | 369.09 |
| 70 | 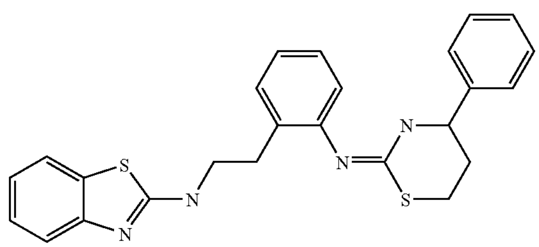 | C | 444 | 445.11 |
| 71 | 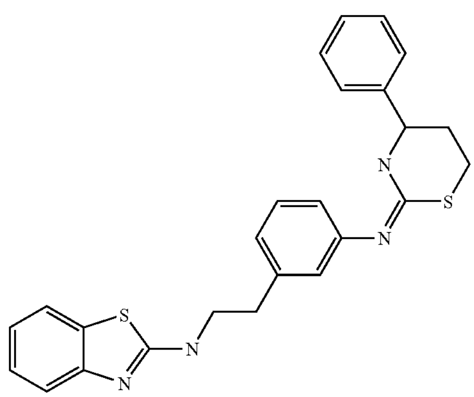 | C | 444 | 445.11 |
| 72 | 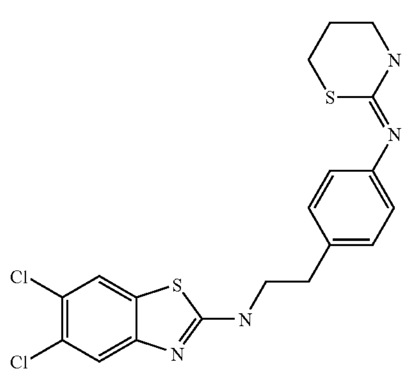 | A | 436 | 437.11 |

-continued

| Ex. No. | Structure | Ki | Exact Mass (g/mol) | Obs. Mass (M + 1) |
|---|---|---|---|---|
| 73 | 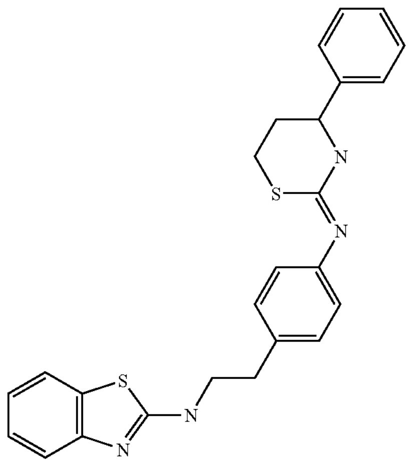 | A | 444 | 445.11 |
| 74 | 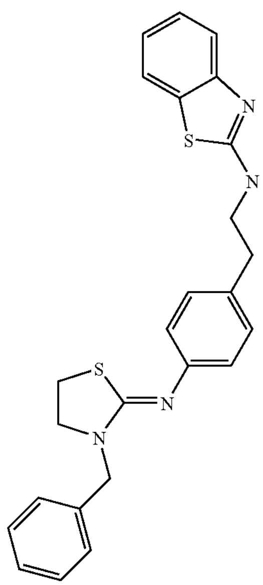 | C | 444 | 445.11 |
| 75 | 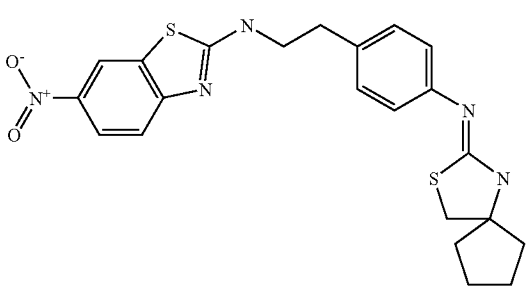 | B | 453 | 454.11 |

-continued

| Ex. No. | Structure | Ki | Exact Mass (g/mol) | Obs. Mass (M + 1) |
|---|---|---|---|---|
| 76 | 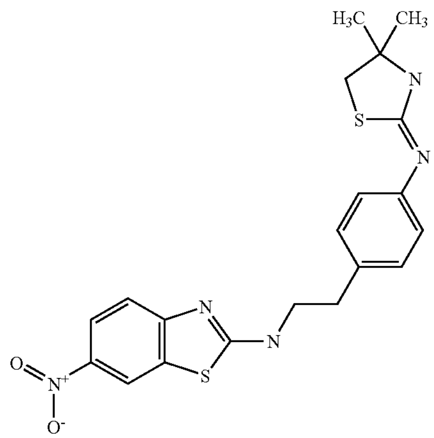 | C | 427 | 428.1 |
| 77 | 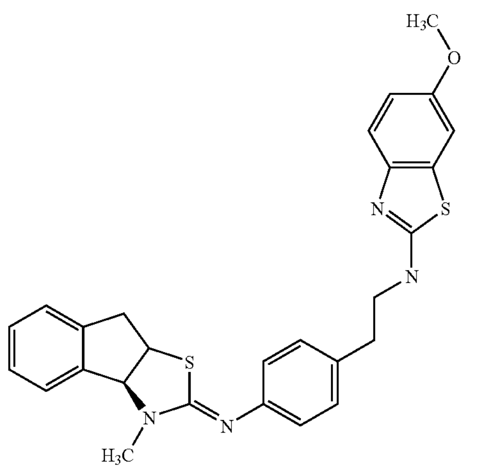 | C | 486 | 487.12 |
| 78 | 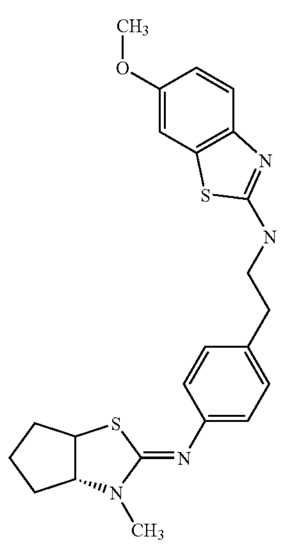 | C | 438 | 439.11 |

-continued
| Ex. No. | Structure | Ki | Exact Mass (g/mol) | Obs. Mass (M + 1) |
|---|---|---|---|---|
| 79 | 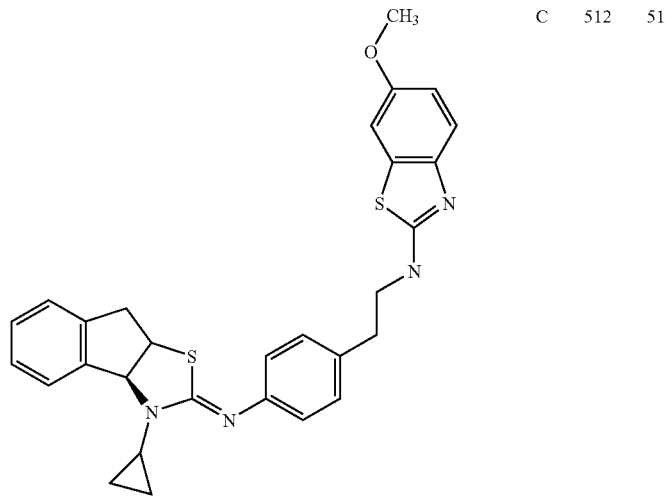 | C | 512 | 513.12 |
| 80 | 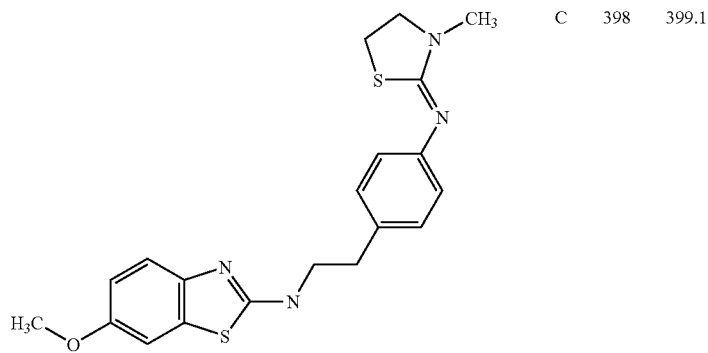 | C | 398 | 399.1 |
| 81 | 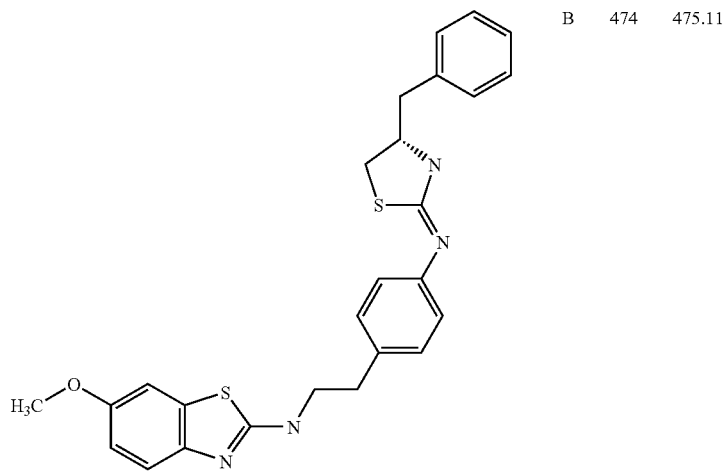 | B | 474 | 475.11 |

-continued
| Ex. No. | Structure | Ki | Exact Mass (g/mol) | Obs. Mass (M + 1) |
|---|---|---|---|---|
| 82 | 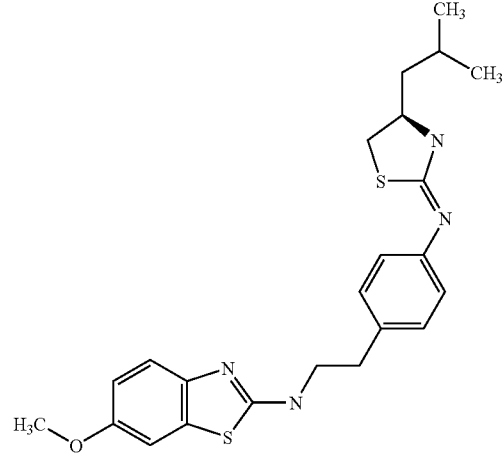 | A | 440 | 441.11 |
| 83 | 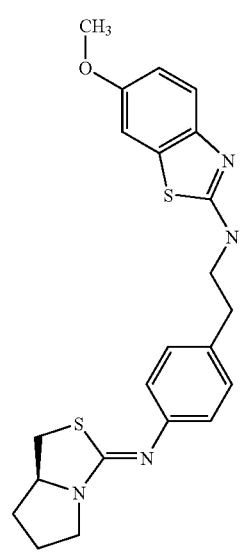 | C | 424 | 425.1 |
| 84 | 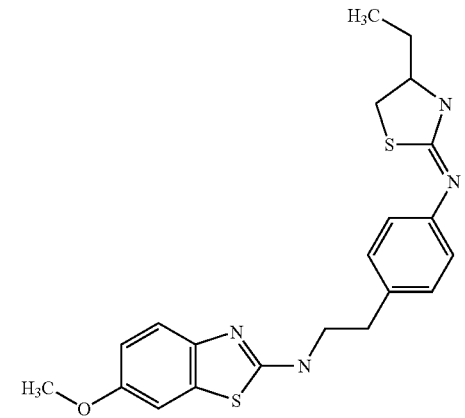 | A | 412 | 413.1 |

| Ex. No. | Structure | Ki | Exact Mass (g/mol) | Obs. Mass (M + 1) |
|---|---|---|---|---|
| 85 | 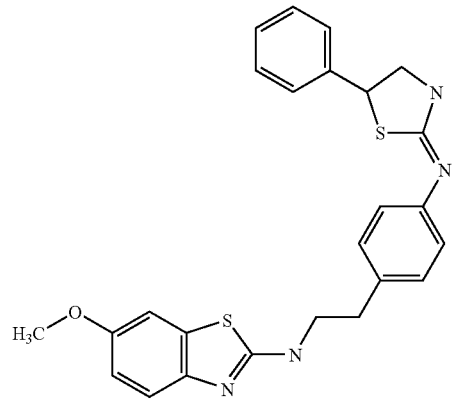 | C | 460 | 461.11 |
| 86 | 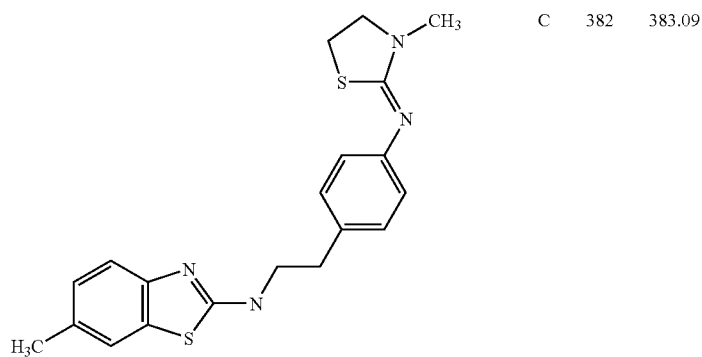 | C | 382 | 383.09 |
| 87 | 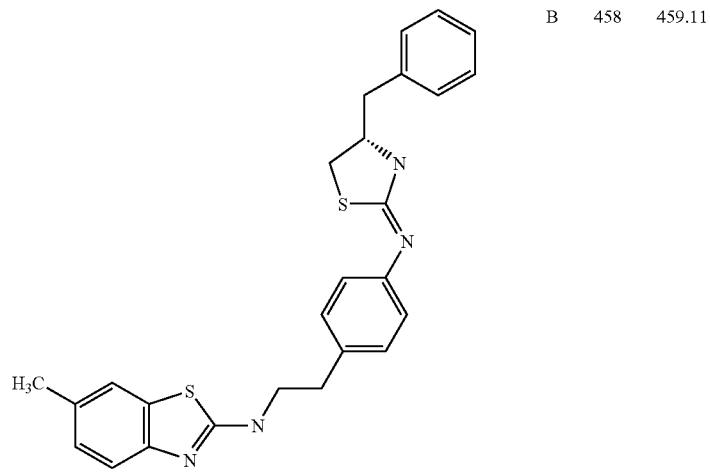 | B | 458 | 459.11 |

-continued

| Ex. No. | Structure | Ki | Exact Mass (g/mol) | Obs. Mass (M + 1) |
|---|---|---|---|---|
| 88 | 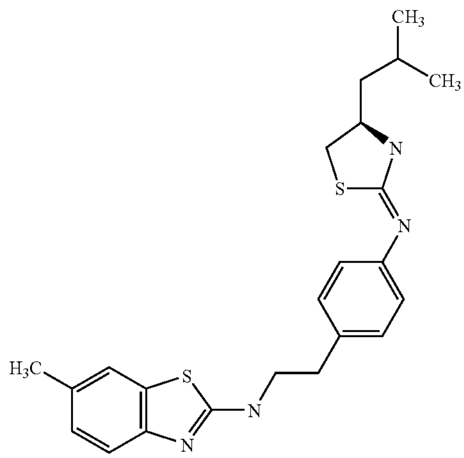 | A | 424 | 425.10 |
| 89 | 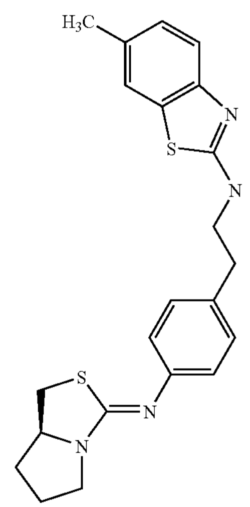 | C | 408 | 409.10 |
| 90 | 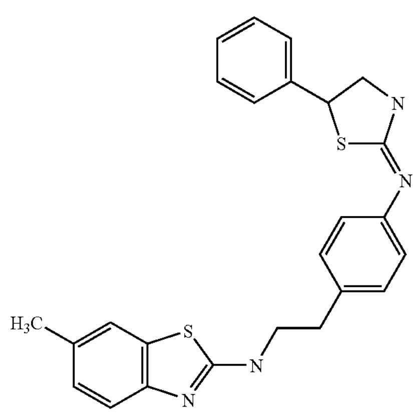 | C | 444 | 445.11 |

-continued
| Ex. No. | Structure | Ki | Exact Mass (g/mol) | Obs. Mass (M + 1) |
|---|---|---|---|---|
| 91 | 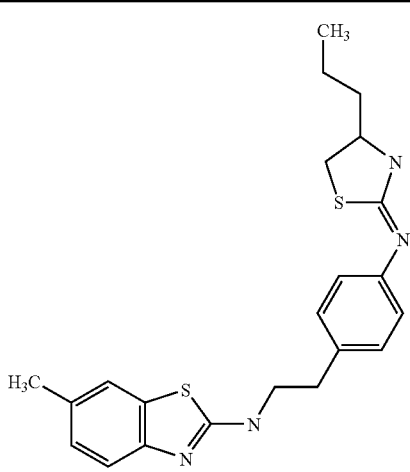 | A | 410 | 411.10 |
| 92 | 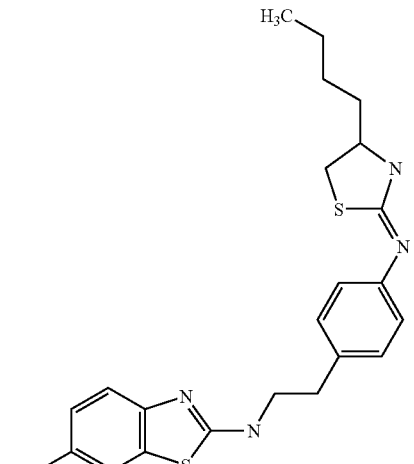 | B | 424 | 425.10 |
| 93 | 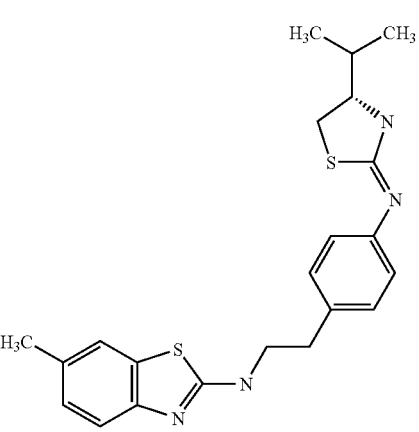 | B | 410 | 411.10 |

-continued
| Ex. No. | Structure | Ki | Exact Mass (g/mol) | Obs. Mass (M + 1) |
|---|---|---|---|---|
| 94 | 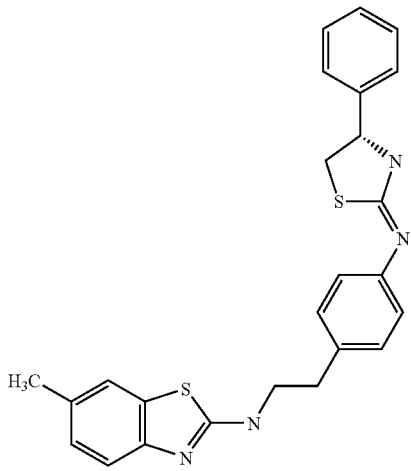 | | 444 | 445.11 |
| 95 | 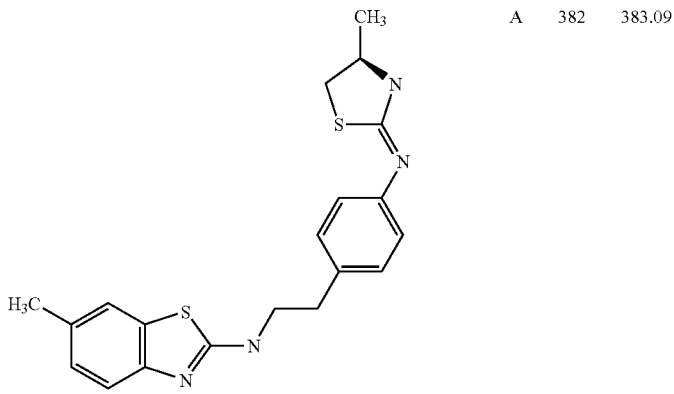 | A | 382 | 383.09 |
| 96 | 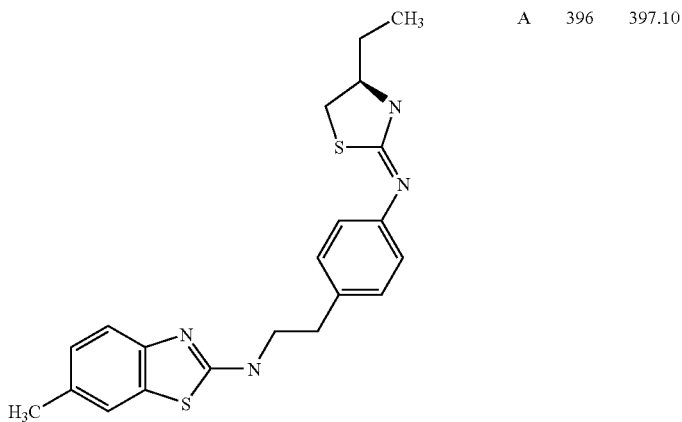 | A | 396 | 397.10 |

-continued

| Ex. No. | Structure | Ki | Exact Mass (g/mol) | Obs. Mass (M + 1) |
|---|---|---|---|---|
| 97 | 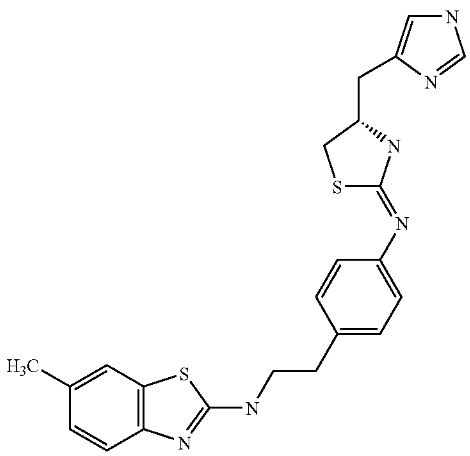 | B | 448 | 449.11 |
| 99 | 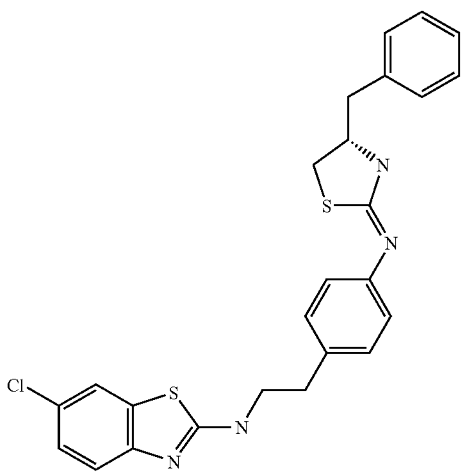 | | 478 | 479.11 |
| 100 | 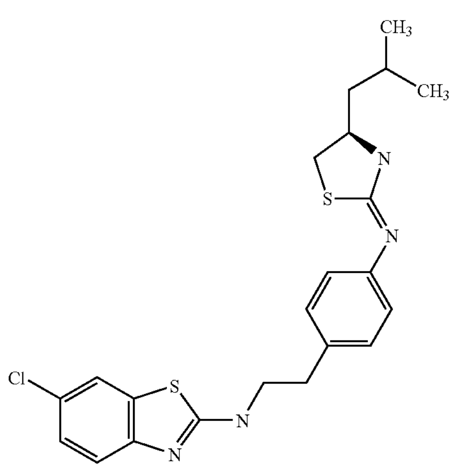 | B | 444 | 445.11 |

-continued

| Ex. No. | Structure | Ki | Exact Mass (g/mol) | Obs. Mass (M + 1) |
|---|---|---|---|---|
| 101 | 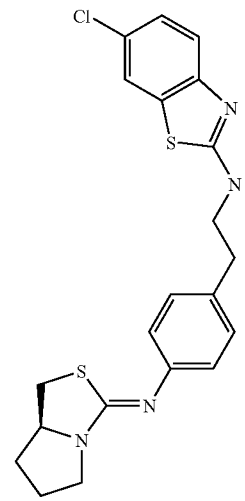 | | 428 | 429.10 |
| 102 | 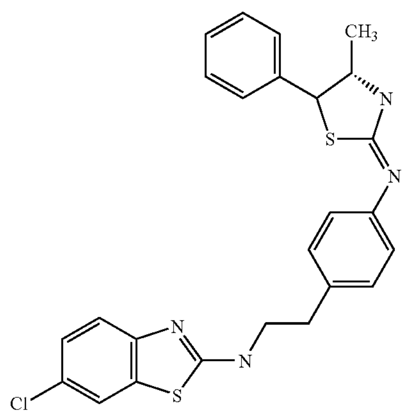 | | 478 | 479.11 |
| 103 | 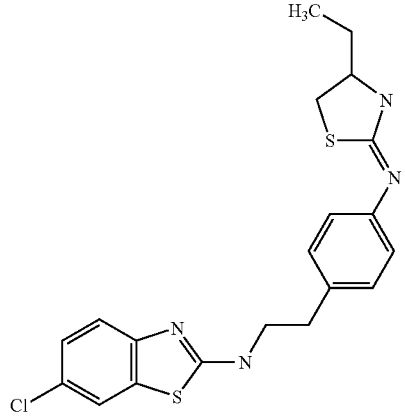 | B | 416 | 417.10 |

-continued
| Ex. No. | Structure | Ki | Exact Mass (g/mol) | Obs. Mass (M + 1) |
|---|---|---|---|---|
| 104 | 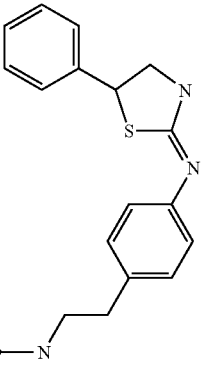 | | 464 | 465.11 |
| 105 | 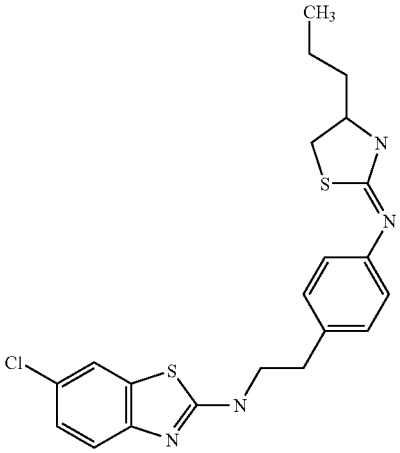 | A | 430 | 431.10 |
| 106 | 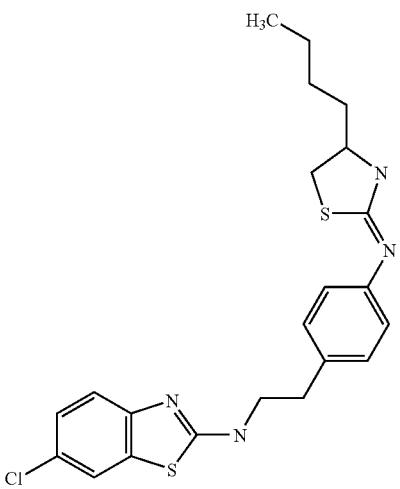 | B | 444 | 445.11 |

-continued

| Ex. No. | Structure | Ki | Exact Mass (g/mol) | Obs. Mass (M + 1) |
|---|---|---|---|---|
| 107 | 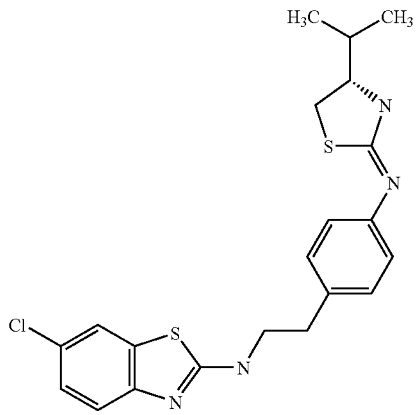 | B | 430 | 431.10 |
| 108 | 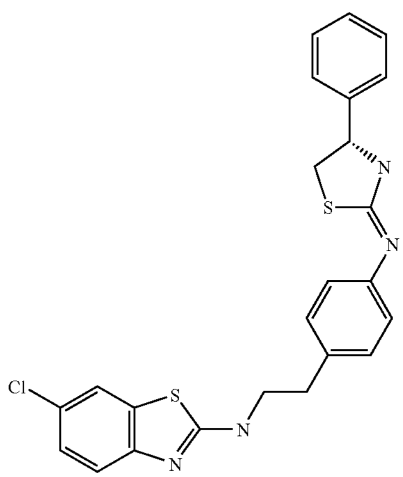 | | 464 | 465.11 |
| 109 | 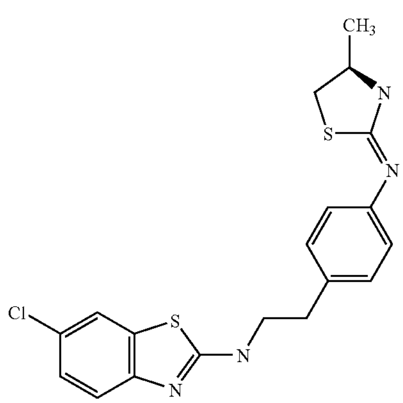 | B | 402 | 403.10 |

-continued

| Ex. No. | Structure | Ki | Exact Mass (g/mol) | Obs. Mass (M + 1) |
|---------|-----------|----|--------------------|--------------------|
| 110 | 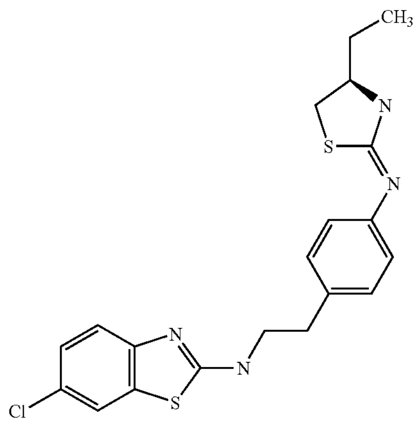 | A | 416 | 417.10 |
| 111 | 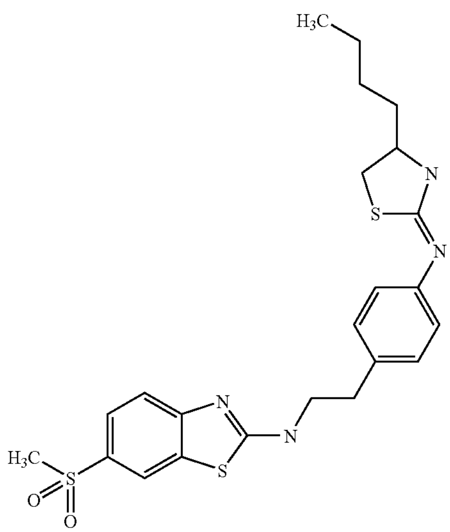 | B | 488 | 489.12 |
| 112 | 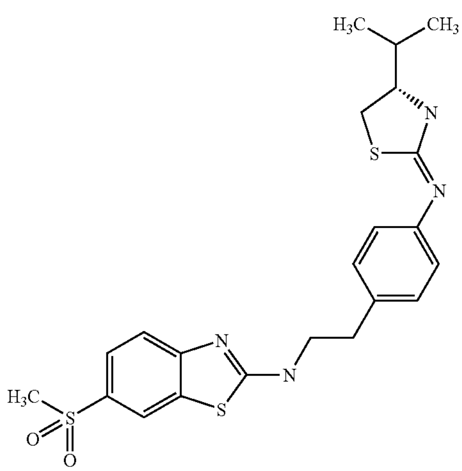 | | 474 | 475.11 |

-continued

| Ex. No. | Structure | Ki | Exact Mass (g/mol) | Obs. Mass (M + 1) |
|---|---|---|---|---|
| 113 | 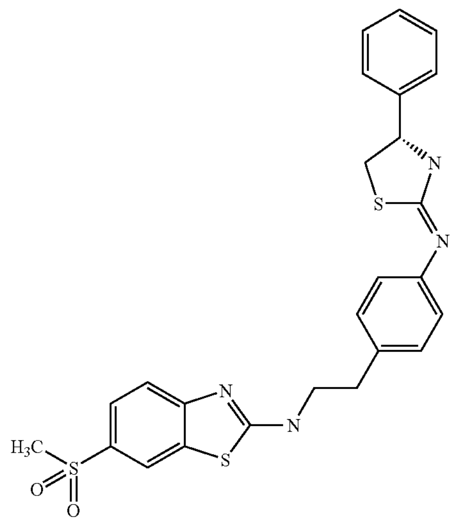 | | 508 | 509.12 |
| 114 | 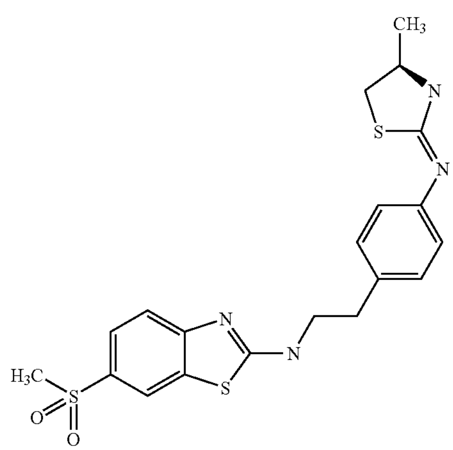 | B | 446 | 447.11 |
| 115 | 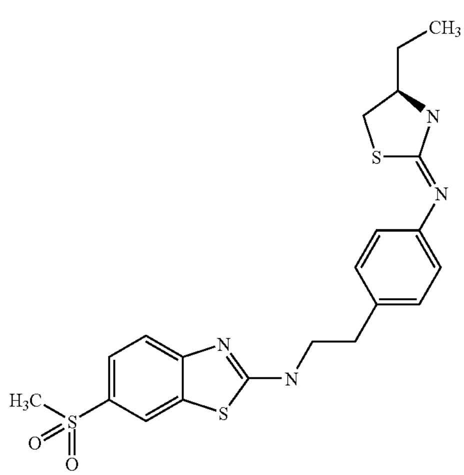 | B | 460 | 461.11 |

-continued

| Ex. No. | Structure | Ki | Exact Mass (g/mol) | Obs. Mass (M + 1) |
|---|---|---|---|---|
| 116 | 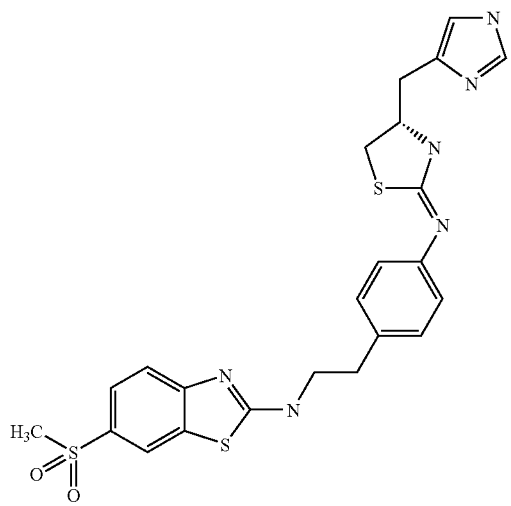 | B | 512 | 513.12 |
| 117 | 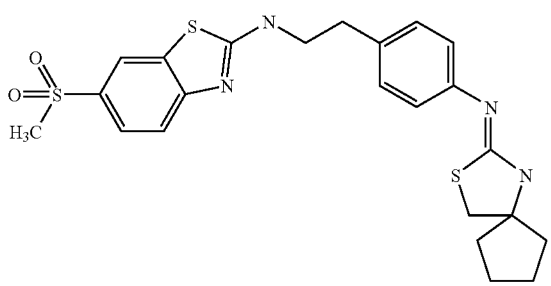 | B | 486 | 487.12 |
| 118 | 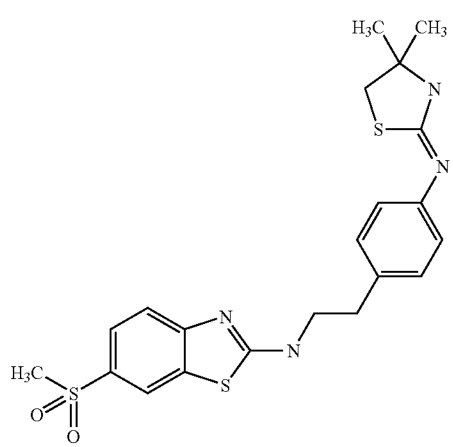 | B | 460 | 461.11 |

-continued

| Ex. No. | Structure | Ki | Exact Mass (g/mol) | Obs. Mass (M + 1) |
|---|---|---|---|---|
| 119 | 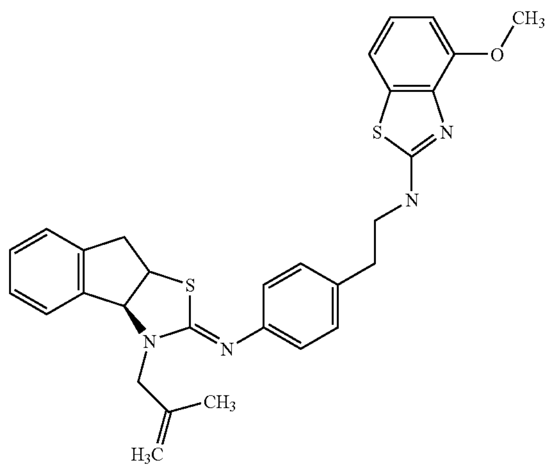 | | 526 | 527.13 |
| 120 | 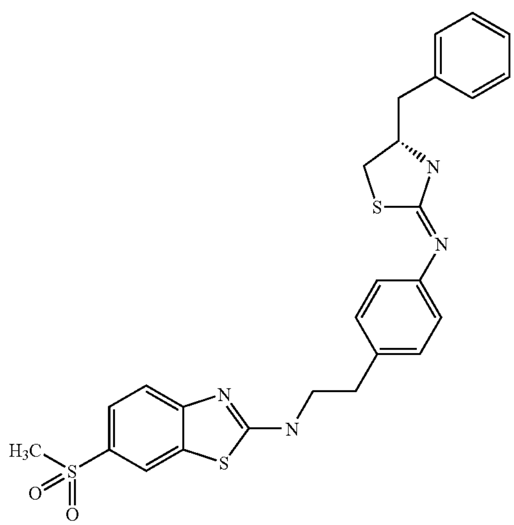 | | 522 | 523.12 |
| 121 | 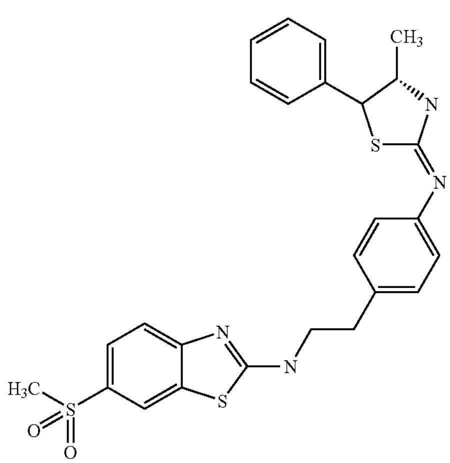 | | 522 | 523.12 |

-continued

| Ex. No. | Structure | Ki | Exact Mass (g/mol) | Obs. Mass (M + 1) |
|---|---|---|---|---|
| 122 | 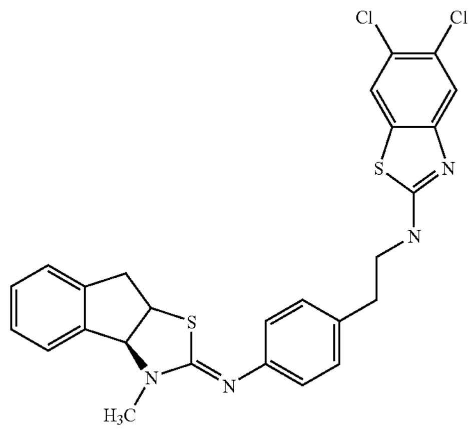 | | 524 | 525.1 |
| 123 | 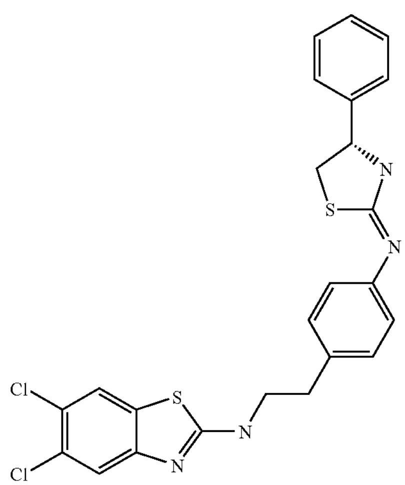 | | 498 | 499.1 |
| 124 | 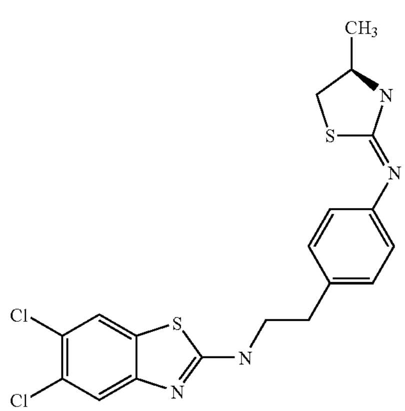 | | 436 | 437.11 |

-continued
| Ex. No. | Structure | Ki | Exact Mass (g/mol) | Obs. Mass (M + 1) |
|---|---|---|---|---|
| 125 | 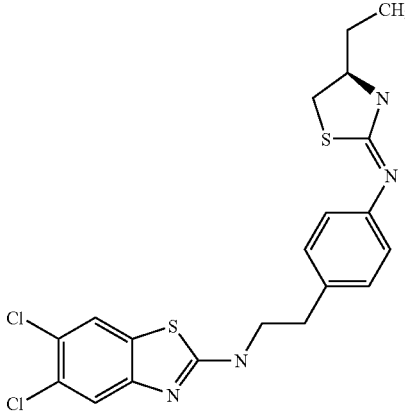 | | 450 | 451.11 |
| 126 | 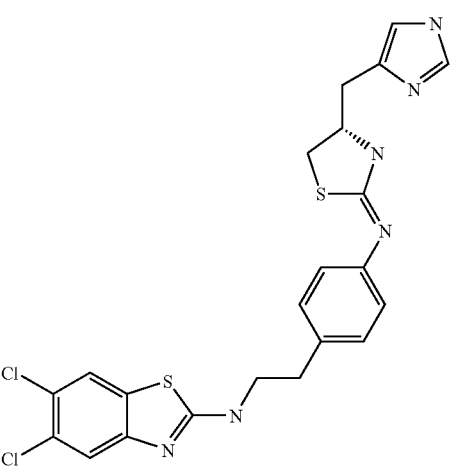 | | 502 | 503.12 |
| 127 | 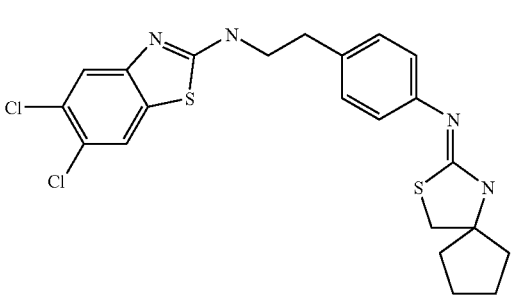 | | 476 | 477.11 |

-continued
| Ex. No. | Structure | Ki | Exact Mass (g/mol) | Obs. Mass (M + 1) |
|---|---|---|---|---|
| 128 | 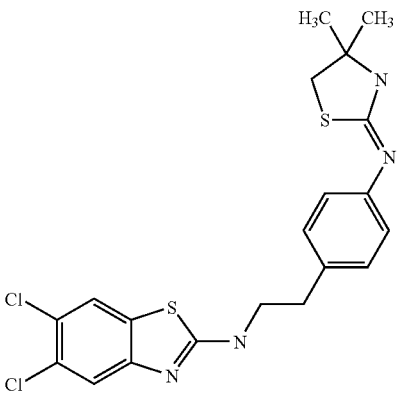 | | 450 | 451.11 |
| 129 | 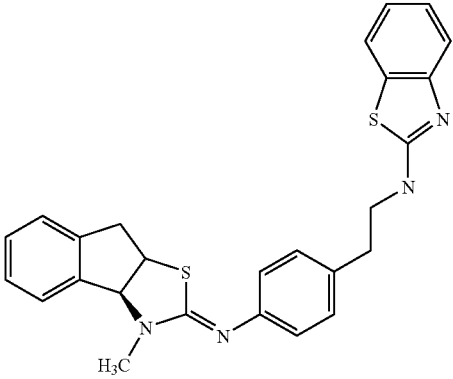 | | 456 | 457.11 |
| 130 | 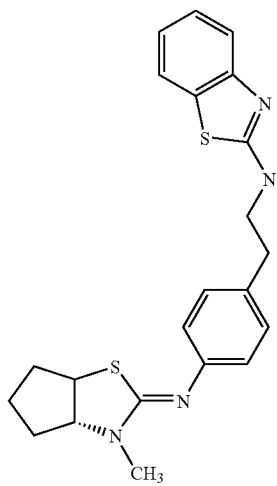 | | 408 | 409.10 |

| Ex. No. | Structure | Ki | Exact Mass (g/mol) | Obs. Mass (M + 1) |
|---|---|---|---|---|
| 131 | 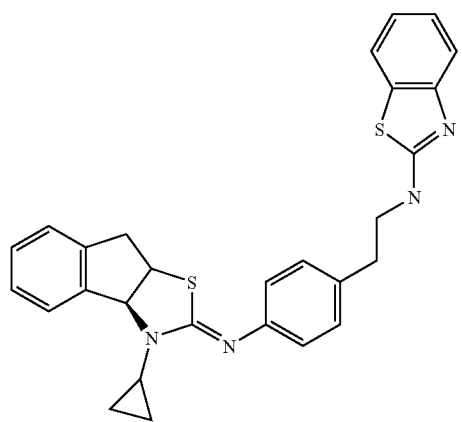 | | 482 | 483.12 |
| 132 | 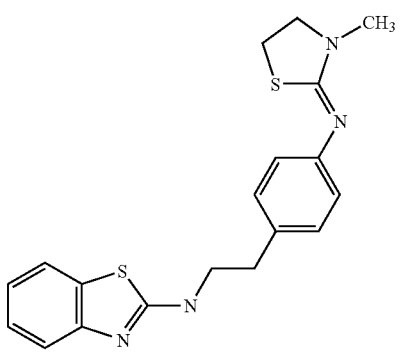 | | 368 | 369.09 |
| 133 | 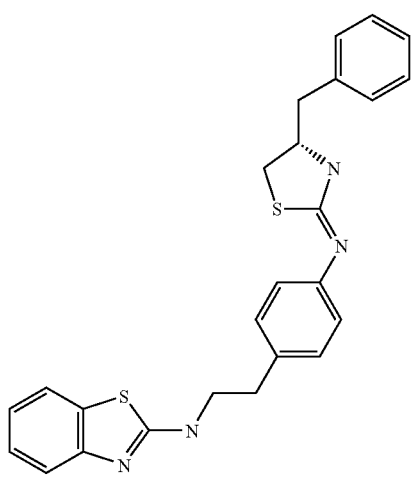 | | 444 | 445.11 |

-continued

| Ex. No. | Structure | Ki | Exact Mass (g/mol) | Obs. Mass (M + 1) |
|---|---|---|---|---|
| 134 | 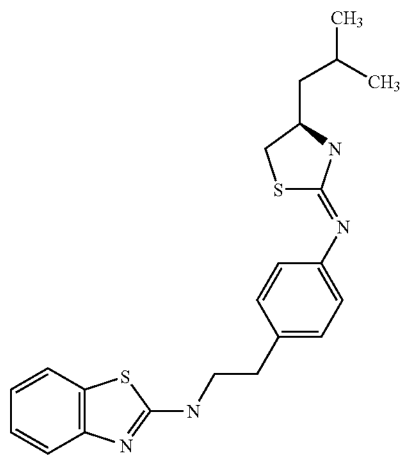 | A | 410 | 411.10 |
| 135 | 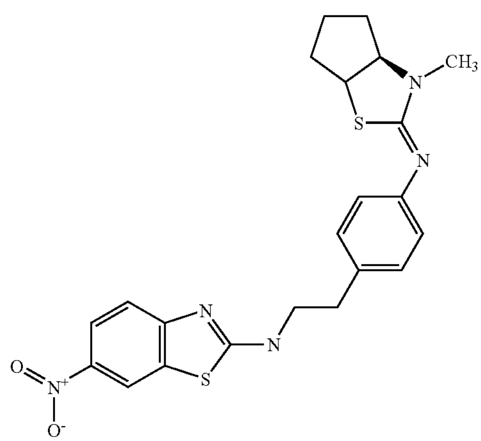 | | 453 | 454.11 |
| 136 | 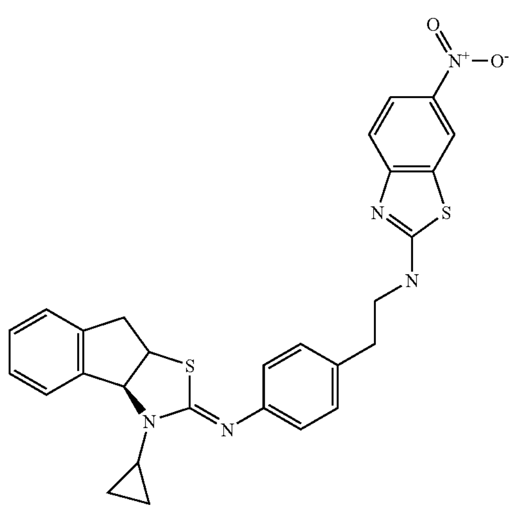 | | 527 | 528.13 |

-continued
| Ex. No. | Structure | Ki | Exact Mass (g/mol) | Obs. Mass (M + 1) |
|---|---|---|---|---|
| 137 | 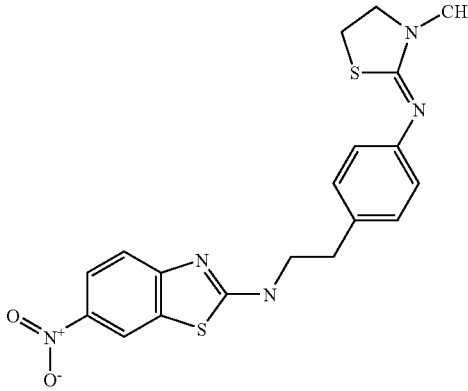 | | 413 | 414.10 |
| 138 | 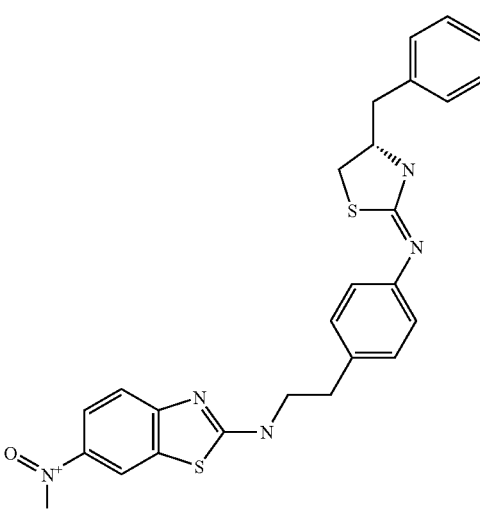 | | 489 | 490.12 |
| 139 | 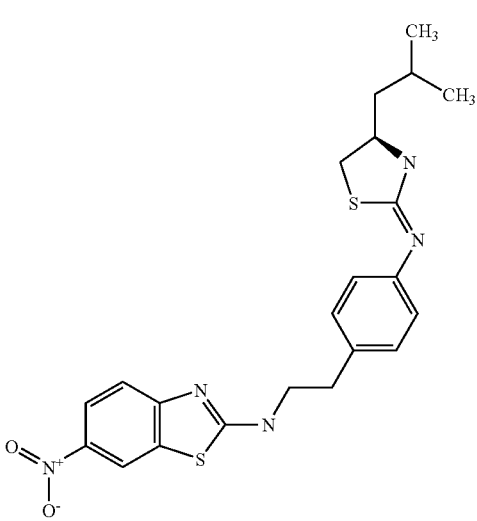 | | 455 | 456.11 |

-continued

| Ex. No. | Structure | Ki | Exact Mass (g/mol) | Obs. Mass (M + 1) |
|---|---|---|---|---|
| 140 | 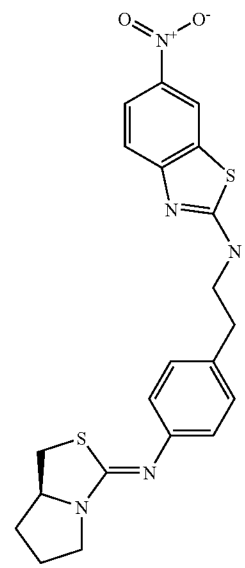 | | 439 | 440.11 |
| 141 | 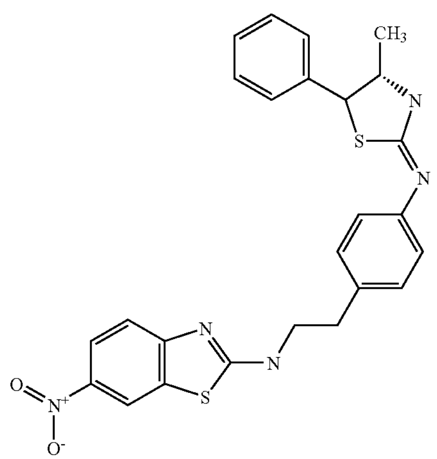 | | 489 | 490.12 |
| 142 | 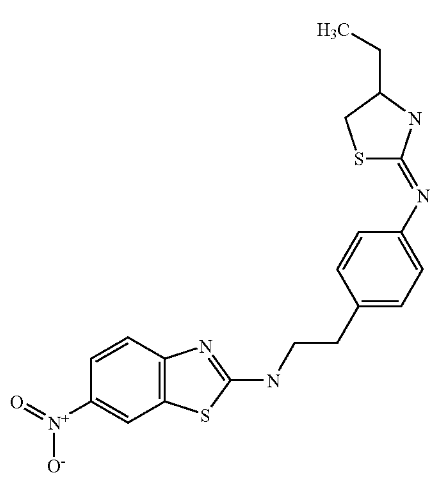 | | 427 | 428.10 |

-continued

| Ex. No. | Structure | Ki | Exact Mass (g/mol) | Obs. Mass (M + 1) |
|---|---|---|---|---|
| 143 | 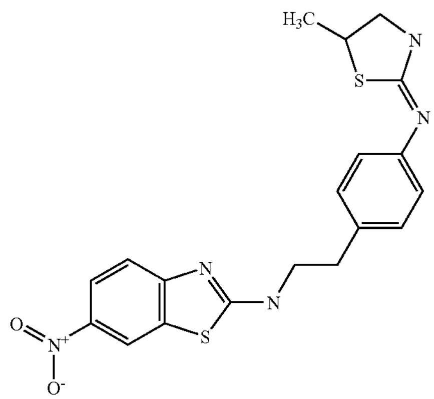 | | 413 | 414.10 |
| 144 | 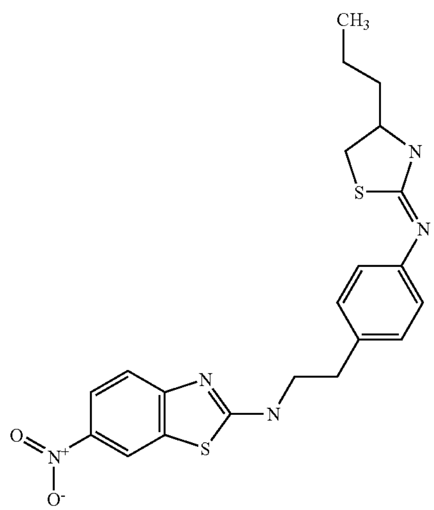 | | 441 | 442.11 |
| 145 | 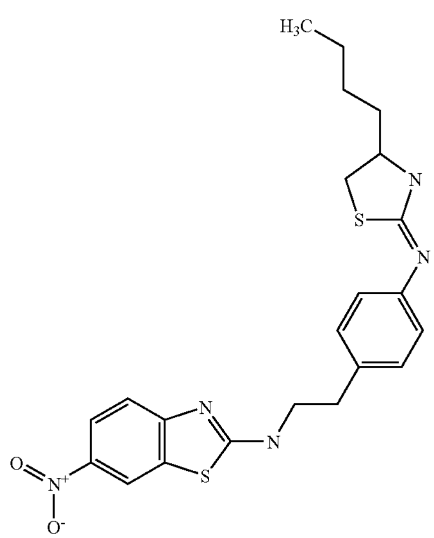 | | 455 | 456.11 |

-continued

| Ex. No. | Structure | Ki | Exact Mass (g/mol) | Obs. Mass (M + 1) |
|---|---|---|---|---|
| 146 | 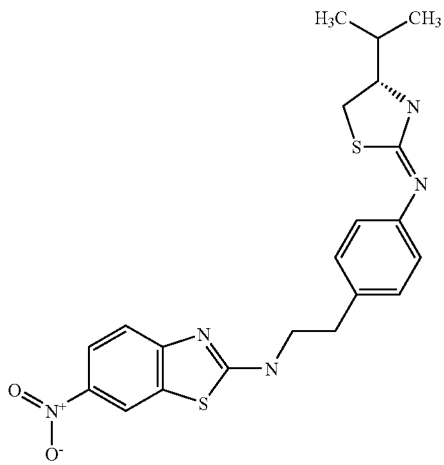 | | 441 | 442.11 |
| 147 | 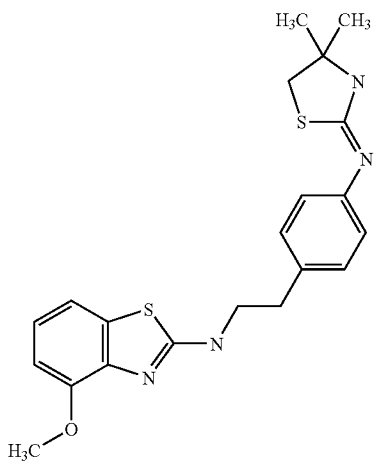 | | 412 | 413.1 |
| 148 | 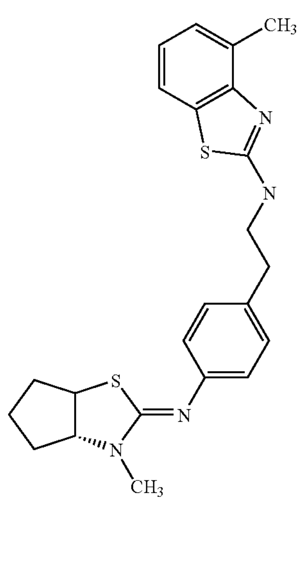 | | 422 | 423.1 |

-continued

| Ex. No. | Structure | Ki | Exact Mass (g/mol) | Obs. Mass (M + 1) |
|---|---|---|---|---|
| 149 | 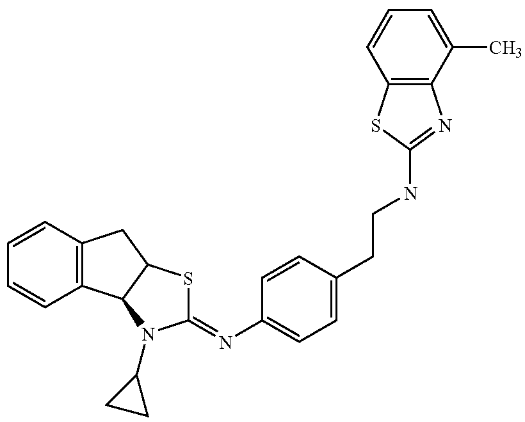 | | 496 | 497.12 |
| 150 | 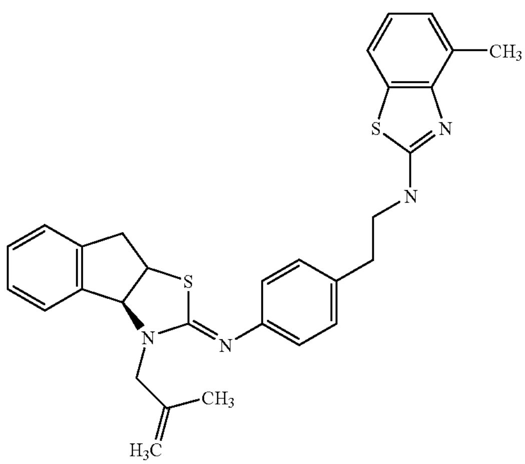 | | 510 | 511.12 |
| 151 | 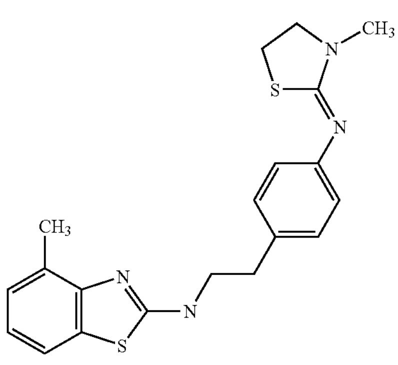 | | 382 | 383.09 |

-continued
| Ex. No. | Structure | Ki | Exact Mass (g/mol) | Obs. Mass (M + 1) |
|---|---|---|---|---|
| 152 | 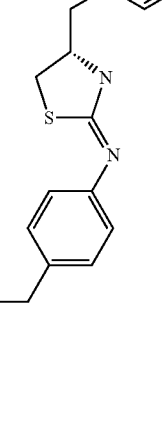 | | 458 | 459.11 |
| 153 | 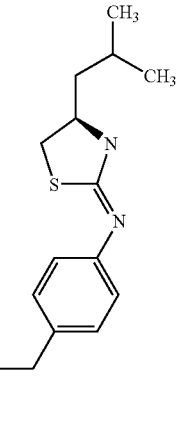 | | 424 | 425.1 |
| 154 | 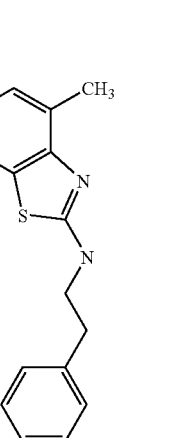 | | 408 | 409.1 |

-continued

| Ex. No. | Structure | Ki | Exact Mass (g/mol) | Obs. Mass (M + 1) |
|---|---|---|---|---|
| 155 | 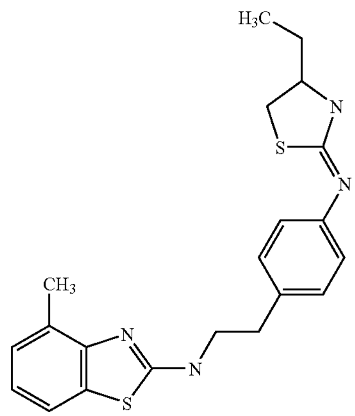 | | 396 | 397.1 |
| 156 | 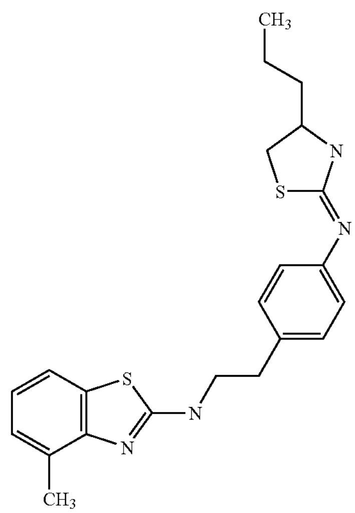 | | 410 | 411.1 |
| 157 | 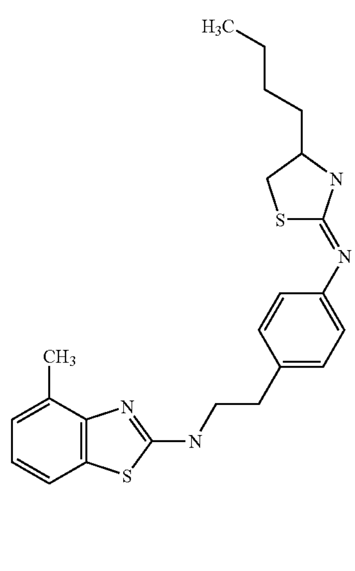 | | 424 | 425.1 |

-continued

| Ex. No. | Structure | Ki | Exact Mass (g/mol) | Obs. Mass (M + 1) |
|---|---|---|---|---|
| 158 | 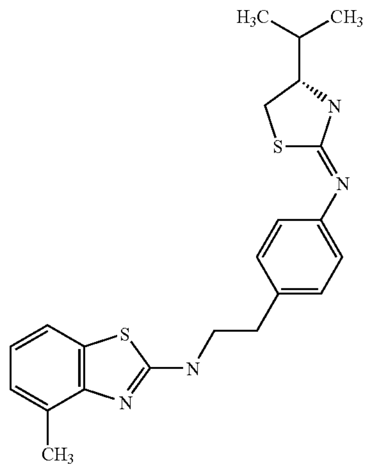 | | 410 | 411.1 |
| 159 | 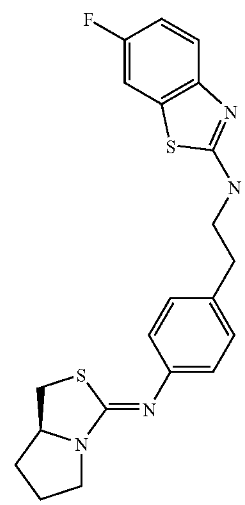 | | 412 | 413.10 |
| 160 | 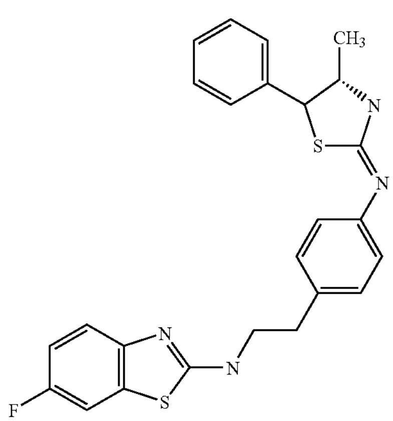 | | 462 | 463.11 |

-continued

| Ex. No. | Structure | Ki | Exact Mass (g/mol) | Obs. Mass (M + 1) |
|---|---|---|---|---|
| 161 | 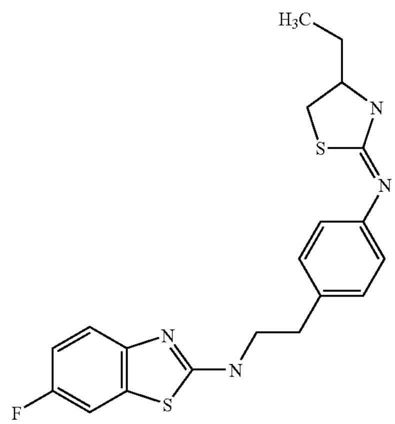 | | 400 | 401.10 |
| 162 | 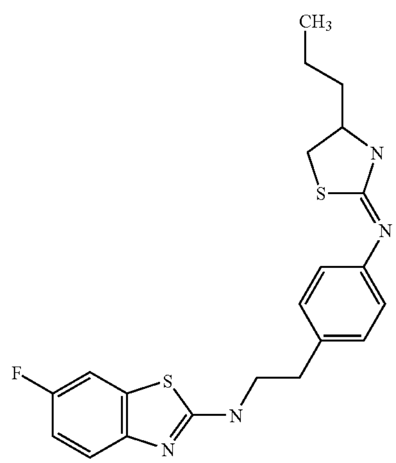 | | 414 | 415.10 |
| 163 | 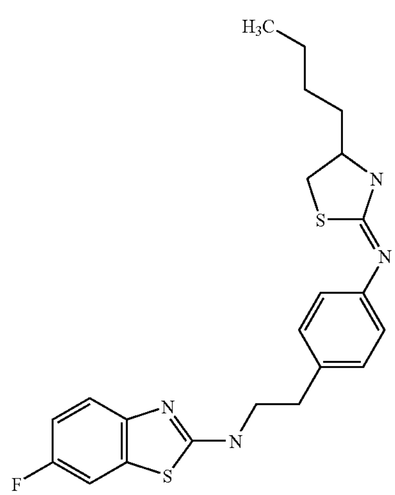 | | 428 | 429.10 |

-continued

| Ex. No. | Structure | Ki | Exact Mass (g/mol) | Obs. Mass (M + 1) |
|---|---|---|---|---|
| 164 | 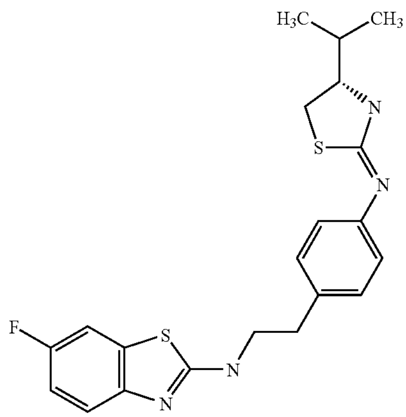 | | 414 | 415.10 |
| 165 | 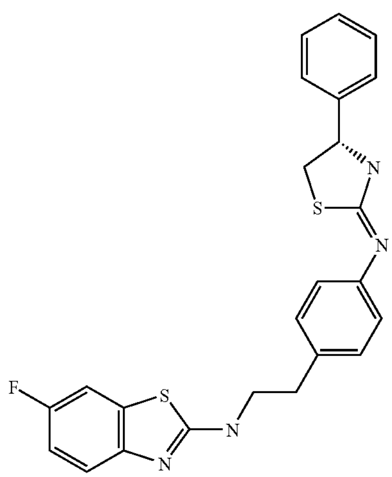 | | 448 | 449.11 |
| 166 | 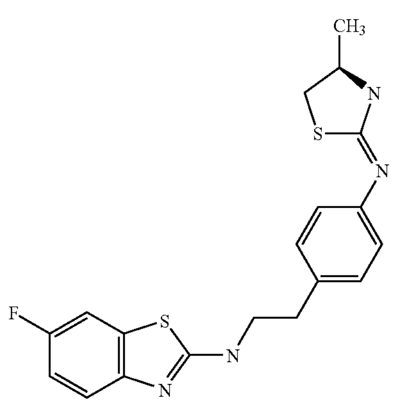 | | 386 | 387.10 |

-continued

| Ex. No. | Structure | Ki | Exact Mass (g/mol) | Obs. Mass (M + 1) |
|---|---|---|---|---|
| 167 | 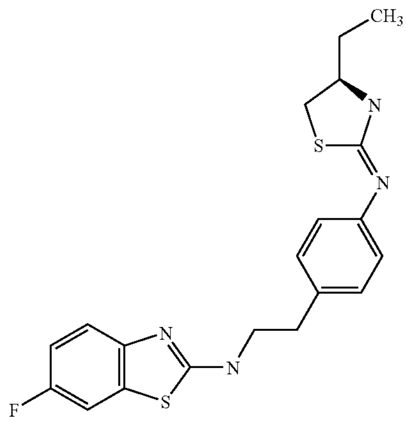 | A | 400 | 401.10 |
| 168 | 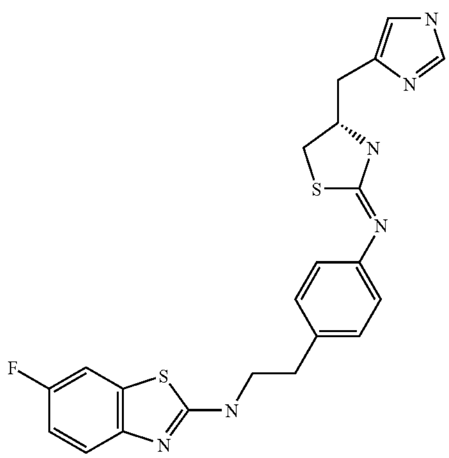 | | 452 | 453.11 |
| 169 | 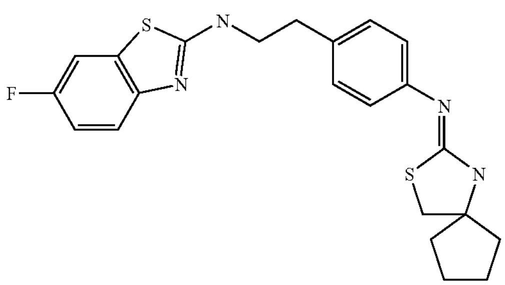 | A | 426 | 427.10 |
| 170 | 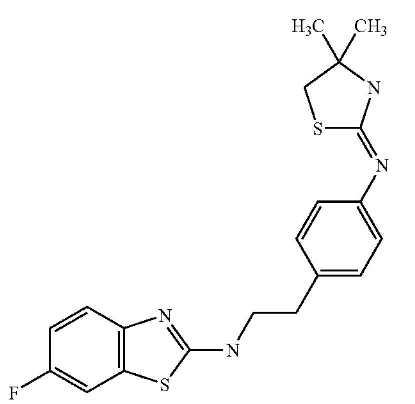 | | 400 | 401.10 |

-continued

| Ex. No. | Structure | Ki | Exact Mass (g/mol) | Obs. Mass (M + 1) |
|---|---|---|---|---|
| 171 | 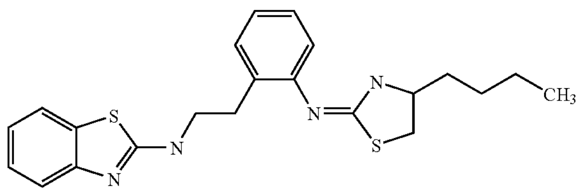 | | 410 | 411.10 |
| 172 | 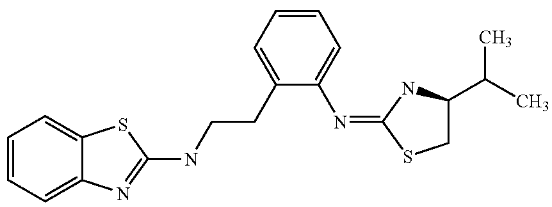 | | 396 | 397.10 |
| 173 | 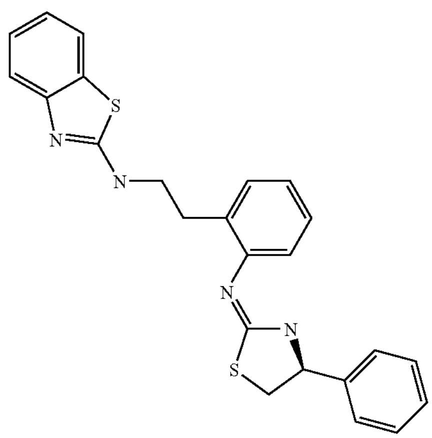 | | 430 | 431.10 |
| 174 | 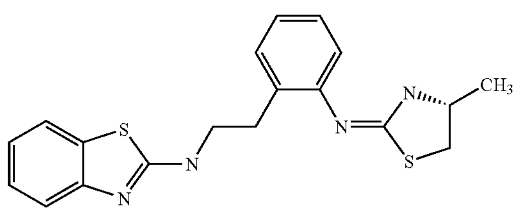 | | 368 | 369.09 |
| 175 | 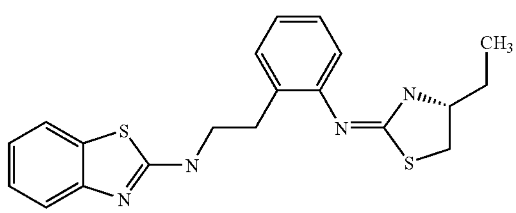 | | 382 | 383.09 |
| 176 | 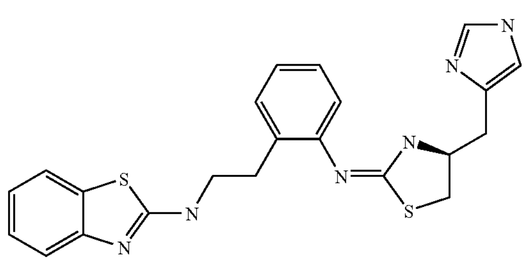 | | 434 | 435.11 |

-continued
| Ex. No. | Structure | Ki | Exact Mass (g/mol) | Obs. Mass (M + 1) |
|---|---|---|---|---|
| 177 | 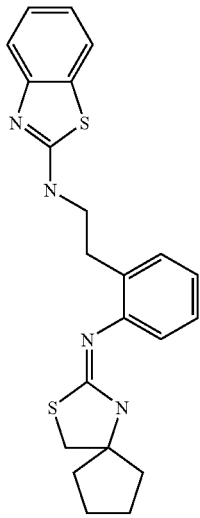 | | 408 | 409.10 |
| 178 | 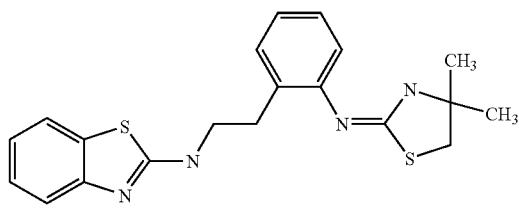 | | 382 | 383.09 |
| 179 | 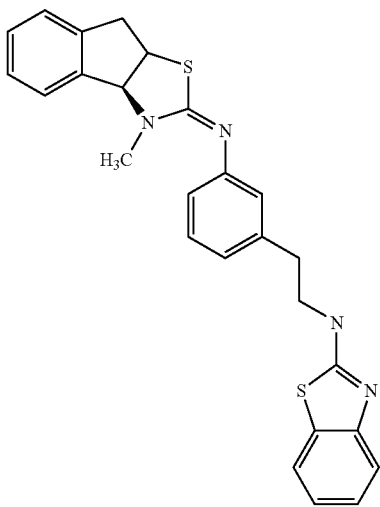 | | 456 | 457.11 |

-continued

| Ex. No. | Structure | Ki | Exact Mass (g/mol) | Obs. Mass (M + 1) |
|---|---|---|---|---|
| 180 | 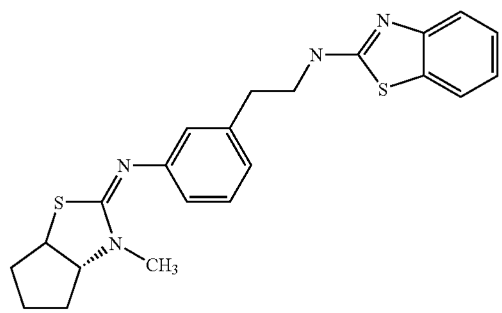 | | 408 | 409.10 |
| 181 | 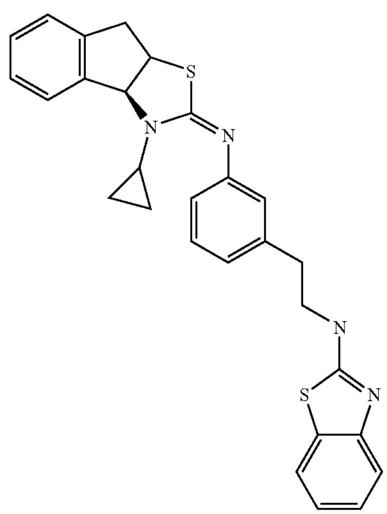 | | 482 | 483.12 |
| 182 | 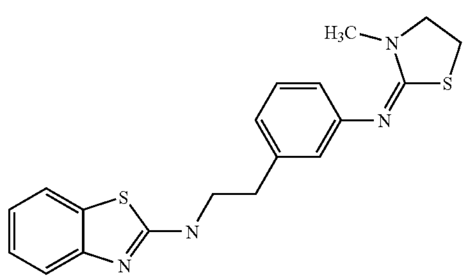 | C | 368 | 369.09 |
| 183 | 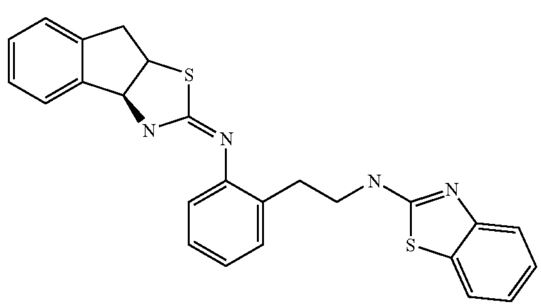 | C | 442 | 443.11 |

| Ex. No. | Structure | Ki | Exact Mass (g/mol) | Obs. Mass (M + 1) |
|---|---|---|---|---|
| 184 | 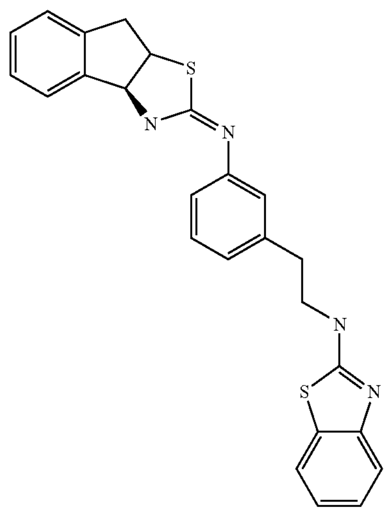 | C | 442 | 443.11 |
| 185 | 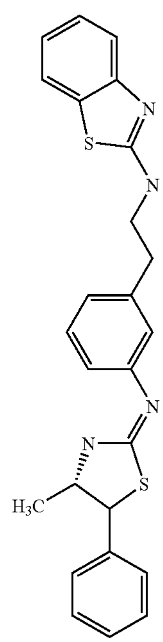 | A | 444 | 445.11 |
| 186 | 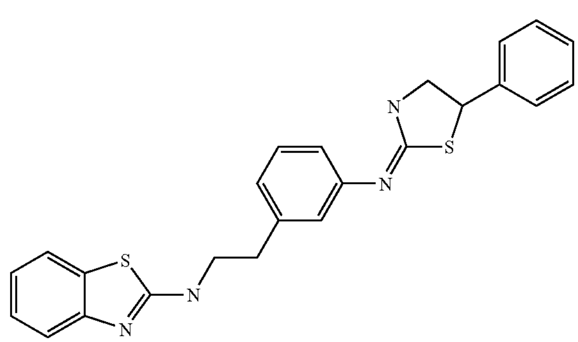 | C | 430 | 431.10 |

-continued

| Ex. No. | Structure | Ki | Exact Mass (g/mol) | Obs. Mass (M + 1) |
|---|---|---|---|---|
| 187 | 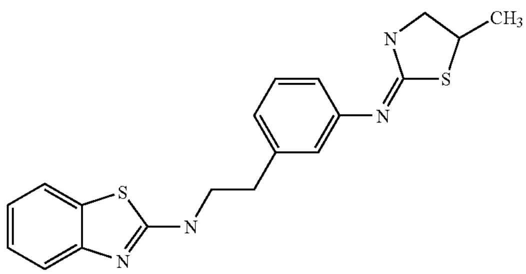 | C | 368 | 369.09 |
| 188 | 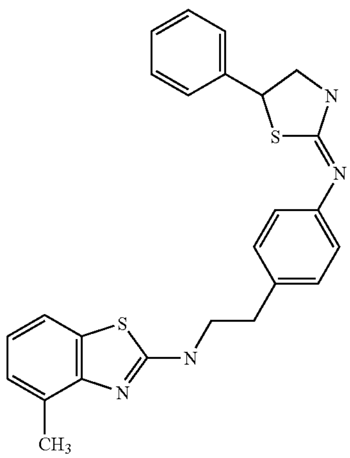 | C | 444 | 445.11 |
| 189 | 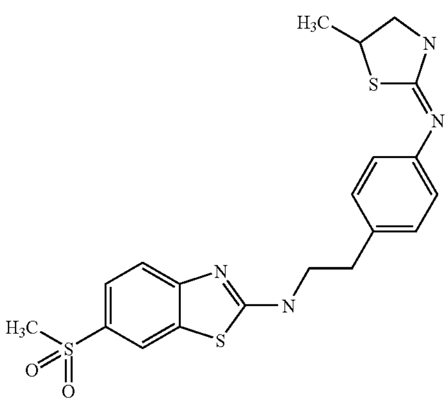 | C | 446 | 447.11 |
| 190 | 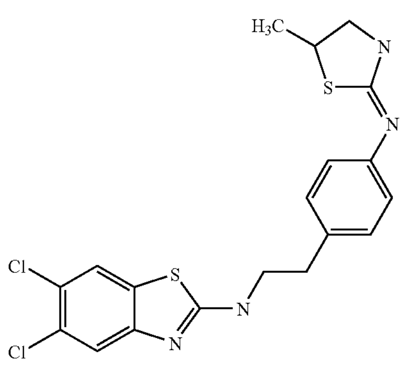 | C | 436 | 437.11 |

-continued

| Ex. No. | Structure | Ki | Exact Mass (g/mol) | Obs. Mass (M + 1) |
|---|---|---|---|---|
| 191 | 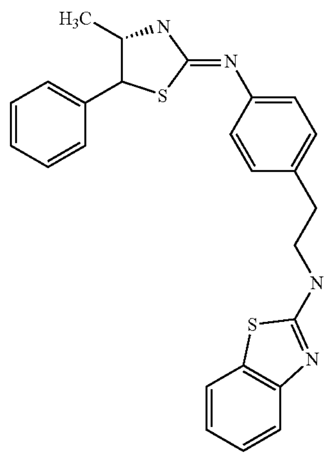 | C | 444 | 445.11 |
| 192 | 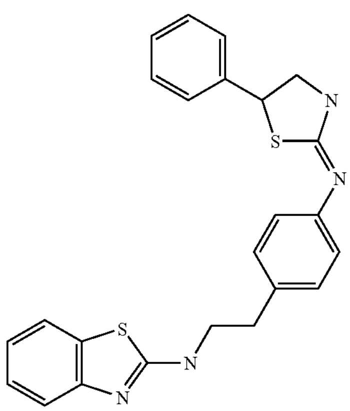 | C | 430 | 431.1 |
| 193 | 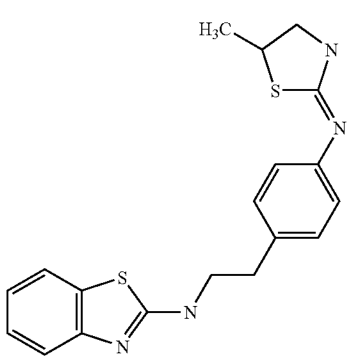 | C | 368 | 369.09 |

-continued

| Ex. No. | Structure | Ki | Exact Mass (g/mol) | Obs. Mass (M + 1) |
|---|---|---|---|---|
| 194 | 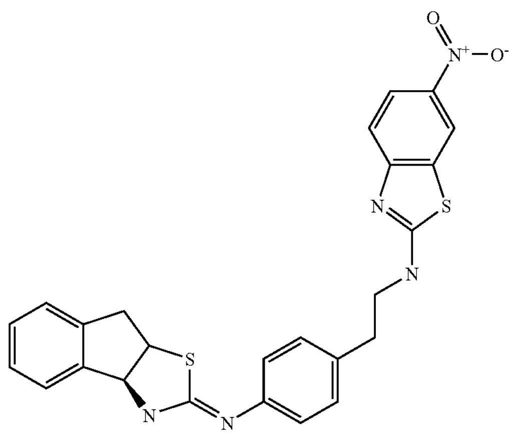 | C | 487 | 488.12 |
| 195 | 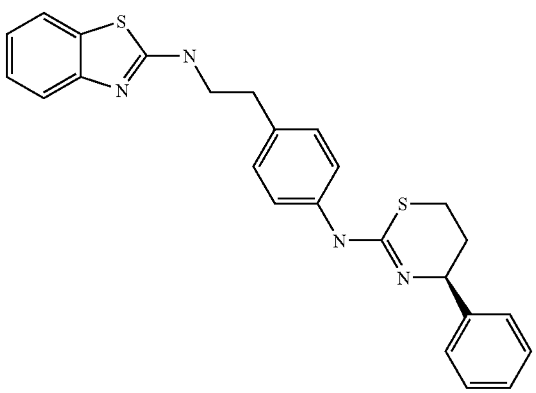 | A | 444 | 445.1 |
| 196 | 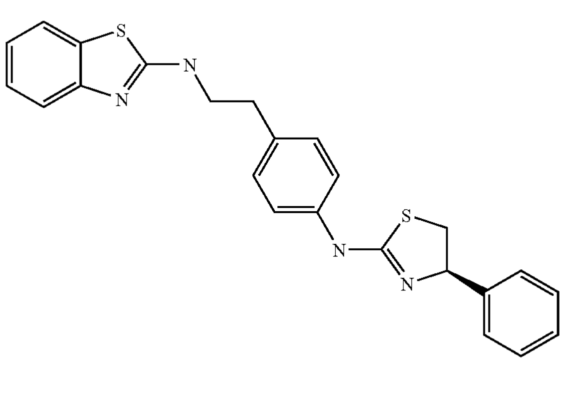 | A | 430 | |

-continued

| Ex. No. | Structure | Ki | Exact Mass (g/mol) | Obs. Mass (M + 1) |
|---|---|---|---|---|
| 197 | 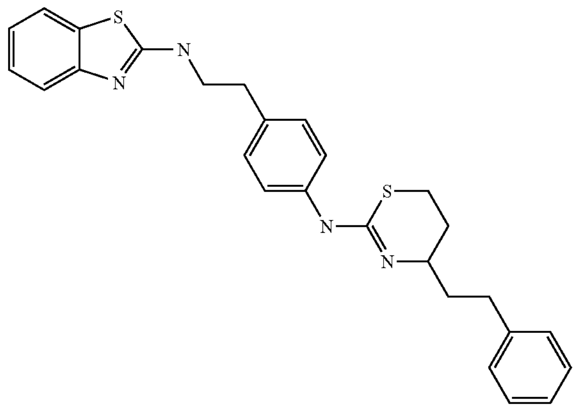 | A | 472 | 473.1 |
| 198 | 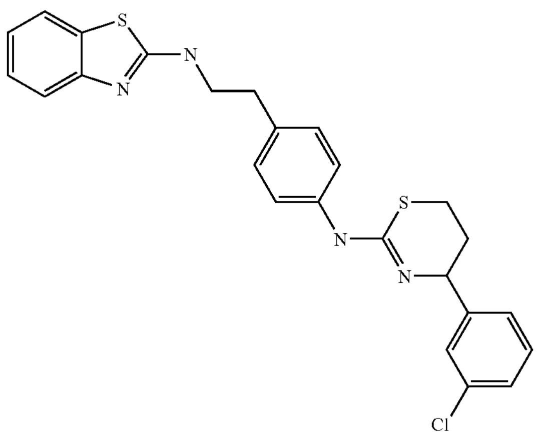 | A | 478 | 479.1 |
| 199 | 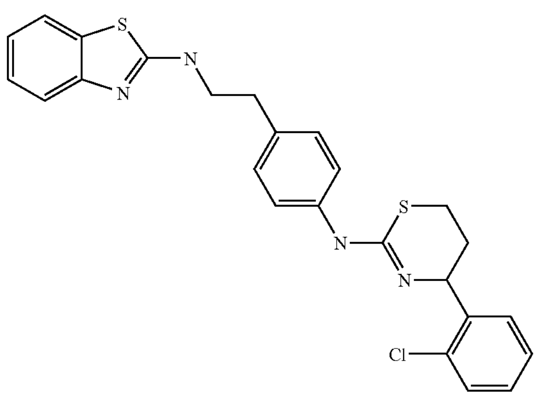 | A | 478 | 479.1 |
| 200 | 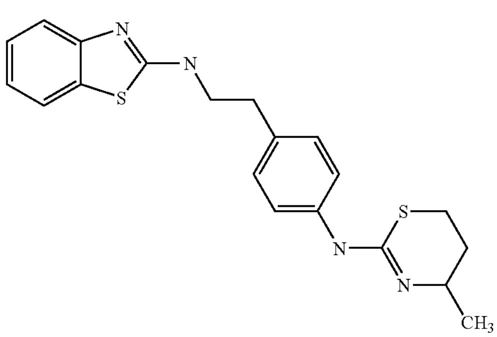 | A | 382 | 383.1 |

-continued
| Ex. No. | Structure | Ki | Exact Mass (g/mol) | Obs. Mass (M + 1) |
|---|---|---|---|---|
| 201 | 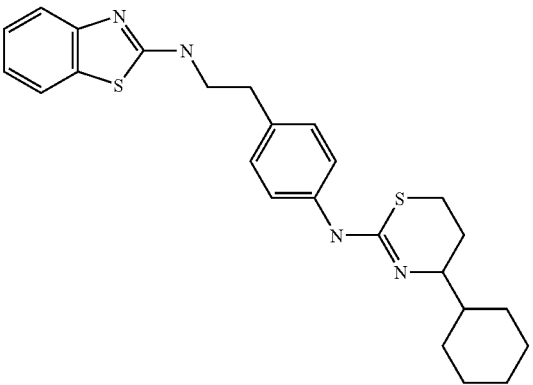 | A | 450 | |
| 202 | 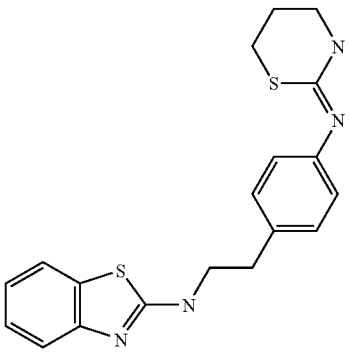 | A | 368 | 369.09 |
| 203 | 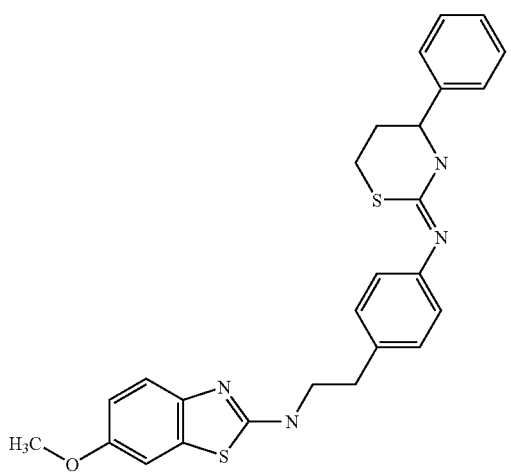 | A | 474 | 475.11 |

-continued
| Ex. No. | Structure | Ki | Exact Mass (g/mol) | Obs. Mass (M + 1) |
|---|---|---|---|---|
| 204 | 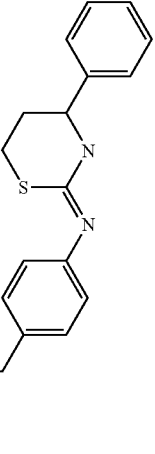 | A | 458 | 459.11 |
| 205 | 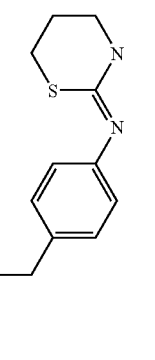 | A | 382 | 383.09 |
| 206 | 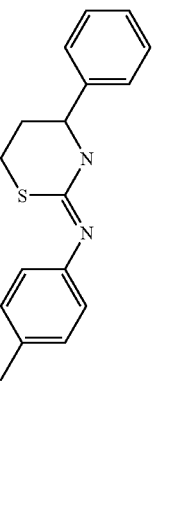 | C | 474 | 475.11 |

| Ex. No. | Structure | Ki | Exact Mass (g/mol) | Obs. Mass (M + 1) |
|---|---|---|---|---|
| 207 | 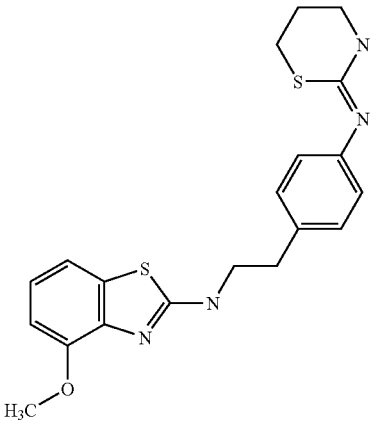 | C | 398 | 399.10 |
| 208 | 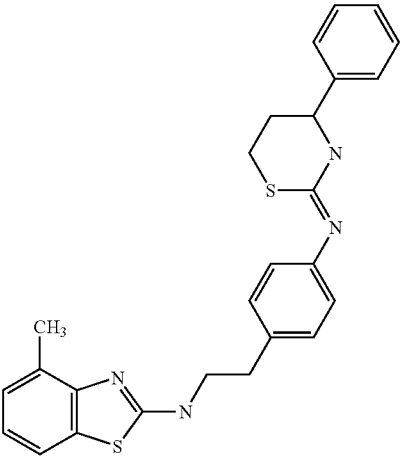 | C | 458 | 459.11 |
| 209 | 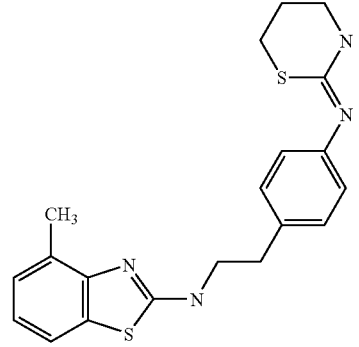 | C | 382 | 383.09 |

-continued

| Ex. No. | Structure | Ki | Exact Mass (g/mol) | Obs. Mass (M + 1) |
|---|---|---|---|---|
| 210 | 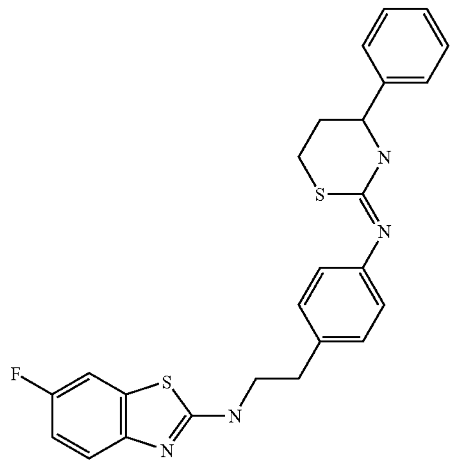 | A | 462 | 463.11 |
| 211 | 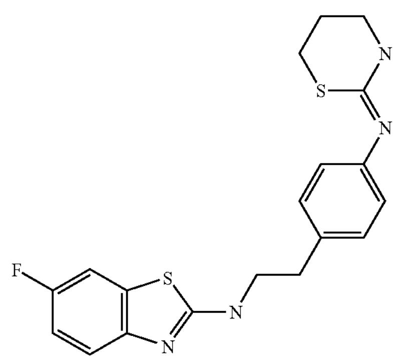 | A | 386 | 387.10 |
| 212 | 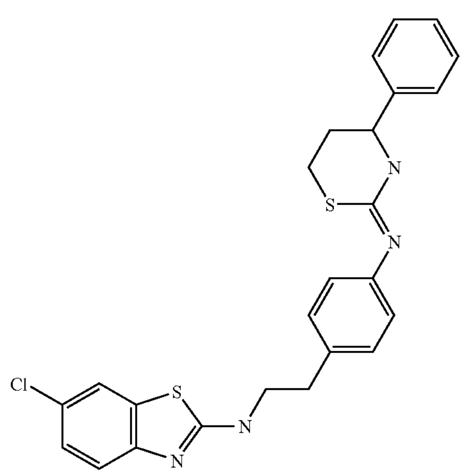 | A | 478 | 479.11 |

| Ex. No. | Structure | Ki | Exact Mass (g/mol) | Obs. Mass (M + 1) |
| --- | --- | --- | --- | --- |
| 213 | 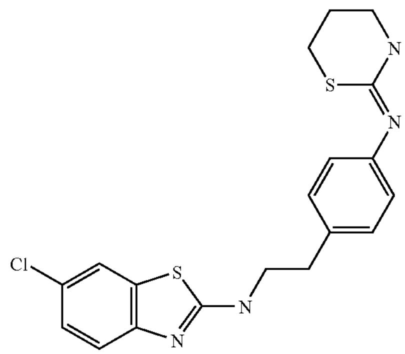 | A | 402 | 403.10 |
| 214 | 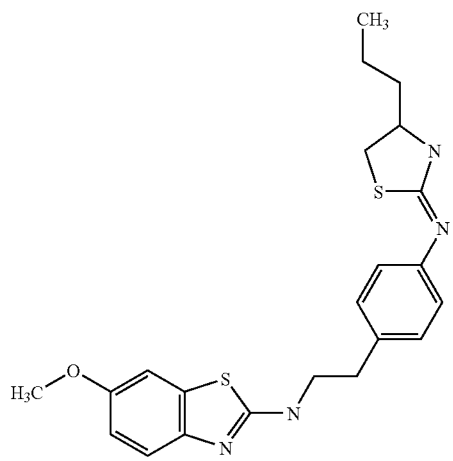 | A | 426 | 427.1 |
| 215 | 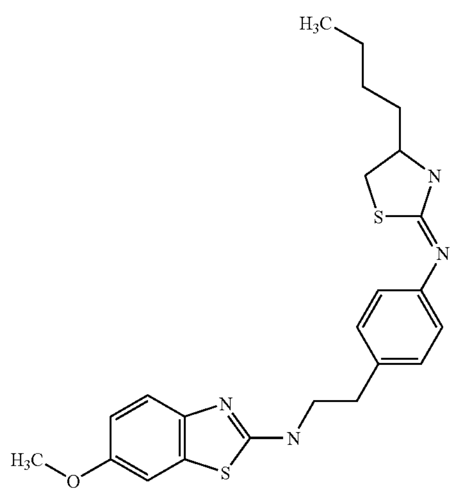 | A | 440 | 441.11 |

| Ex. No. | Structure | Ki | Exact Mass (g/mol) | Obs. Mass (M + 1) |
|---|---|---|---|---|
| 216 | 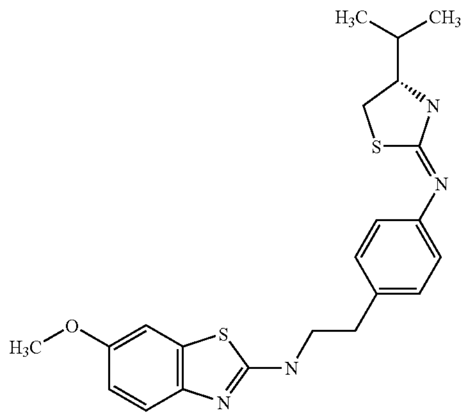 | B | 426 | 427.1 |
| 217 | 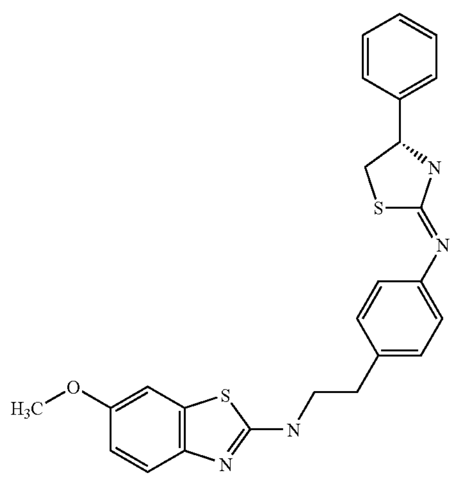 | C | 460 | 461.11 |
| 218 | 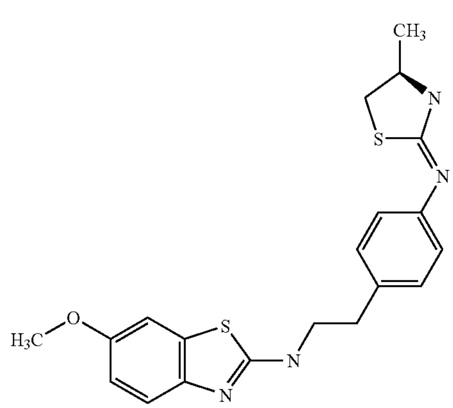 | B | 398 | 399.10 |

-continued

| Ex. No. | Structure | Ki | Exact Mass (g/mol) | Obs. Mass (M + 1) |
|---|---|---|---|---|
| 219 | 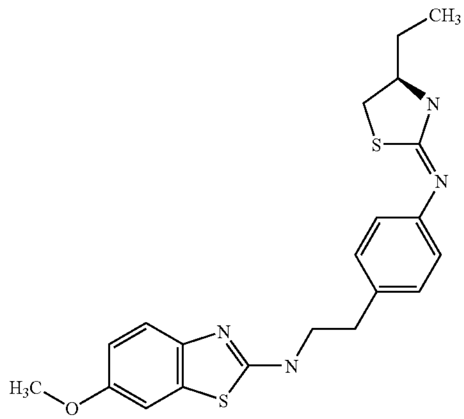 | B | 412 | 413.10 |
| 220 | 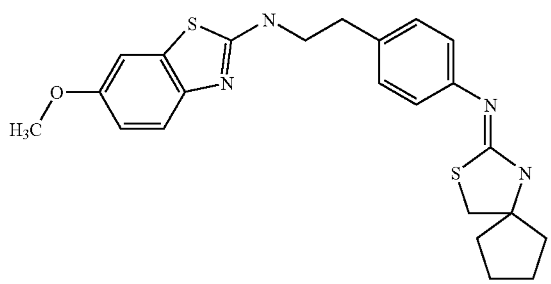 | B | 438 | 439.11 |
| 221 | 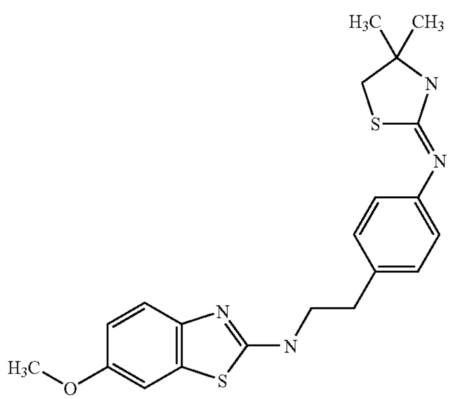 | B | 412 | 413.10 |
| 222 | 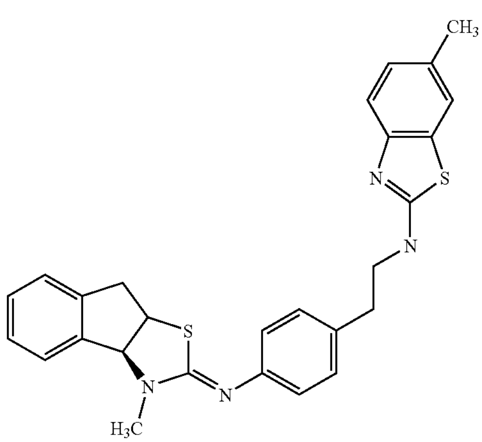 | C | 470 | 471.11 |

-continued

| Ex. No. | Structure | Ki | Exact Mass (g/mol) | Obs. Mass (M + 1) |
|---|---|---|---|---|
| 223 | 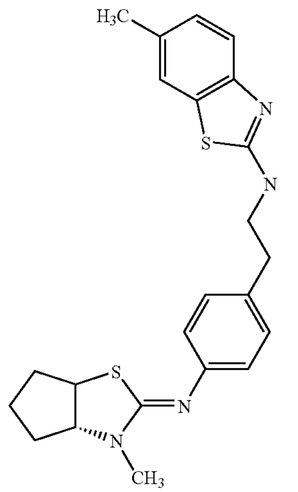 | C | 422 | 423.10 |
| 224 | 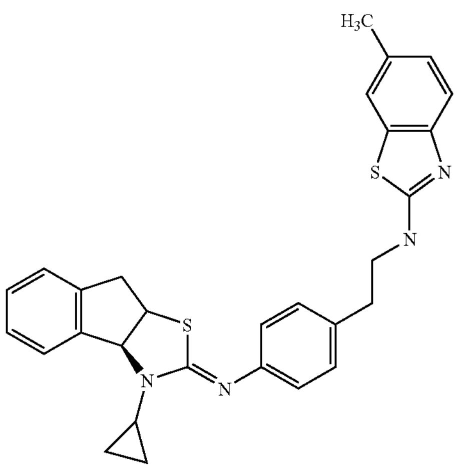 | C | 496 | 497.12 |
| 225 | 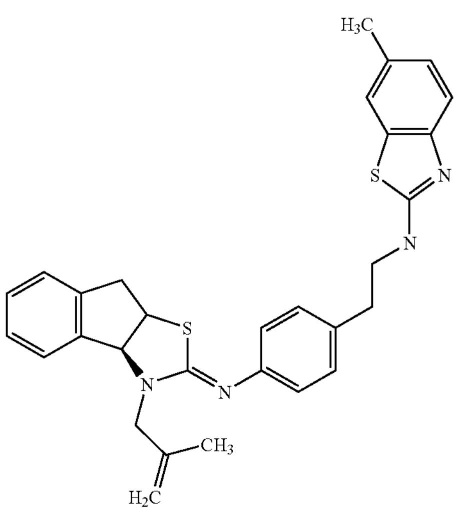 | C | 510 | 511.12 |

| Ex. No. | Structure | Ki | Exact Mass (g/mol) | Obs. Mass (M + 1) |
|---|---|---|---|---|
| 226 | 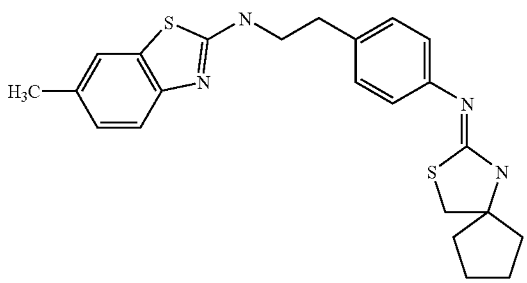 | B | 422 | 423.10 |
| 227 | 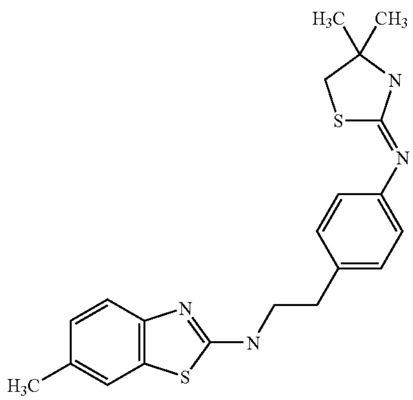 | A | 396 | 397.10 |
| 228 | 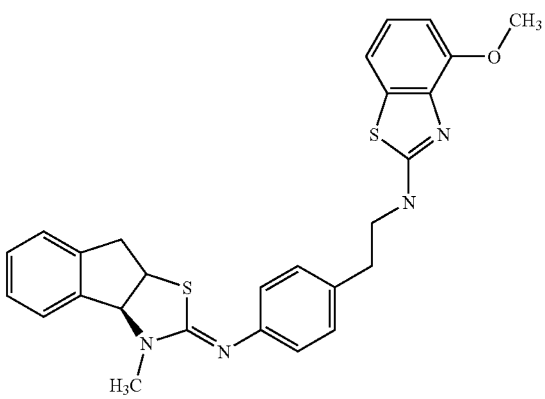 | C | 486 | 487.12 |
| 229 | 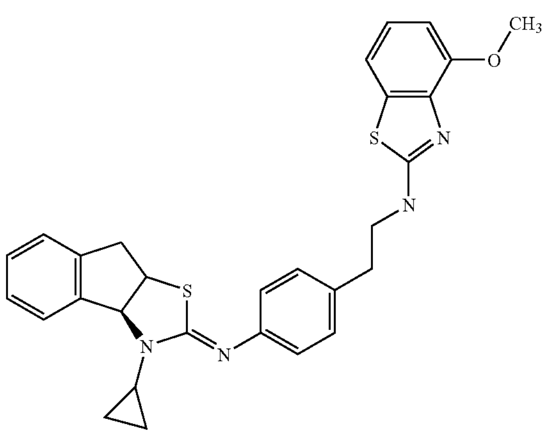 | C | 512 | 513.12 |

-continued
| Ex. No. | Structure | Ki | Exact Mass (g/mol) | Obs. Mass (M + 1) |
|---|---|---|---|---|
| 230 | 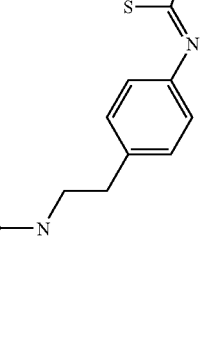 | C | 398 | 399.10 |
| 231 | 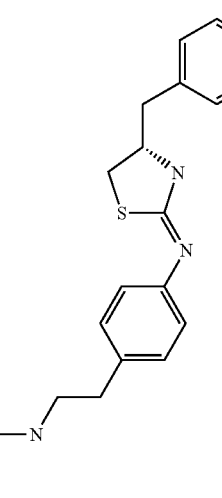 | | 474 | 475.11 |
| 232 | 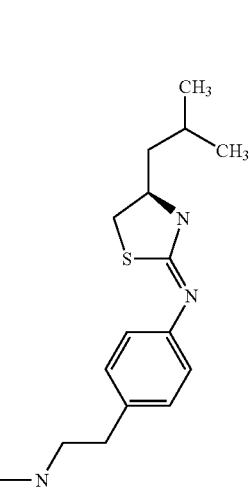 | | 440 | 441.11 |

-continued

| Ex. No. | Structure | Ki | Exact Mass (g/mol) | Obs. Mass (M + 1) |
|---|---|---|---|---|
| 233 | 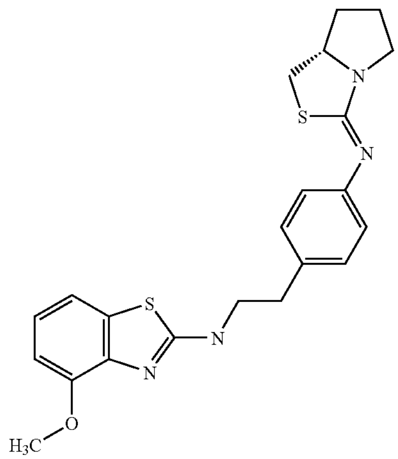 | | 424 | 425.10 |
| 234 | 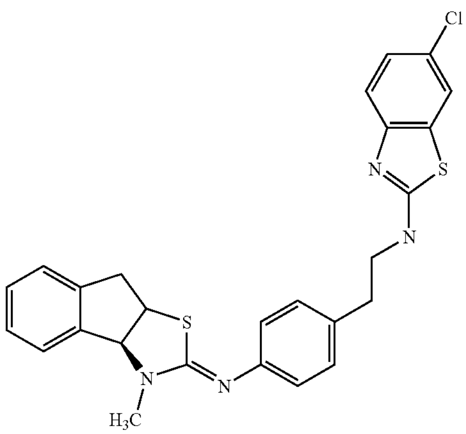 | | 490 | 491.12 |
| 235 | 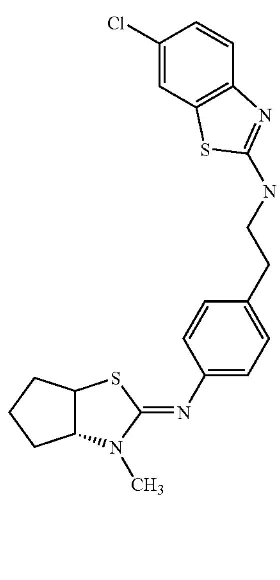 | | 442 | 443.11 |

| Ex. No. | Structure | Ki | Exact Mass (g/mol) | Obs. Mass (M + 1) |
|---|---|---|---|---|
| 236 | 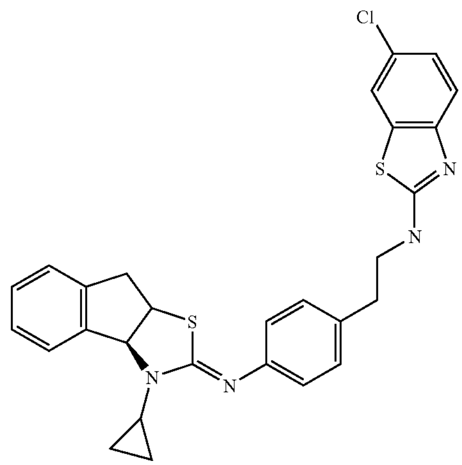 | | 516 | 517.12 |
| 237 | 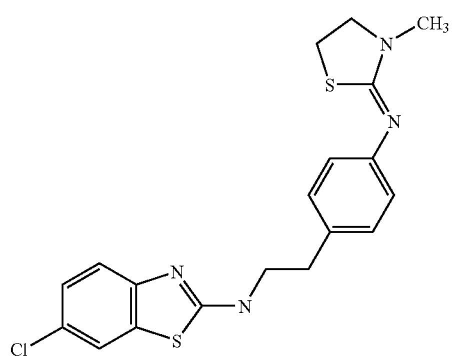 | | 402 | 403.10 |
| 238 | 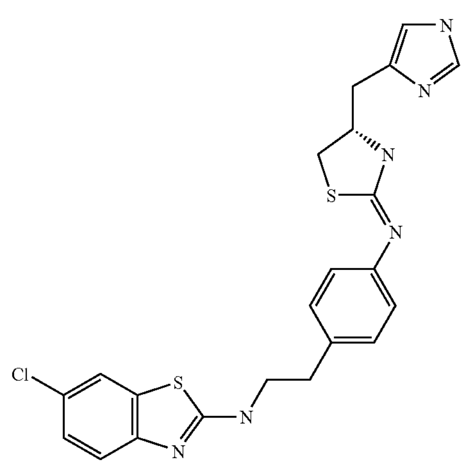 | B | 468 | 469.11 |
| 239 | 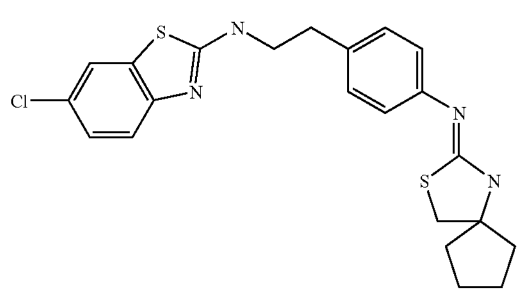 | B | 442 | 443.11 |

-continued

| Ex. No. | Structure | Ki | Exact Mass (g/mol) | Obs. Mass (M + 1) |
|---|---|---|---|---|
| 240 | 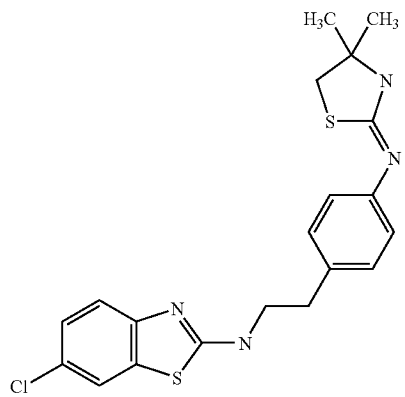 | B | 416 | 417.10 |
| 241 | 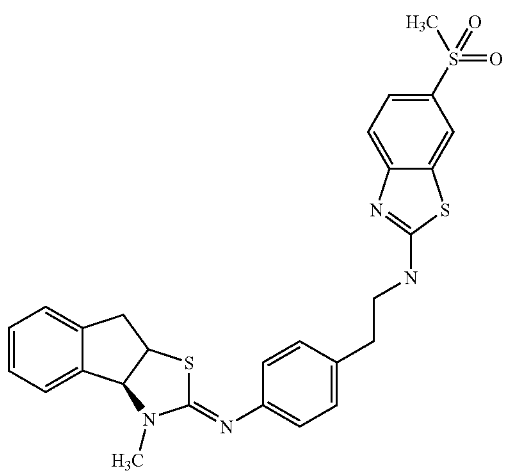 | | 534 | 535.13 |
| 242 | 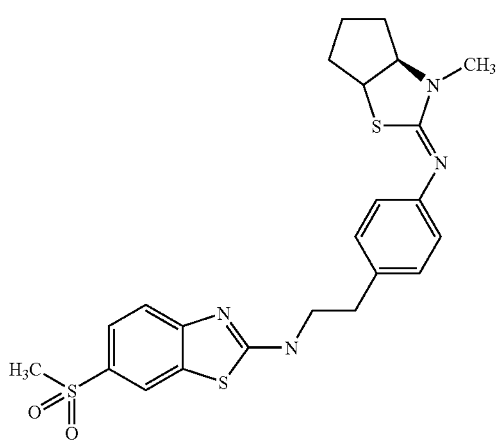 | | 486 | 487.12 |

-continued
| Ex. No. | Structure | Ki | Exact Mass (g/mol) | Obs. Mass (M + 1) |
|---|---|---|---|---|
| 243 | 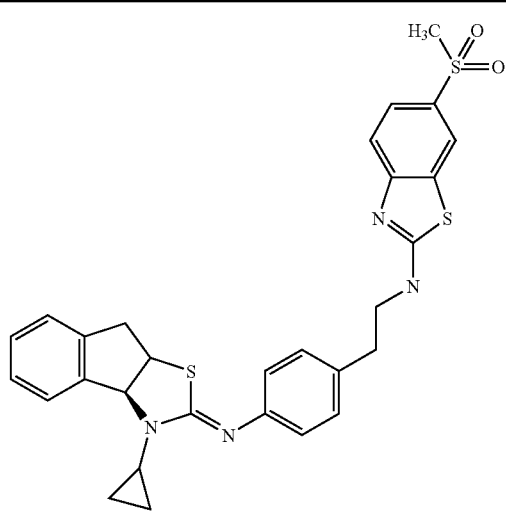 | | 560 | 561.13 |
| 244 | 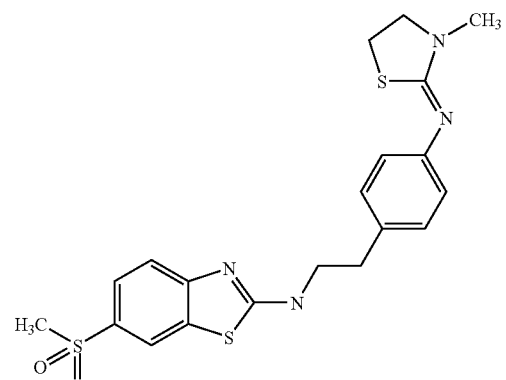 | | 446 | 447.11 |
| 245 | 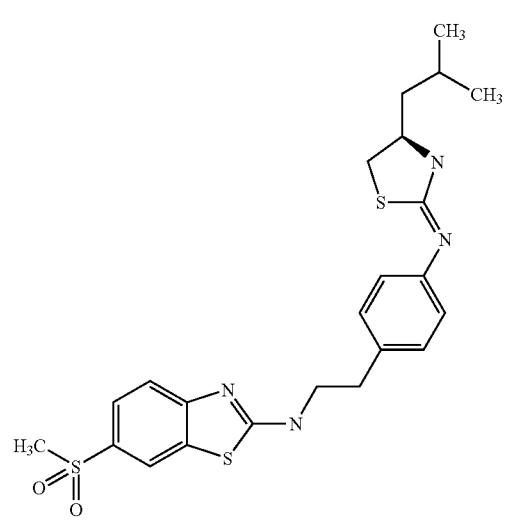 | B | 488 | 489.12 |

-continued

| Ex. No. | Structure | Ki | Exact Mass (g/mol) | Obs. Mass (M + 1) |
|---------|-----------|-----|---------------------|--------------------|
| 246 | 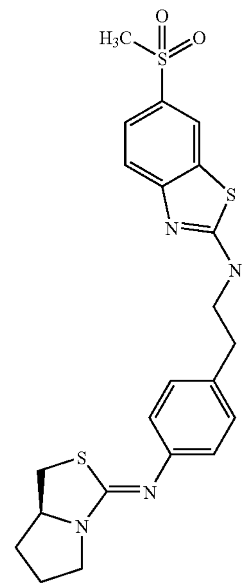 | | 472 | 473.11 |
| 247 | 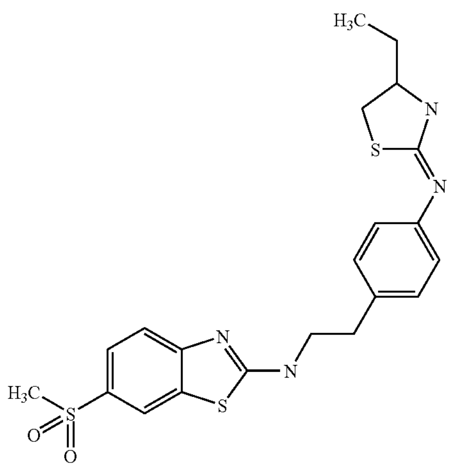 | | 460 | 461.11 |
| 248 | 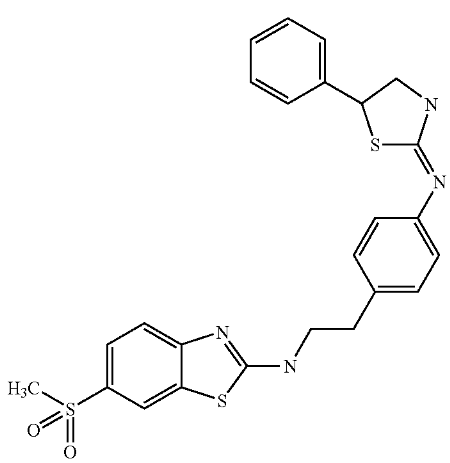 | | 508 | 509.12 |

-continued
| Ex. No. | Structure | Ki | Exact Mass (g/mol) | Obs. Mass (M + 1) |
|---|---|---|---|---|
| 249 | 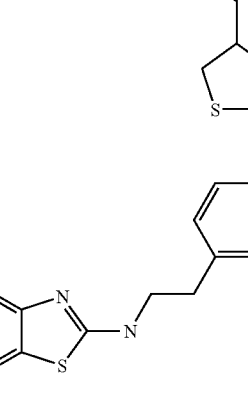 | B | 474 | 475.11 |
| 250 | 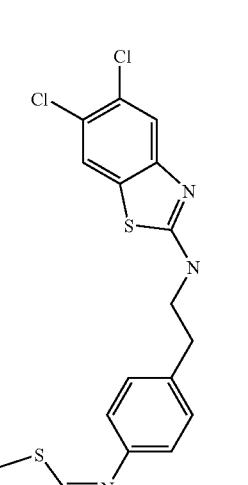 | | 476 | 477.11 |
| 251 | 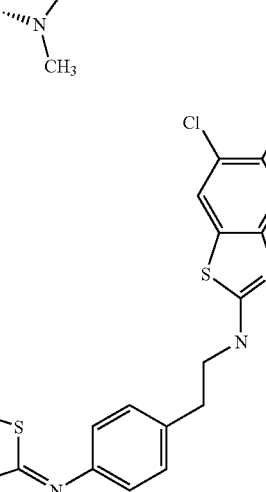 | | 550 | 551.1 |

-continued
| Ex. No. | Structure | Ki | Exact Mass (g/mol) | Obs. Mass (M + 1) |
|---|---|---|---|---|
| 252 | 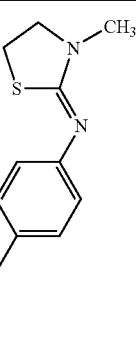 | | 436 | 437.11 |
| 253 | 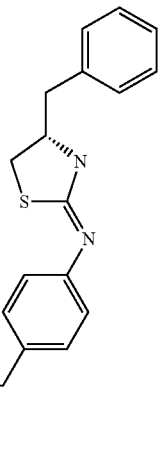 | | 512 | 513.1 |
| 254 | 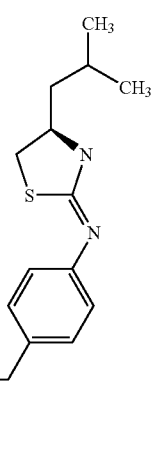 | | 478 | 479.1 |

-continued

| Ex. No. | Structure | Ki | Exact Mass (g/mol) | Obs. Mass (M + 1) |
|---|---|---|---|---|
| 255 | 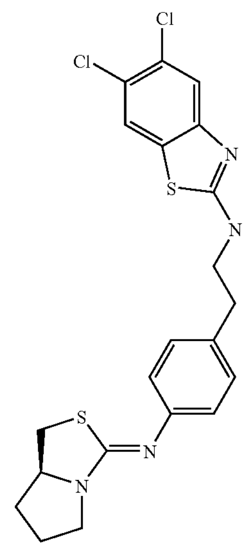 | | 462 | 463.11 |
| 256 | 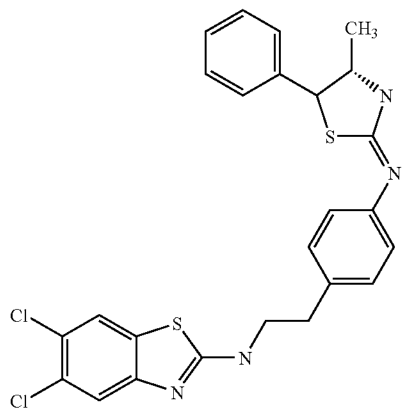 | | 512 | 513.1 |
| 257 | 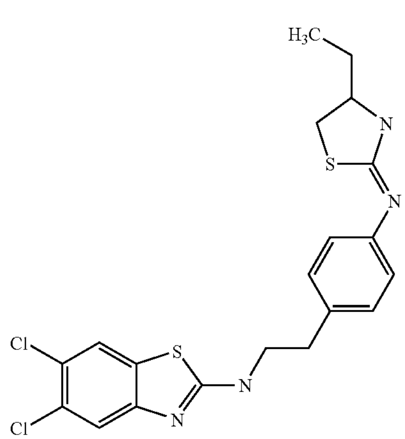 | | 450 | 451.11 |

-continued

| Ex. No. | Structure | Ki | Exact Mass (g/mol) | Obs. Mass (M + 1) |
|---|---|---|---|---|
| 258 | 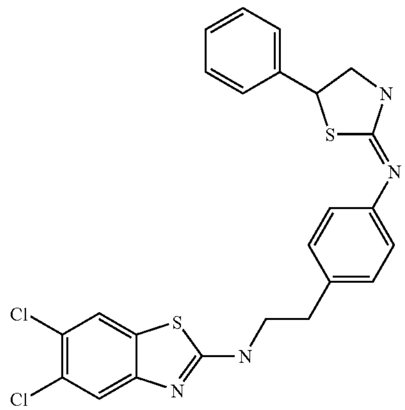 | | 498 | 499.1 |
| 259 | 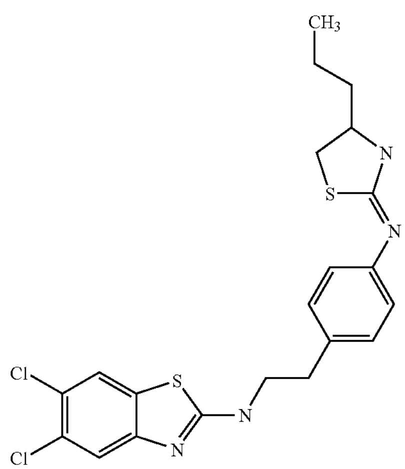 | | 464 | 465.11 |
| 260 | 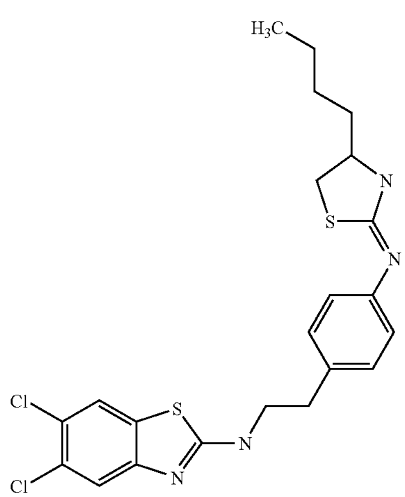 | | 478 | 479.1 |

-continued

| Ex. No. | Structure | Ki | Exact Mass (g/mol) | Obs. Mass (M + 1) |
|---|---|---|---|---|
| 261 | 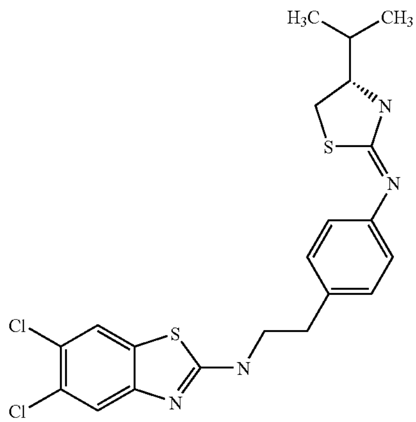 | | 464 | 465.11 |
| 262 | 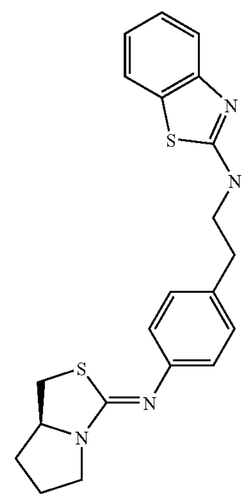 | | 394 | 395.10 |
| 263 | 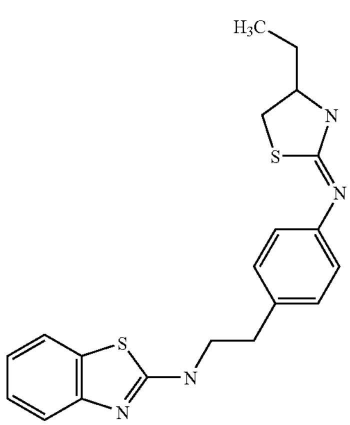 | A | 382 | 383.09 |

-continued
| Ex. No. | Structure | Ki | Exact Mass (g/mol) | Obs. Mass (M + 1) |
|---|---|---|---|---|
| 264 | 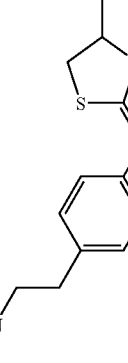 | A | 396 | 397.10 |
| 265 | 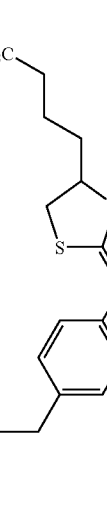 |  | 410 | 411.10 |
| 266 | 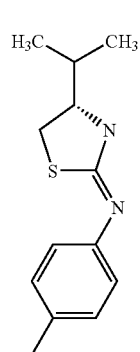 |  | 396 | 396.10 |

-continued

| Ex. No. | Structure | Ki | Exact Mass (g/mol) | Obs. Mass (M + 1) |
|---|---|---|---|---|
| 267 | 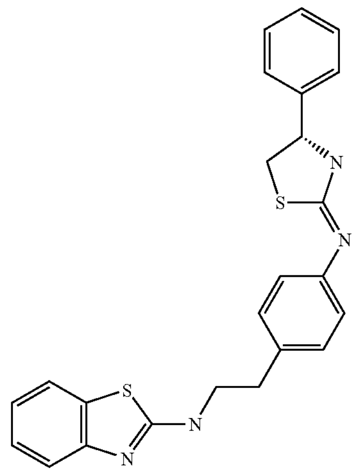 | | 430 | 431.10 |
| 268 | 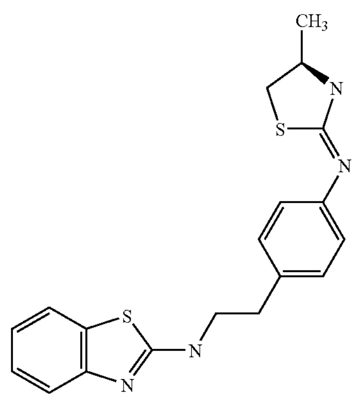 | A | 368 | 369.09 |
| 269 | 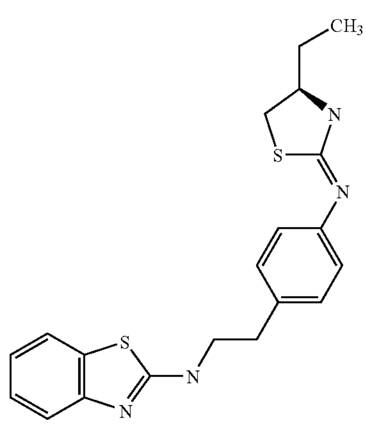 | A | 382 | 383.09 |

-continued

| Ex. No. | Structure | Ki | Exact Mass (g/mol) | Obs. Mass (M + 1) |
|---|---|---|---|---|
| 270 | 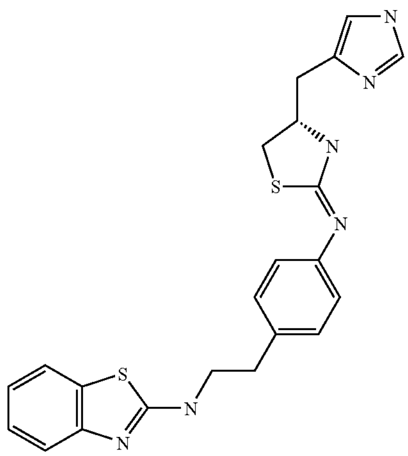 | A | 434 | 435.11 |
| 271 | 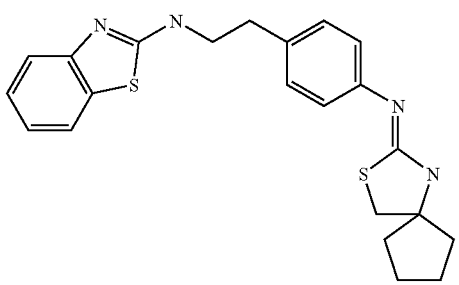 | A | 408 | 409.10 |
| 272 | 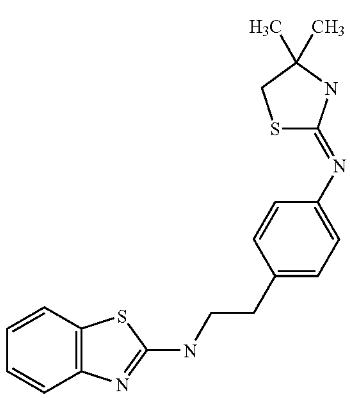 | A | 382 | 383.09 |

-continued

| Ex. No. | Structure | Ki | Exact Mass (g/mol) | Obs. Mass (M + 1) |
|---|---|---|---|---|
| 273 | 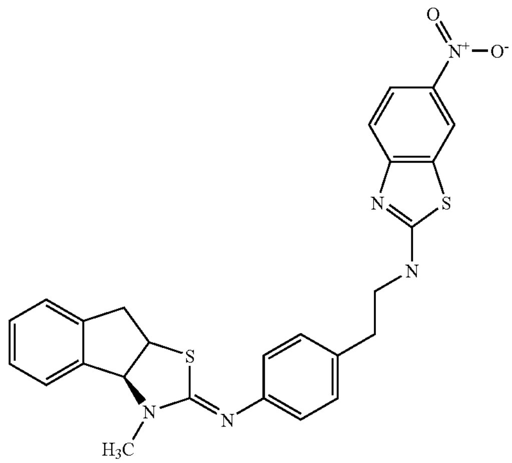 | | 501 | 502.12 |
| 274 | 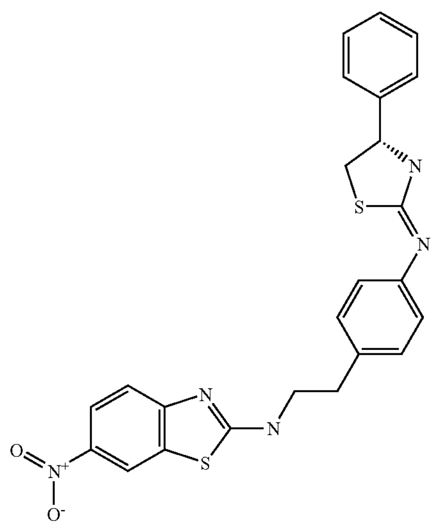 | | 475 | 476.11 |
| 275 | 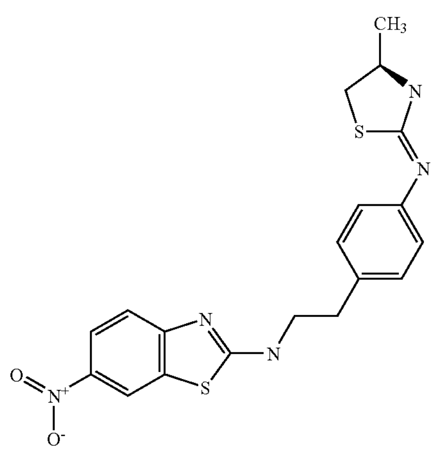 | | 413 | 414.10 |

-continued
| Ex. No. | Structure | Ki | Exact Mass (g/mol) | Obs. Mass (M + 1) |
|---|---|---|---|---|
| 276 | 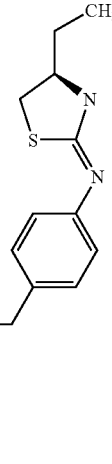 | | 427 | 428.10 |
| 277 | 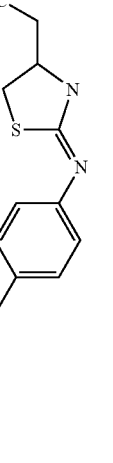 | | 412 | 413.1 |
| 278 | 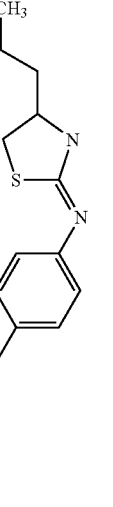 | | 426 | 427.1 |

| Ex. No. | Structure | Ki | Exact Mass (g/mol) | Obs. Mass (M + 1) |
|---|---|---|---|---|
| 279 | 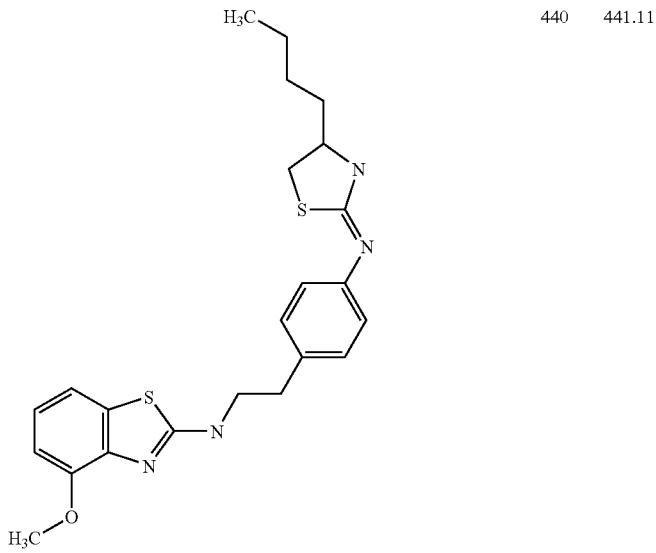 | | 440 | 441.11 |
| 280 | 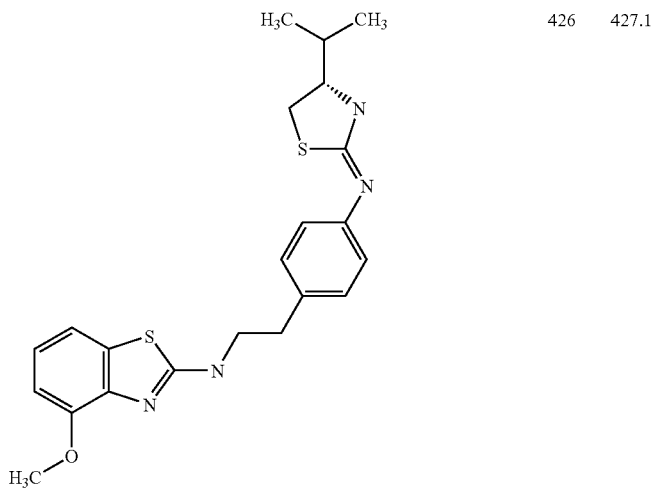 | | 426 | 427.1 |

-continued
| Ex. No. | Structure | Ki | Exact Mass (g/mol) | Obs. Mass (M + 1) |
|---|---|---|---|---|
| 281 | 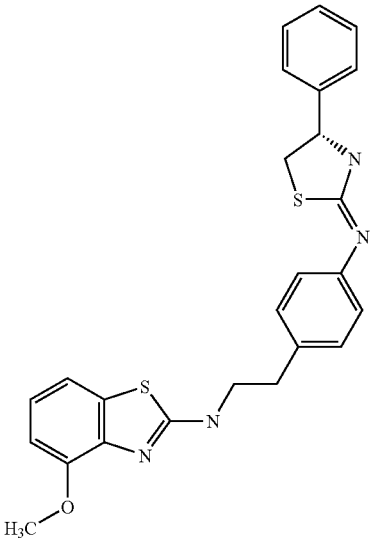 | | 460 | 461.11 |
| 282 | 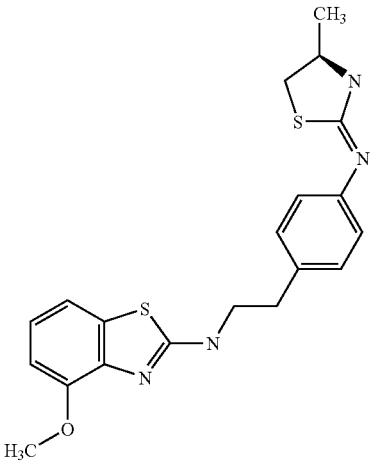 | | 398 | 399.1 |
| 283 | 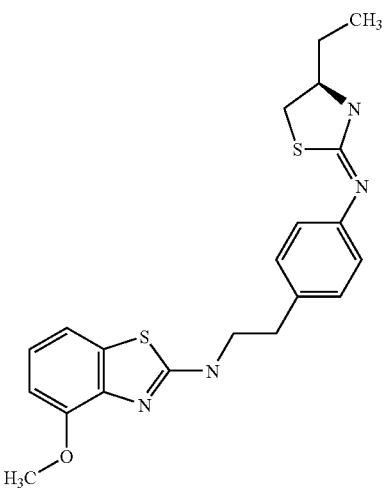 | | 412 | 413.1 |

| Ex. No. | Structure | Ki | Exact Mass (g/mol) | Obs. Mass (M + 1) |
|---|---|---|---|---|
| 284 | 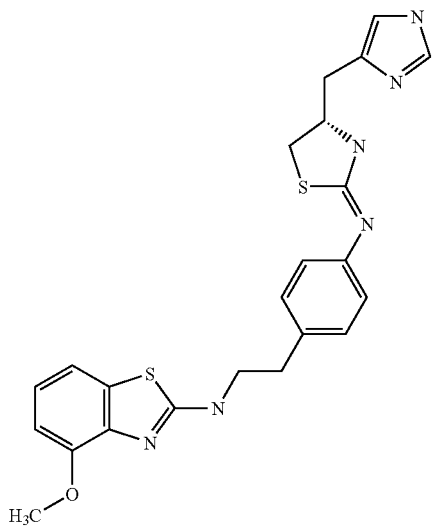 | | 464 | 465.11 |
| 285 | 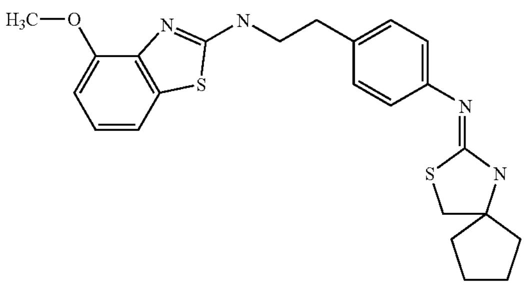 | | 438 | 439.11 |
| 286 | 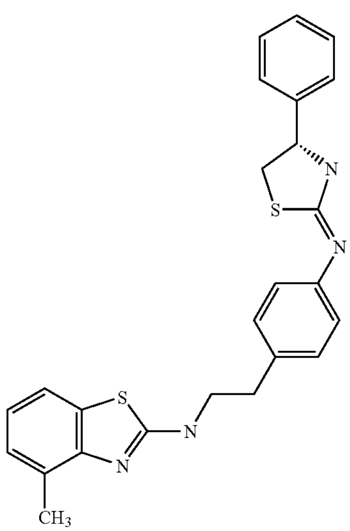 | | 444 | 445.11 |

-continued
| Ex. No. | Structure | Ki | Exact Mass (g/mol) | Obs. Mass (M + 1) |
|---|---|---|---|---|
| 287 | 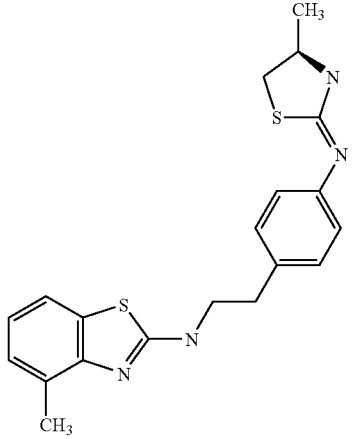 | | 382 | 383.09 |
| 288 | 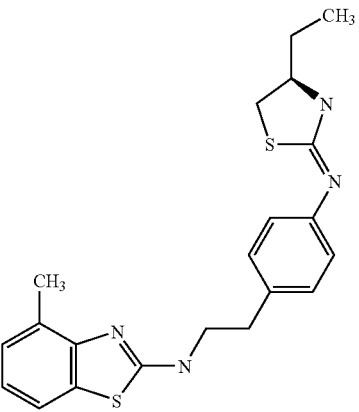 | | 396 | 397.1 |
| 289 | 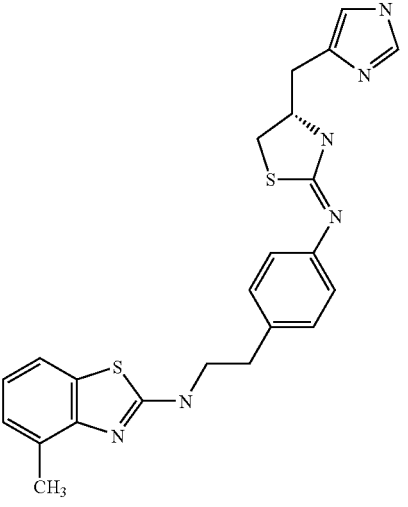 | | 448 | 449.11 |

-continued
| Ex. No. | Structure | Ki | Exact Mass (g/mol) | Obs. Mass (M + 1) |
|---|---|---|---|---|
| 290 | 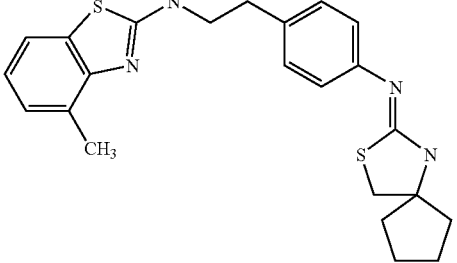 | | 422 | 423.1 |
| 291 | 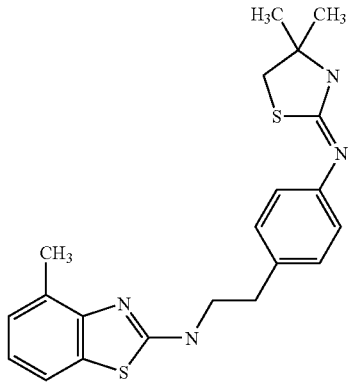 | | 396 | 397.1 |
| 292 | 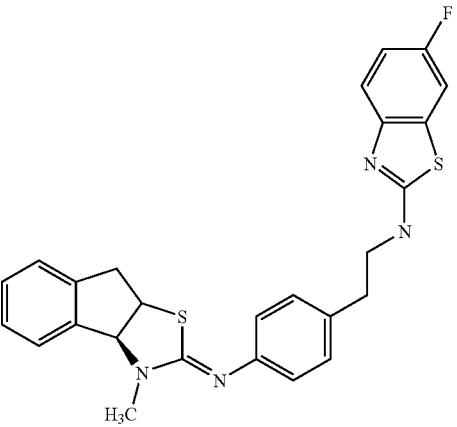 | | 474 | 475.11 |

| Ex. No. | Structure | Ki | Exact Mass (g/mol) | Obs. Mass (M + 1) |
|---|---|---|---|---|
| 293 | 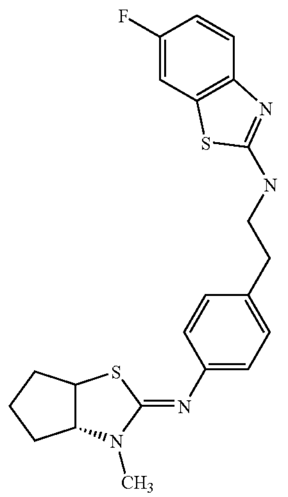 | | 426 | 427.10 |
| 294 | 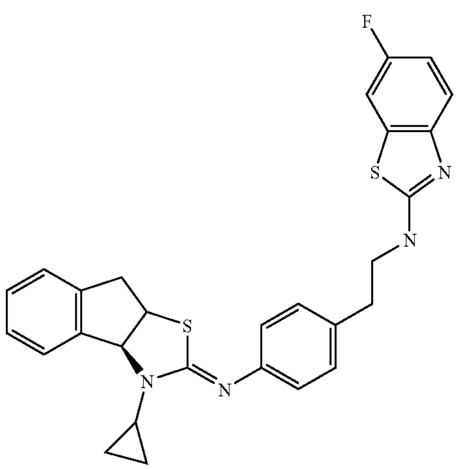 | | 500 | 501.12 |
| 295 | 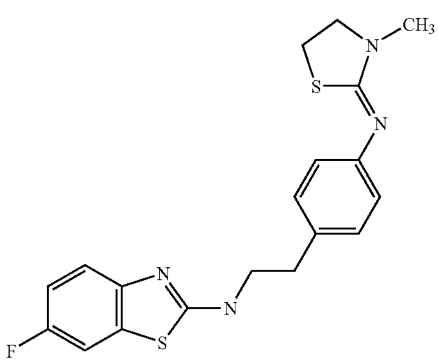 | | 386 | 387.10 |

-continued
| Ex. No. | Structure | Ki | Exact Mass (g/mol) | Obs. Mass (M + 1) |
|---|---|---|---|---|
| 296 | 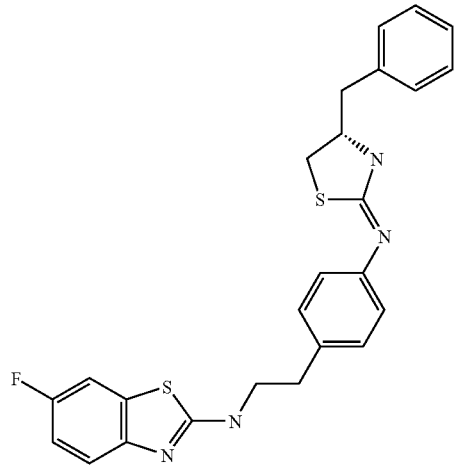 | | 462 | 463.11 |
| 297 | 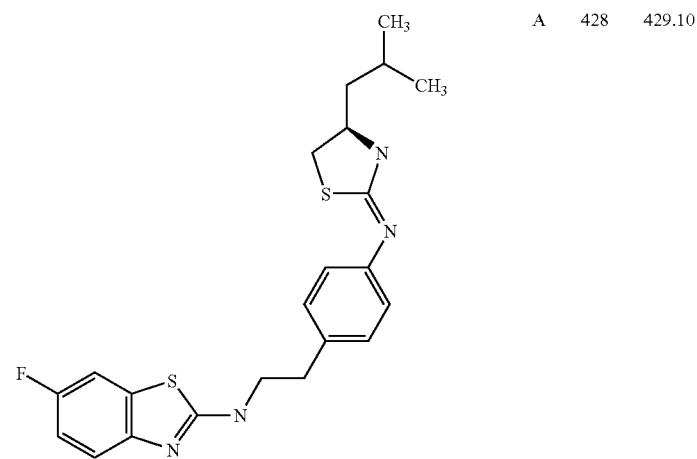 | A | 428 | 429.10 |
| 298 | 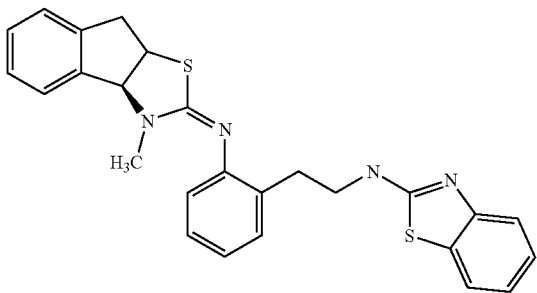 | | 456 | 457.11 |

-continued

| Ex. No. | Structure | Ki | Exact Mass (g/mol) | Obs. Mass (M + 1) |
|---|---|---|---|---|
| 299 | 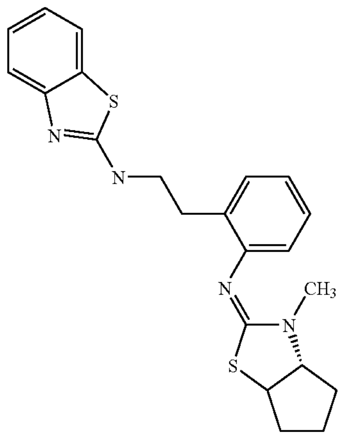 | | 408 | 409.10 |
| 300 | 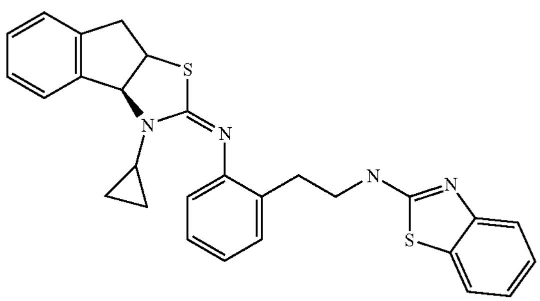 | | 482 | 483.12 |
| 301 | 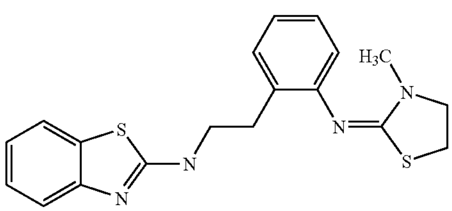 | | 368 | 369.09 |
| 302 | 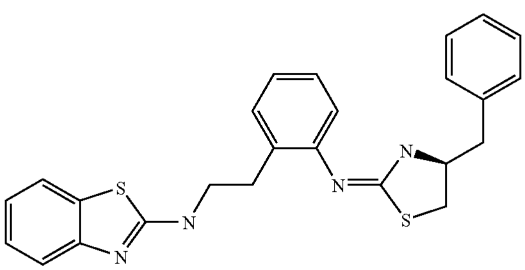 | | 444 | 445.11 |
| 303 | 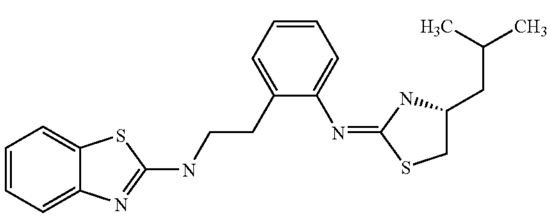 | | 410 | 411.10 |

-continued

| Ex. No. | Structure | Ki | Exact Mass (g/mol) | Obs. Mass (M + 1) |
|---|---|---|---|---|
| 304 | 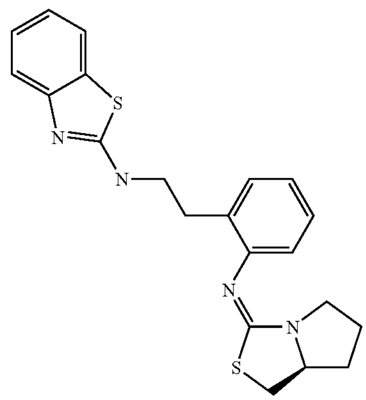 | | 394 | 395.10 |
| 305 | 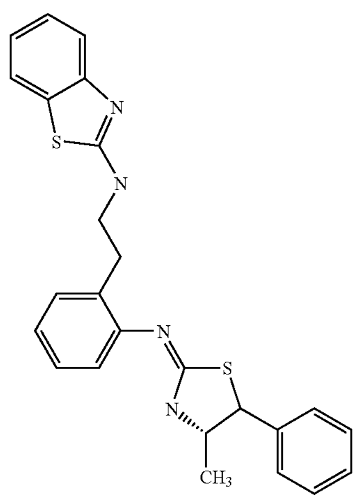 | | 444 | 445.11 |
| 306 | 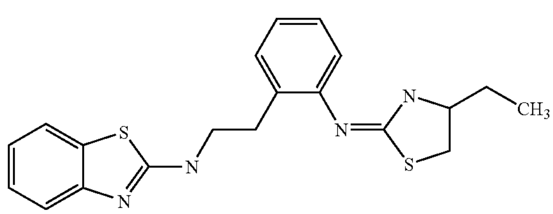 | | 382 | 383.09 |

-continued

| Ex. No. | Structure | Ki | Exact Mass (g/mol) | Obs. Mass (M + 1) |
|---|---|---|---|---|
| 307 | 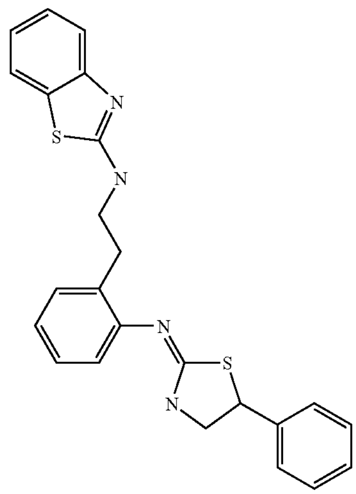 | | 430 | 431.10 |
| 308 | 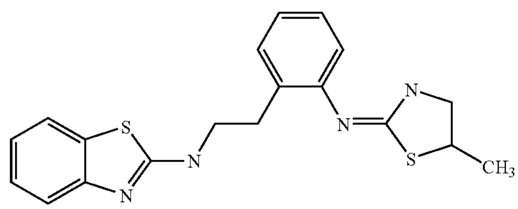 | | 368 | 369.09 |
| 309 | 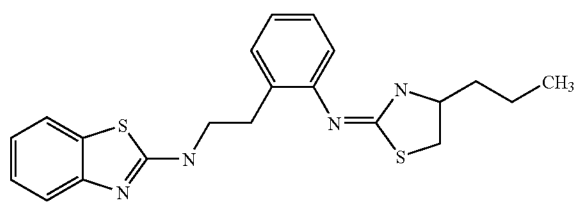 | | 396 | 397.10 |
| 310 | 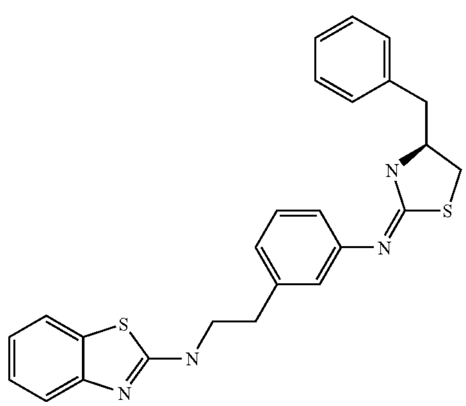 | | 444 | 445.11 |

-continued

| Ex. No. | Structure | Ki | Exact Mass (g/mol) | Obs. Mass (M + 1) |
|---|---|---|---|---|
| 311 | 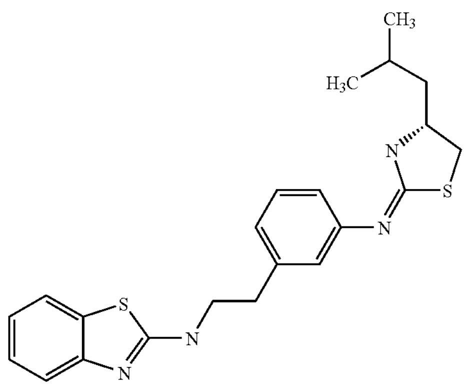 | | 410 | 411.10 |
| 312 | 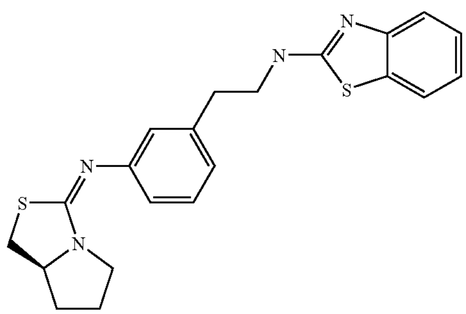 | | 394 | 395.10 |
| 313 | 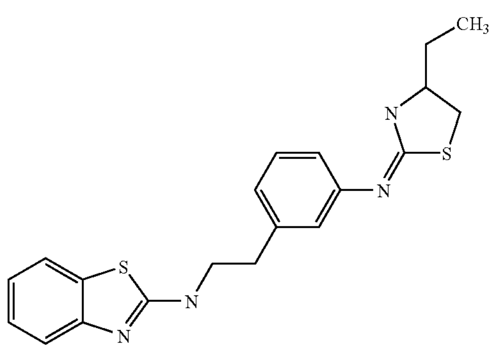 | | 382 | 383.09 |
| 314 | 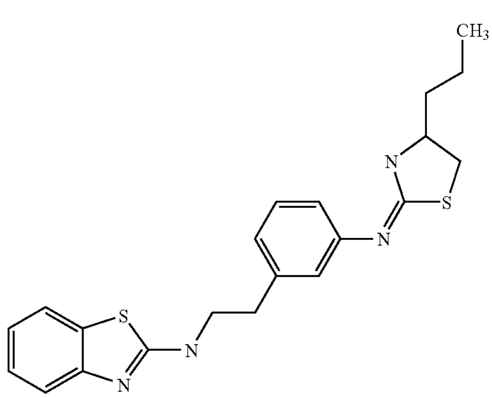 | | 396 | 397.10 |

-continued

| Ex. No. | Structure | Ki | Exact Mass (g/mol) | Obs. Mass (M + 1) |
|---|---|---|---|---|
| 315 | 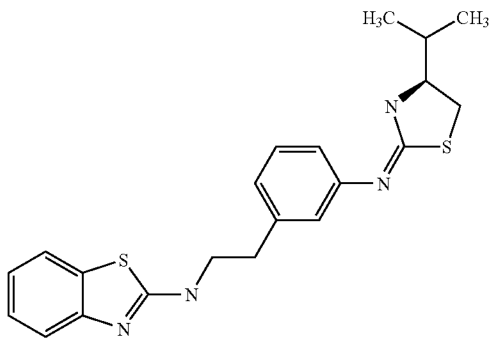 | | 396 | 397.10 |
| 316 | 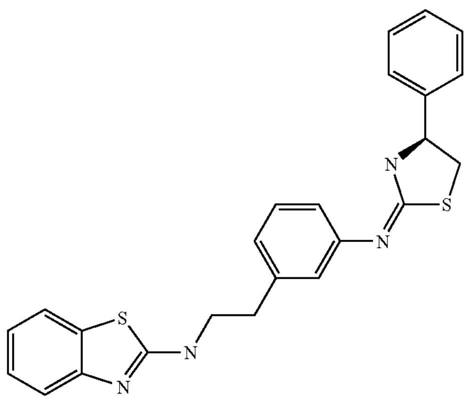 | | 430 | 431.10 |
| 317 | 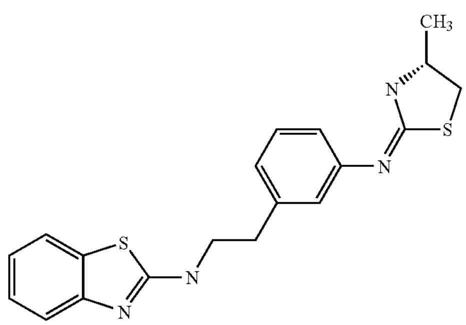 | | 368 | 369.09 |
| 318 | 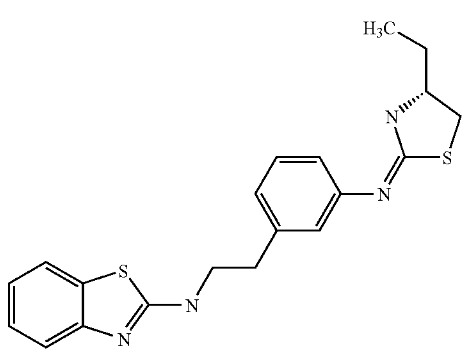 | | 382 | 383.09 |

-continued

| Ex. No. | Structure | Ki | Exact Mass (g/mol) | Obs. Mass (M + 1) |
|---|---|---|---|---|
| 319 | 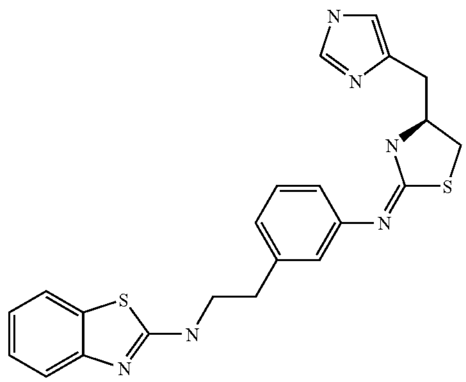 | | 434 | 435.11 |
| 320 | 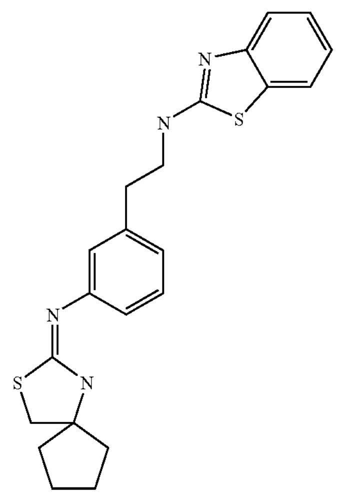 | | 408 | 409.10 |
| 321 | 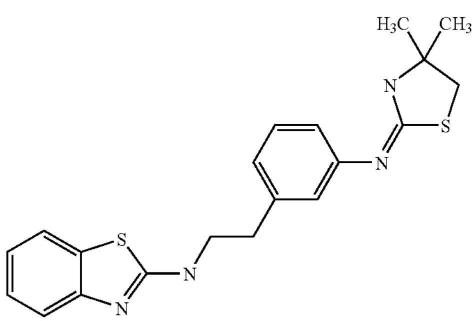 | C | 382 | 383.09 |
| 322 | 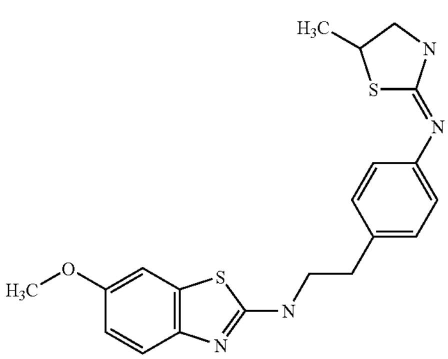 | C | 398 | 399.10 |

-continued
| Ex. No. | Structure | Ki | Exact Mass (g/mol) | Obs. Mass (M + 1) |
|---|---|---|---|---|
| 323 | 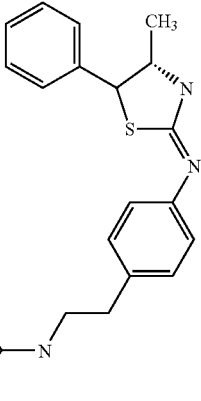 | C | 458 | 459.11 |
| 324 | 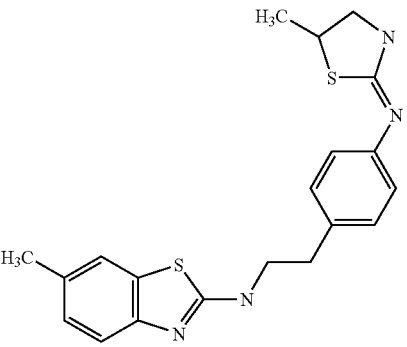 | C | 382 | 383.09 |
| 325 | 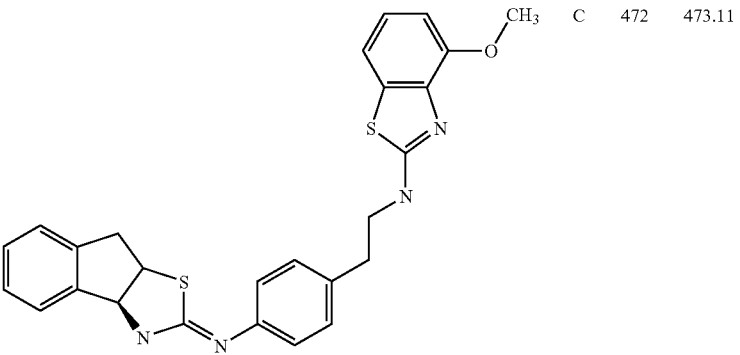 | C | 472 | 473.11 |

-continued

| Ex. No. | Structure | Ki | Exact Mass (g/mol) | Obs. Mass (M + 1) |
|---|---|---|---|---|
| 326 | 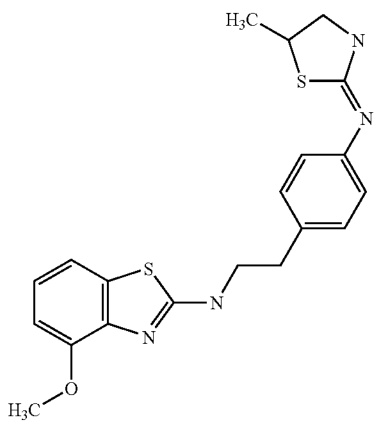 | C | 398 | 399.10 |
| 327 | 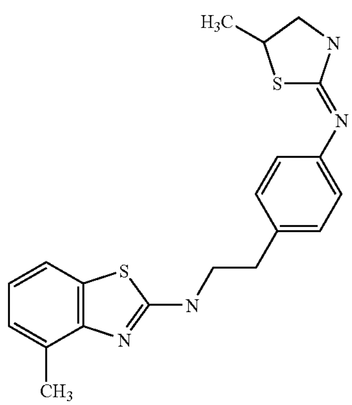 | C | 382 | 383.09 |
| 328 | 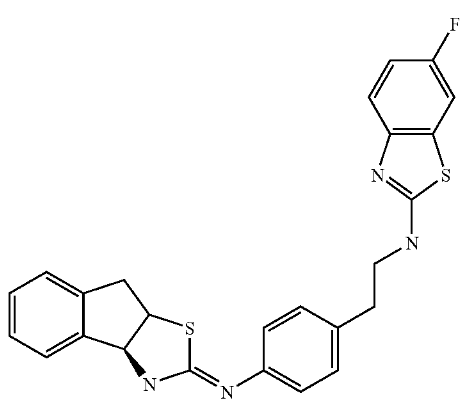 | A | 460 | 461.11 |

-continued

| Ex. No. | Structure | Ki | Exact Mass (g/mol) | Obs. Mass (M + 1) |
|---|---|---|---|---|
| 329 | 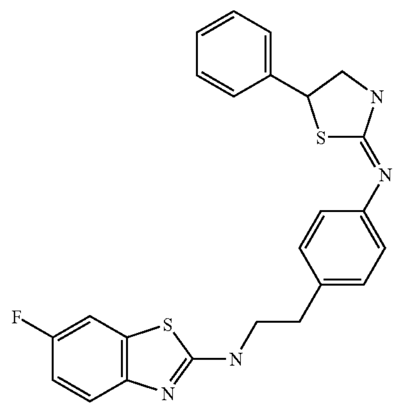 | C | 448 | 449.11 |
| 330 | 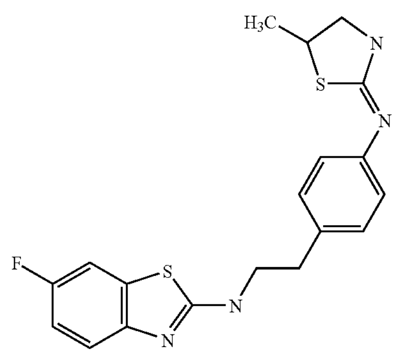 | C | 386 | 387.10 |
| 331 | 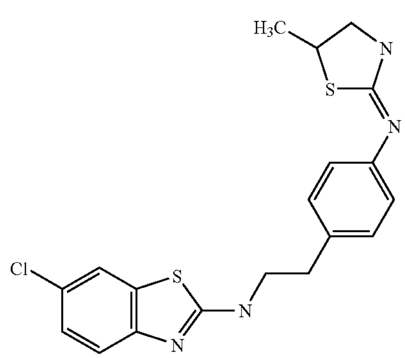 | C | 402 | 403.10 |

| Ex. No. | Structure | Ki | Exact Mass (g/mol) | Obs. Mass (M + 1) |
|---|---|---|---|---|
| 332 | 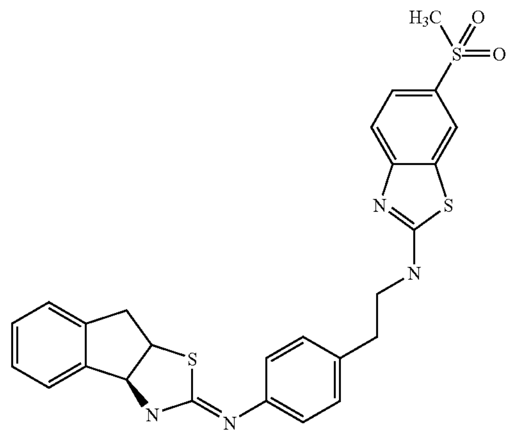 | C | 520 | 521.12 |
| 333 | 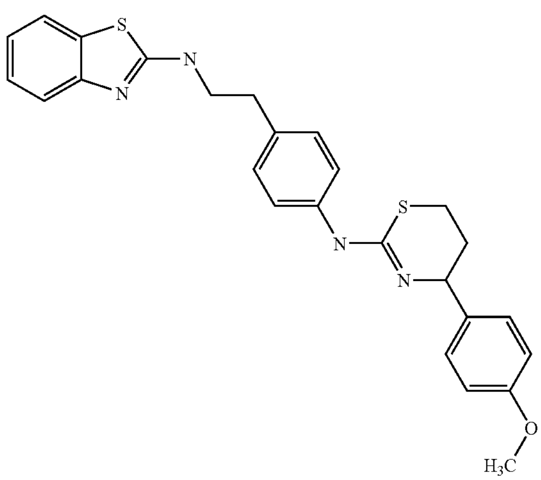 | A | 474 | 475.1 |
| 334 | 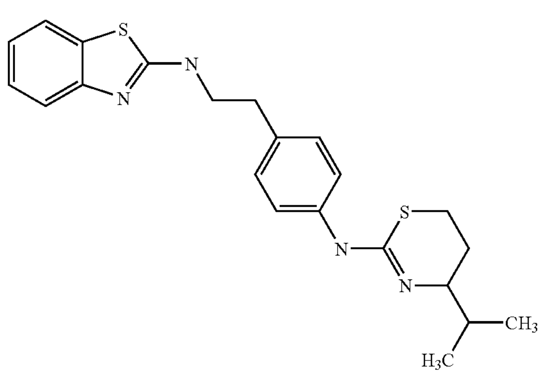 | A | 410 | 411.1 |

-continued

| Ex. No. | Structure | Ki | Exact Mass (g/mol) | Obs. Mass (M + 1) |
|---|---|---|---|---|
| 335 | 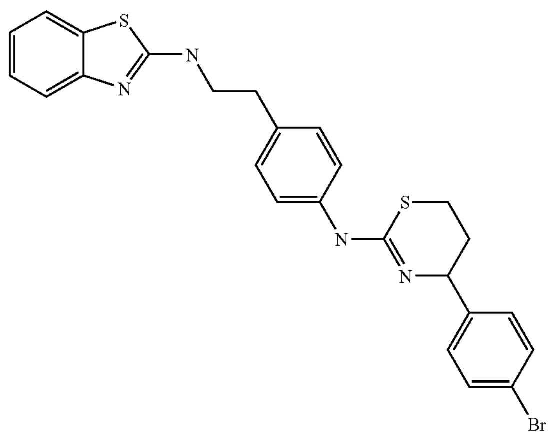 | A | 522 | 523 |
| 336 | 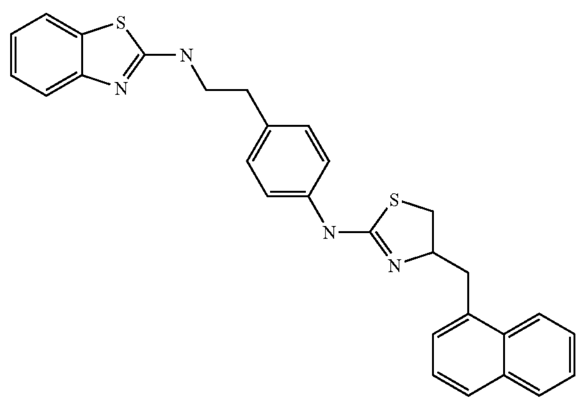 | C | 494 | 495.1 |
| 337 | 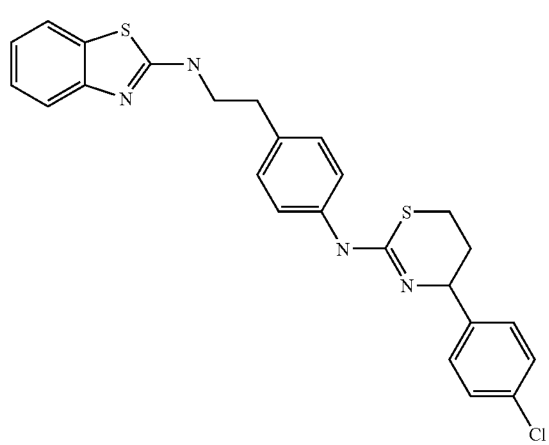 | A | 478 | 479.1 |

-continued
| Ex. No. | Structure | Ki | Exact Mass (g/mol) | Obs. Mass (M + 1) |
|---|---|---|---|---|
| 338 | 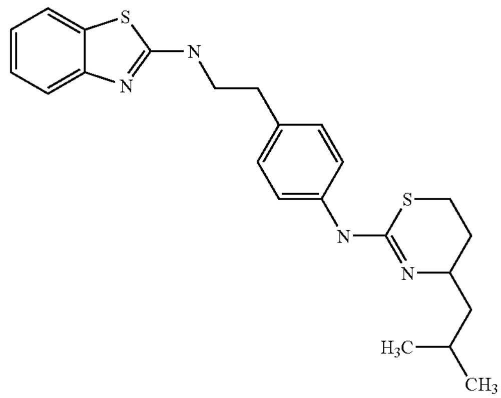 | A | 424 | 425.1 |
| 339 | 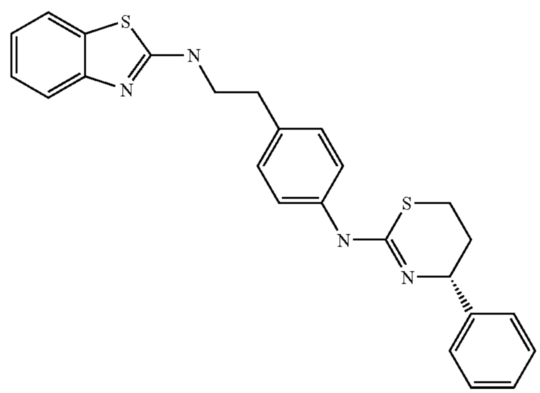 | A | 444 | 445.1 |
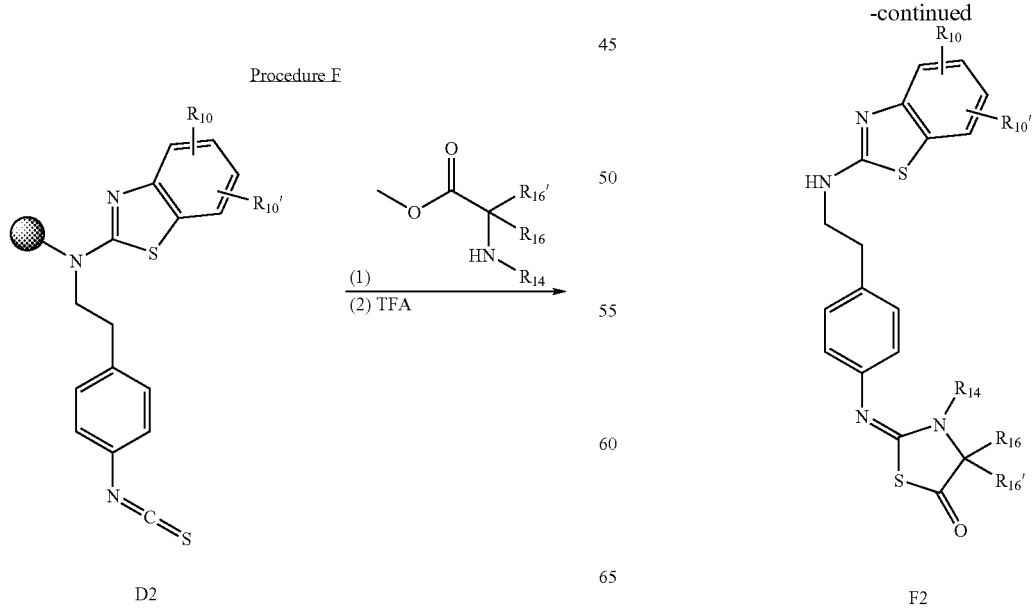
Procedure F
D2
F2

Procedure F, Step 1:
F2 ($R_{10}$ is H, $R_{10'}$ is H, $R_{14}$ is H, $R_{16}$ is H, and $R_{16'}$ is H) was synthesized by a Procedure similar to the one described for the synthesis of E2 ($R_{10}$ is H, $R_{10'}$ is H, $R_{14}$ is H, $R_{16}$ is H, $R_{16'}$ is H, Z is phenyl, and n is 2) (Procedure E, Step 1).
The following compounds were prepared using analogous methods:
| Ex. No. | Structure | Ki | Exact Mass (g/mol) | Obs. Mass (M + 1) |
|---|---|---|---|---|
| 340 | 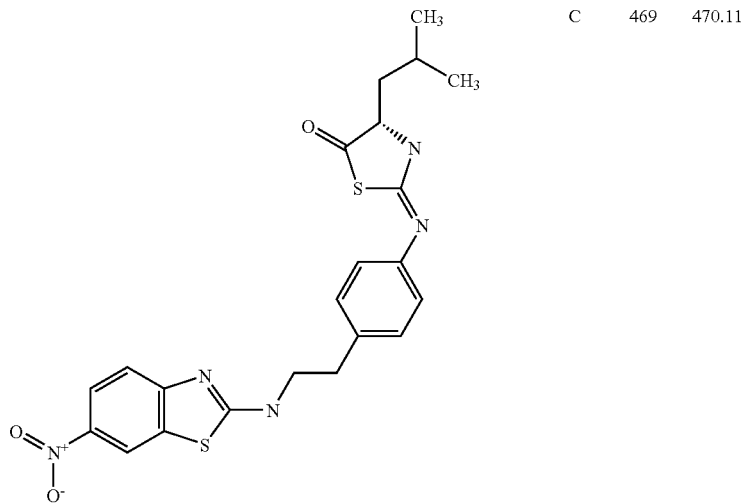 | C | 469 | 470.11 |
| 341 | 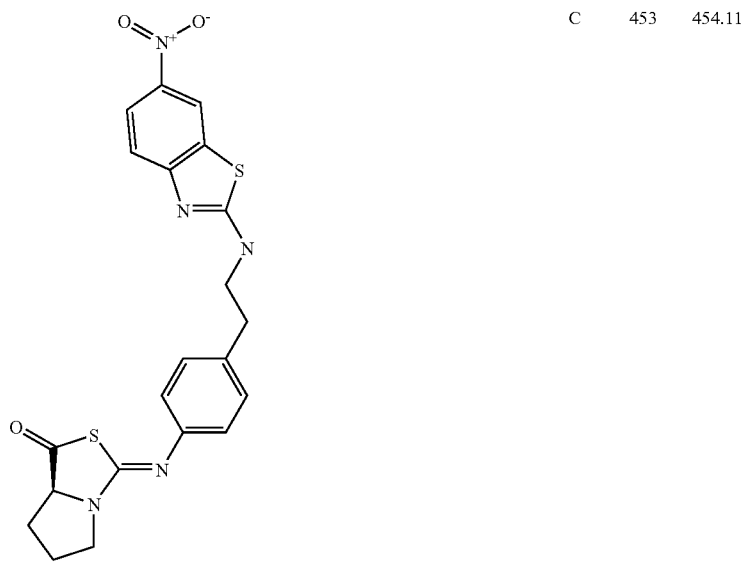 | C | 453 | 454.11 |

-continued

| Ex. No. | Structure | Ki | Exact Mass (g/mol) | Obs. Mass (M + 1) |
|---|---|---|---|---|
| 342 | 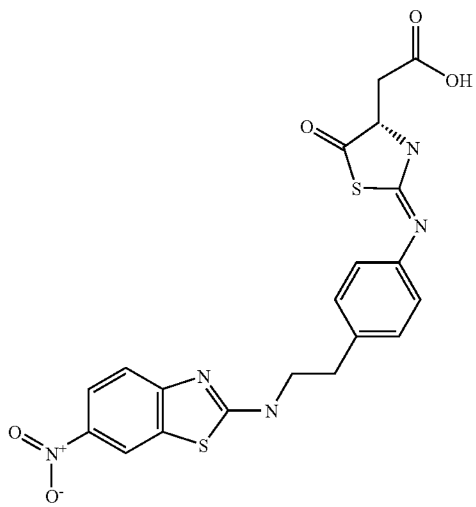 | C | 471 | 472.11 |
| 343 | 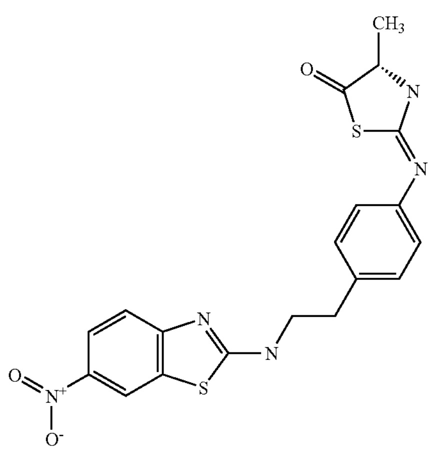 | C | 427 | 428.1 |
| 344 | 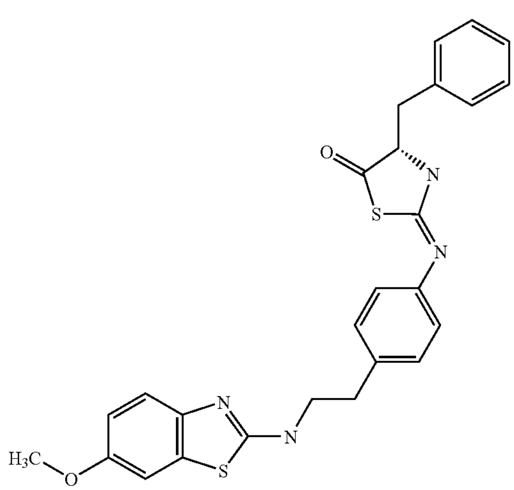 | C | 488 | 489.12 |

-continued
| Ex. No. | Structure | Ki | Exact Mass (g/mol) | Obs. Mass (M + 1) |
|---|---|---|---|---|
| 345 | 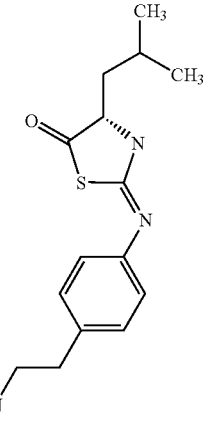 | C | 454 | 455.11 |
| 346 | 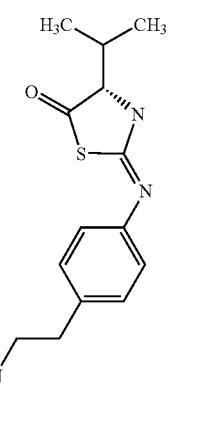 | C | 440 | 441.11 |
| 347 | 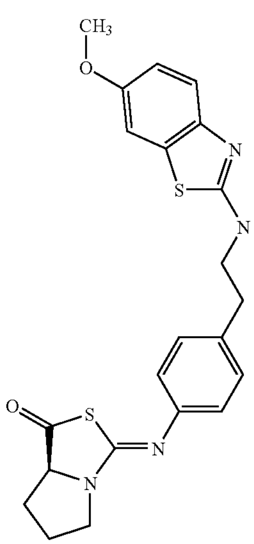 | C | 438 | 439.11 |

-continued

| Ex. No. | Structure | Ki | Exact Mass (g/mol) | Obs. Mass (M + 1) |
|---|---|---|---|---|
| 348 | 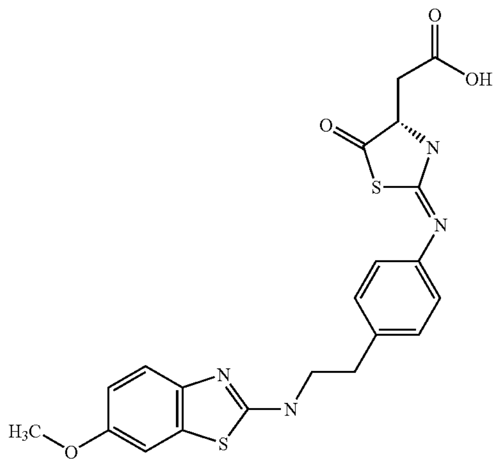 | C | 456 | 457.11 |
| 349 | 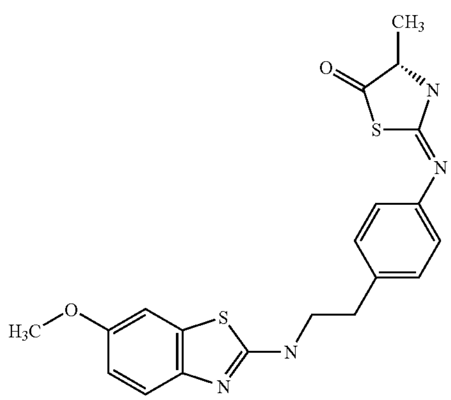 | C | 412 | 413.10 |
| 350 | 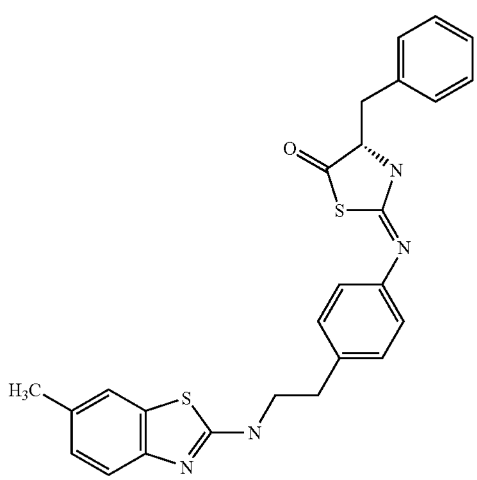 | C | 472 | 473.11 |

-continued

| Ex. No. | Structure | Ki | Exact Mass (g/mol) | Obs. Mass (M + 1) |
|---|---|---|---|---|
| 351 | 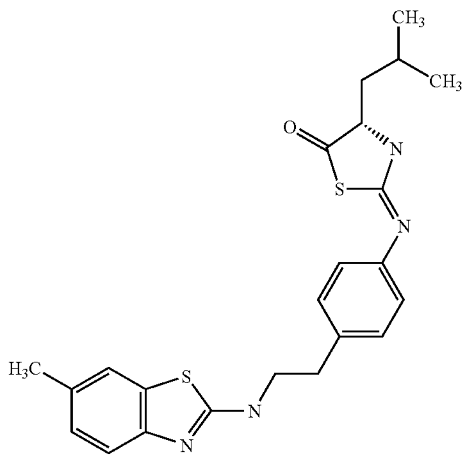 | C | 438 | 439.11 |
| 352 | 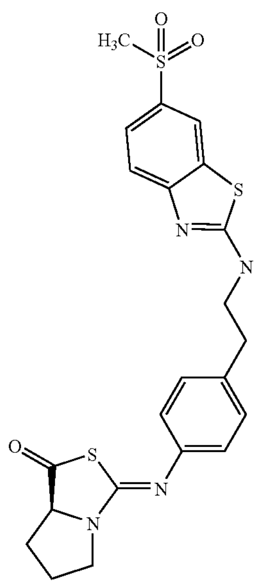 | C | 486 | 487.12 |
| 353 | 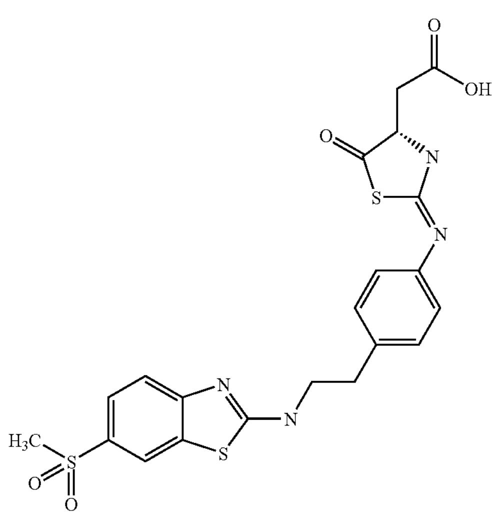 | C | 504 | 505.12 |

-continued

| Ex. No. | Structure | Ki | Exact Mass (g/mol) | Obs. Mass (M + 1) |
|---|---|---|---|---|
| 354 | 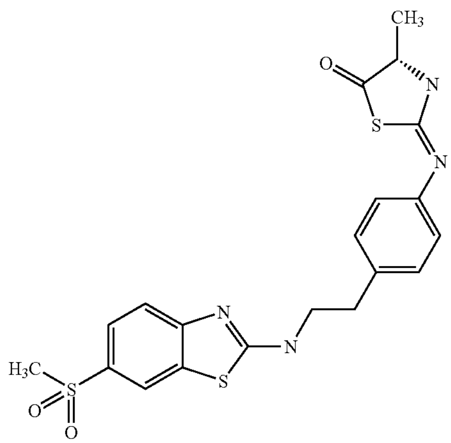 | C | 460 | 461.11 |
| 355 | 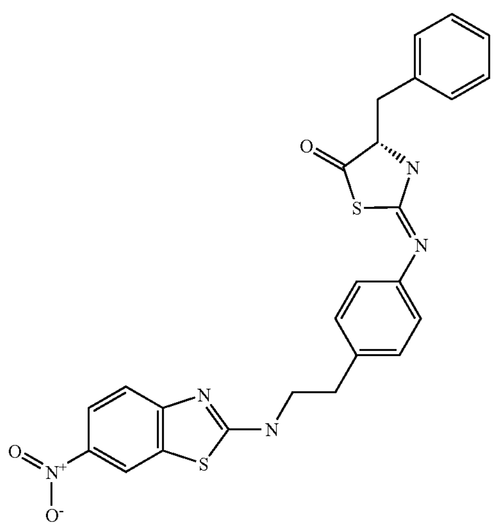 | C | 503 | 504.12 |
| 356 | 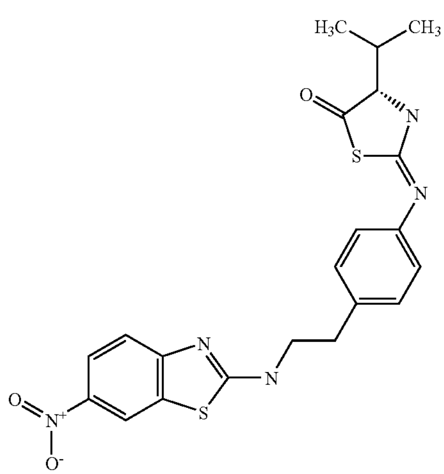 | C | 455 | 456.11 |

-continued
| Ex. No. | Structure | Ki | Exact Mass (g/mol) | Obs. Mass (M + 1) |
|---|---|---|---|---|
| 357 | 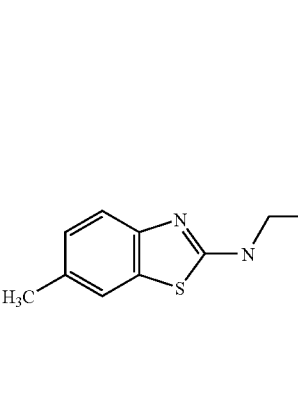 | B | 456 | 457.11 |
| 358 | 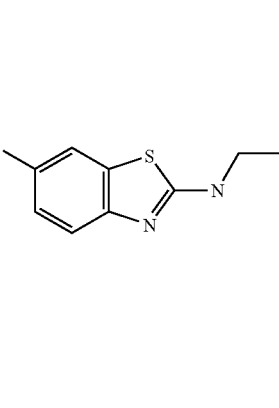 | C | 460 | 461.11 |
| 359 | 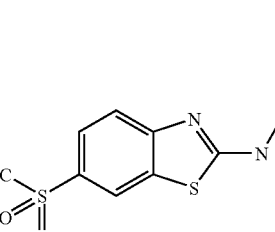 | C | 488 | 489.12 |

-continued
| Ex. No. | Structure | Ki | Exact Mass (g/mol) | Obs. Mass (M + 1) |
|---|---|---|---|---|
| 360 | 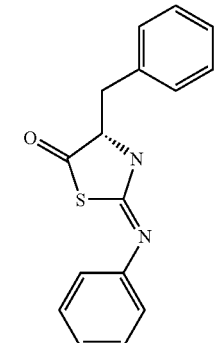 | C | 526 | 527.13 |
| 361 | 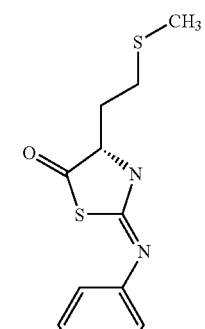 | C | 510 | 511.12 |
| 362 | 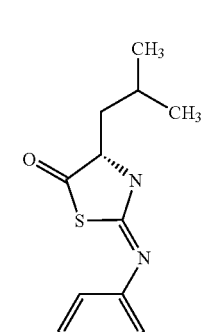 | C | 492 | 493.12 |

-continued
| Ex. No. | Structure | Ki | Exact Mass (g/mol) | Obs. Mass (M + 1) |
|---|---|---|---|---|
| 363 | 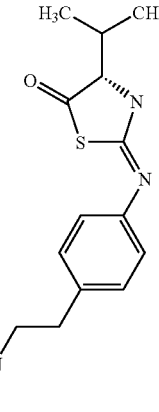 | C | 478 | 479.11 |
| 364 | 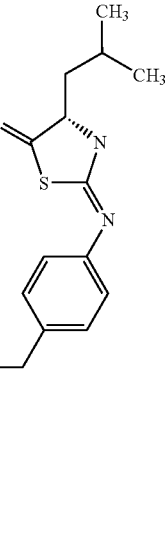 | C | 454 | 455.11 |
| 365 | 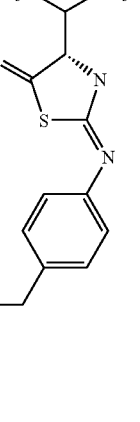 | C | 440 | 441.11 |

-continued
| Ex. No. | Structure | Ki | Exact Mass (g/mol) | Obs. Mass (M + 1) |
|---|---|---|---|---|
| 366 | 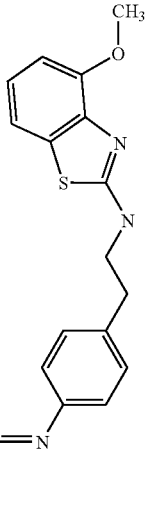 | C | 438 | 439.11 |
| 367 | 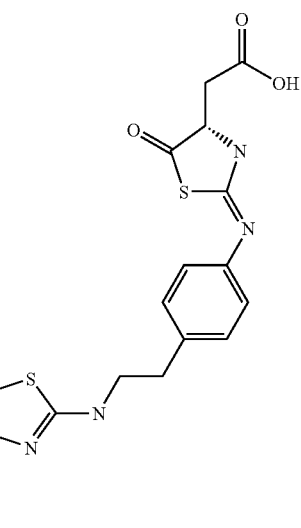 | C | 456 | 457.11 |
| 368 | 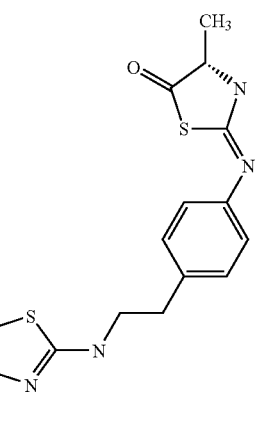 | C | 412 | 413.1 |

-continued

| Ex. No. | Structure | Ki | Exact Mass (g/mol) | Obs. Mass (M + 1) |
|---|---|---|---|---|
| 369 | 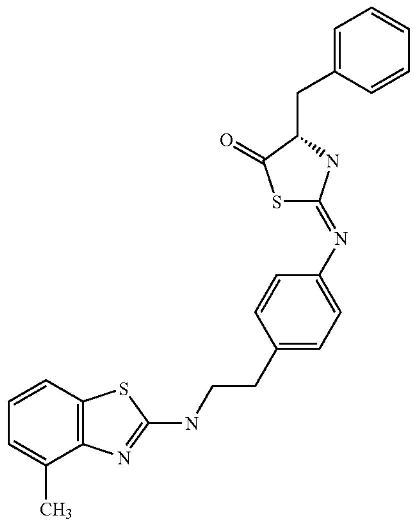 | C | 472 | 473.11 |
| 370 | 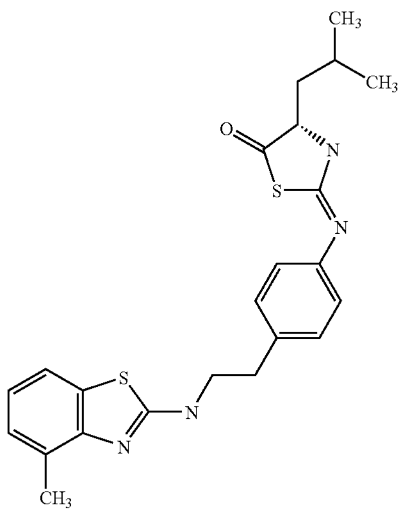 | C | 438 | 439.11 |
| 371 | 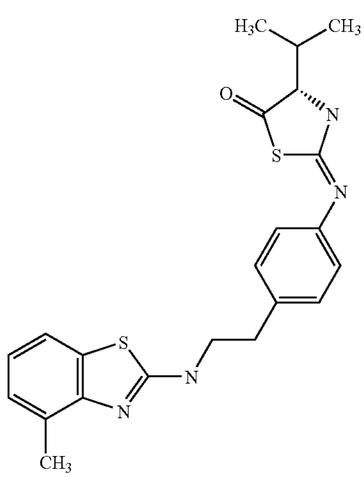 | C | 424 | 425.1 |

-continued

| Ex. No. | Structure | Ki | Exact Mass (g/mol) | Obs. Mass (M + 1) |
|---|---|---|---|---|
| 372 | 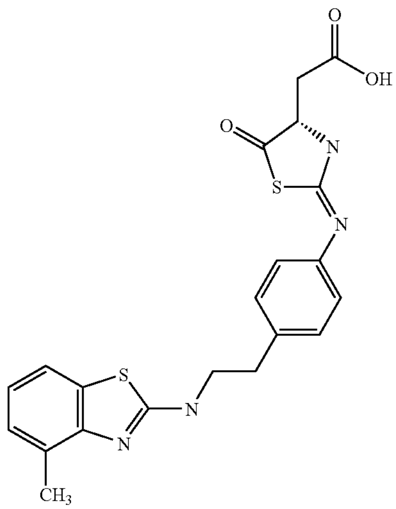 | C | 440 | 441.11 |
| 373 | 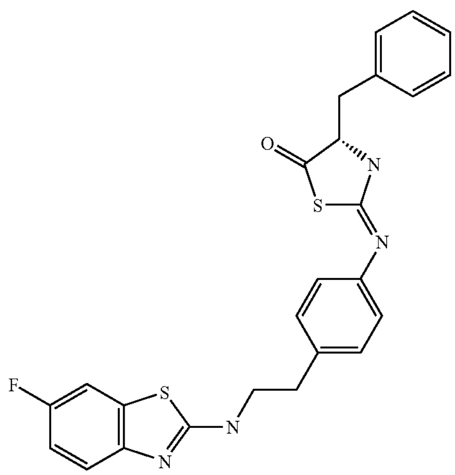 | C | 476 | 477.11 |
| 374 | 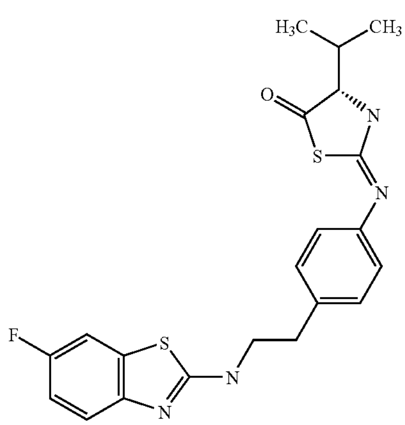 | C | 428 | 429.10 |

| Ex. No. | Structure | Ki | Exact Mass (g/mol) | Obs. Mass (M + 1) |
|---|---|---|---|---|
| 375 | 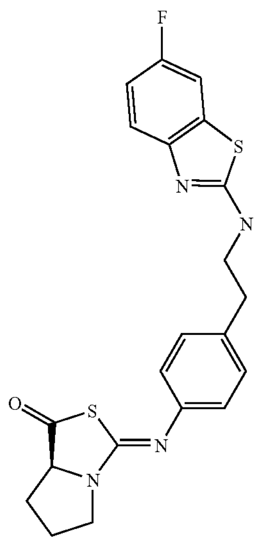 | C | 426 | 427.10 |
| 376 | 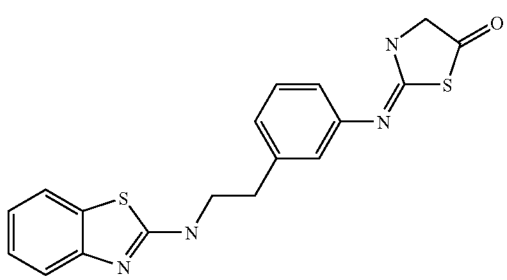 | C | 368 | 369.09 |
| 377 | 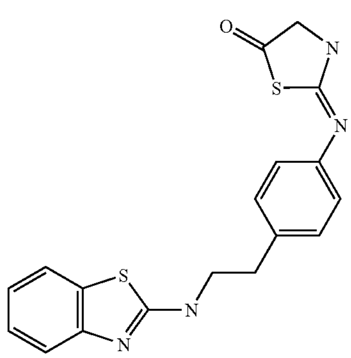 | C | 368 | 369.09 |

-continued

| Ex. No. | Structure | Ki | Exact Mass (g/mol) | Obs. Mass (M + 1) |
|---|---|---|---|---|
| 378 | 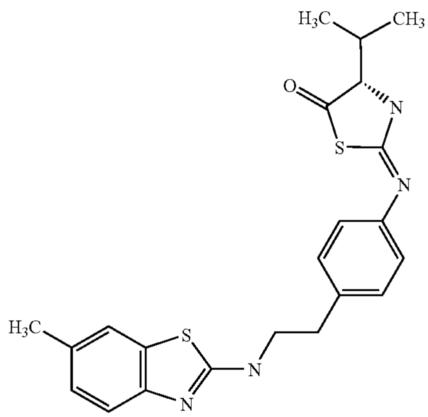 | C | 424 | 425.10 |
| 379 | 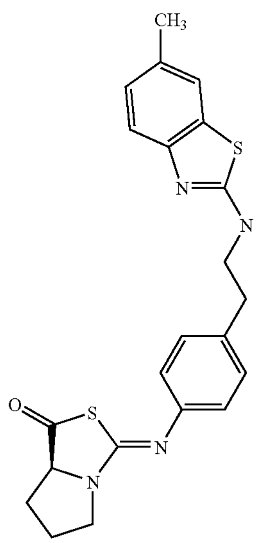 | C | 422 | 423.10 |
| 380 | 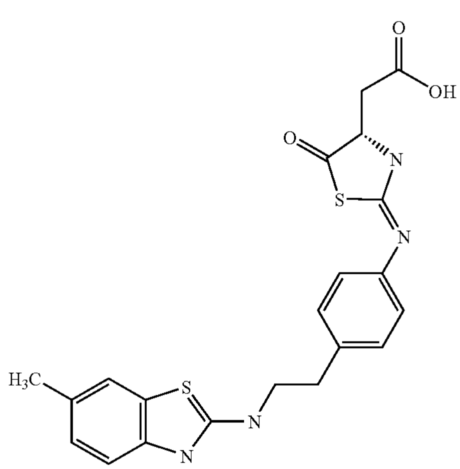 | C | 440 | 441.11 |

-continued

| Ex. No. | Structure | Ki | Exact Mass (g/mol) | Obs. Mass (M + 1) |
|---|---|---|---|---|
| 381 | 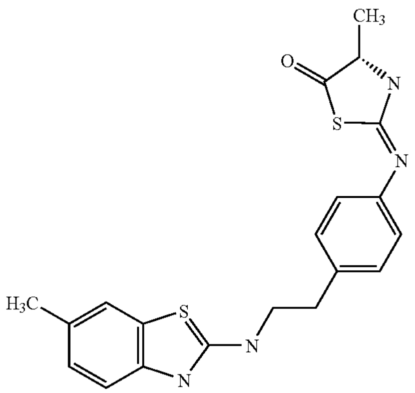 | C | 396 | 397.10 |
| 382 | 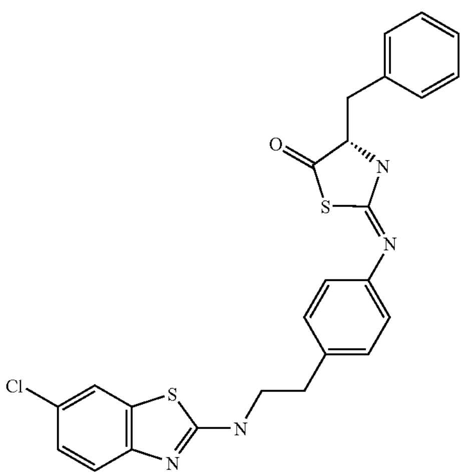 | C | 492 | 493.12 |
| 383 | 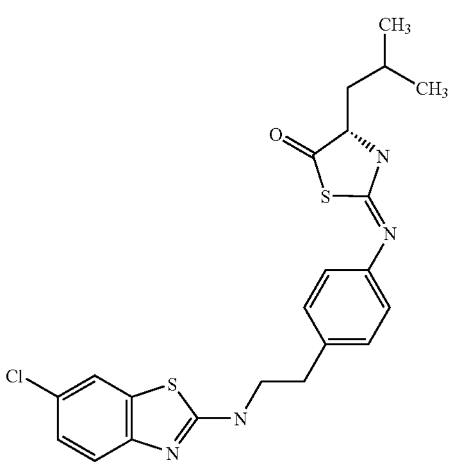 | C | 458 | 459.11 |

-continued

| Ex. No. | Structure | Ki | Exact Mass (g/mol) | Obs. Mass (M + 1) |
|---|---|---|---|---|
| 384 | 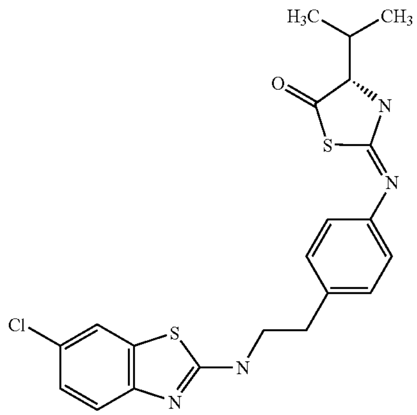 | C | 444 | 445.11 |
| 385 | 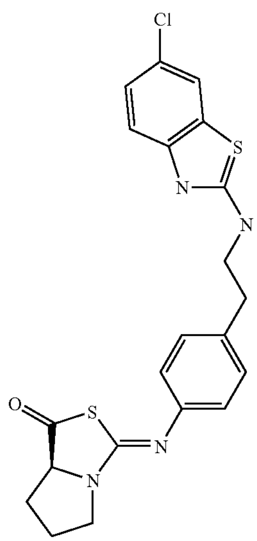 | C | 442 | 443.11 |
| 386 | 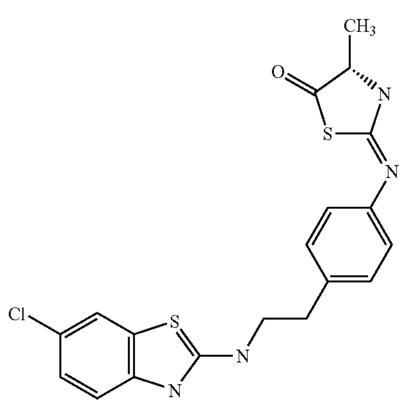 | C | 416 | 417.10 |

-continued

| Ex. No. | Structure | Ki | Exact Mass (g/mol) | Obs. Mass (M + 1) |
|---|---|---|---|---|
| 387 | 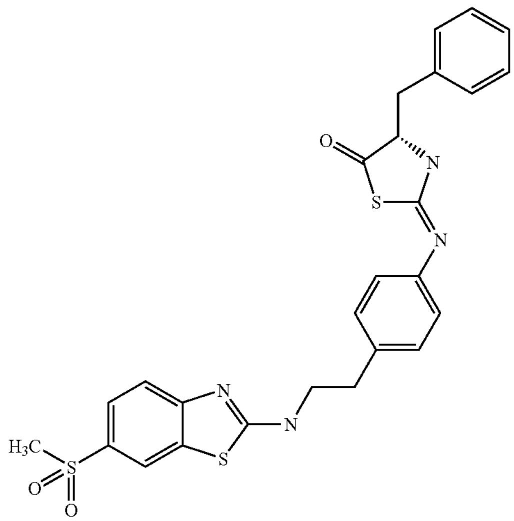 | C | 536 | 537.13 |
| 388 | 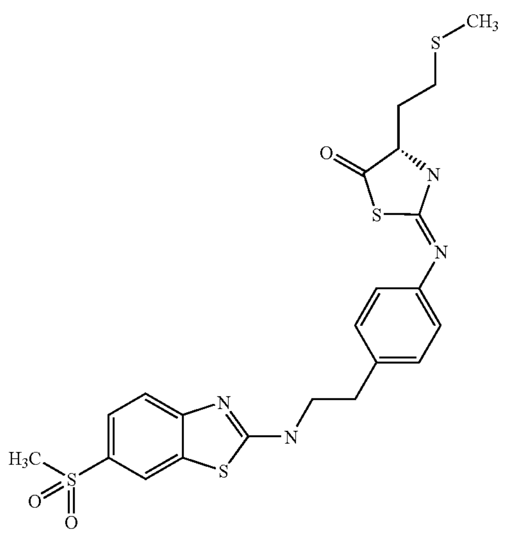 | C | 520 | 521.12 |
| 389 | 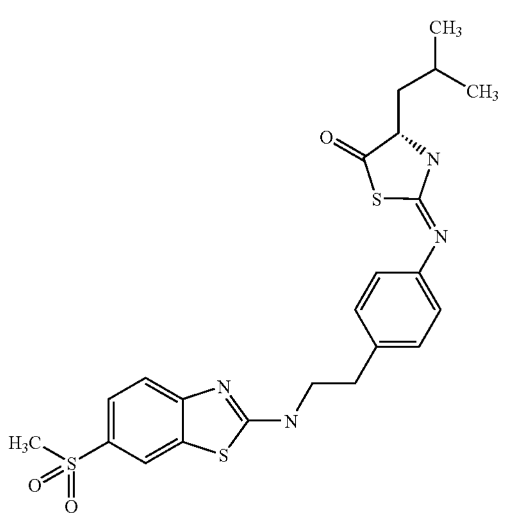 | C | 502 | 503.12 |

-continued
| Ex. No. | Structure | Ki | Exact Mass (g/mol) | Obs. Mass (M + 1) |
|---|---|---|---|---|
| 390 | 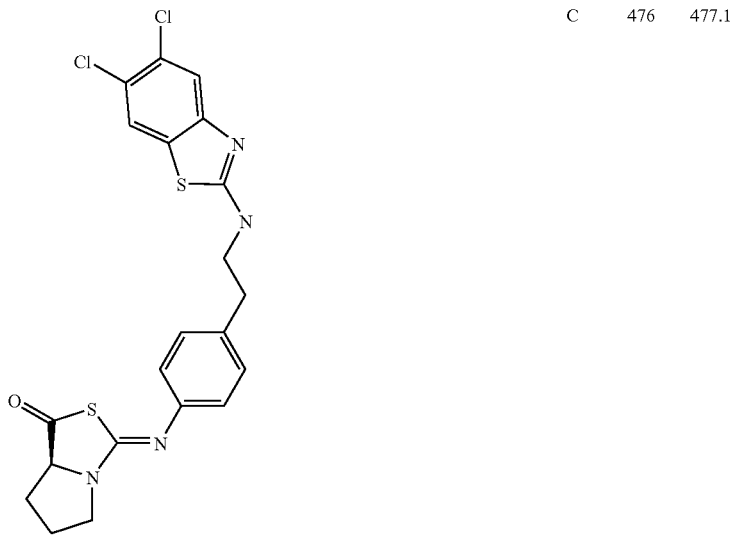 | C | 476 | 477.1 |
| 391 | 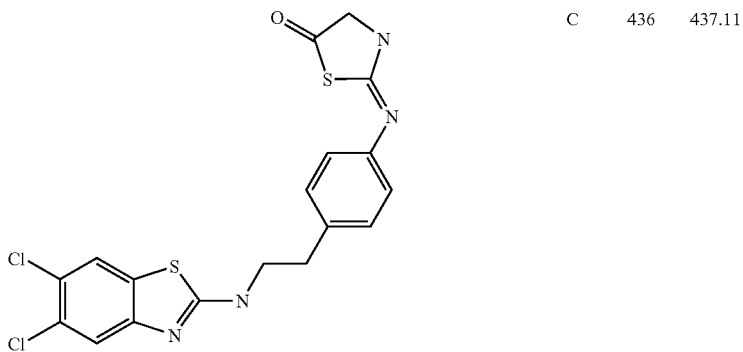 | C | 436 | 437.11 |
| 392 | 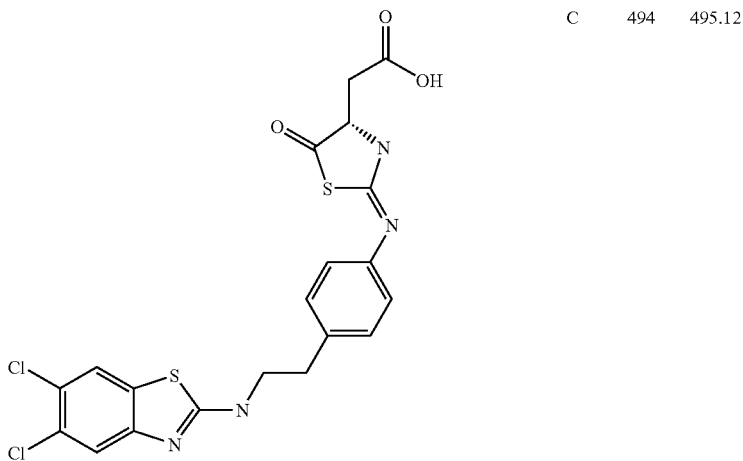 | C | 494 | 495.12 |

| Ex. No. | Structure | Ki | Exact Mass (g/mol) | Obs. Mass (M + 1) |
|---|---|---|---|---|
| 393 | 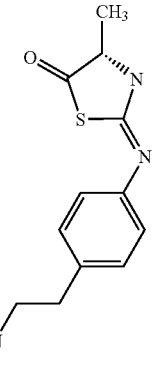 | C | 450 | 451.11 |
| 394 | 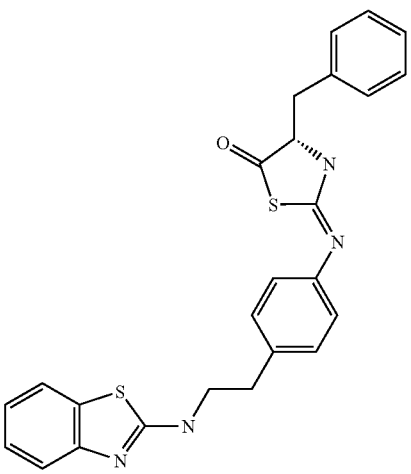 | C | 458 | 459.11 |
| 395 | 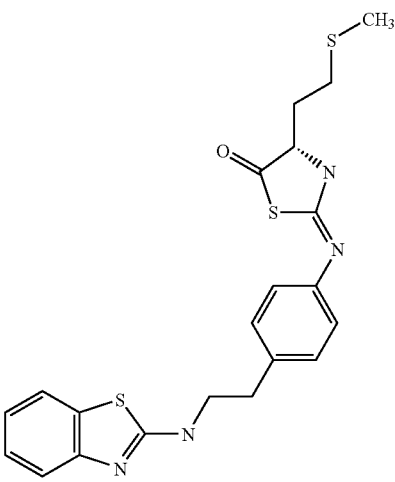 | C | 442 | 443.11 |

| Ex. No. | Structure | Ki | Exact Mass (g/mol) | Obs. Mass (M + 1) |
|---|---|---|---|---|
| 396 | 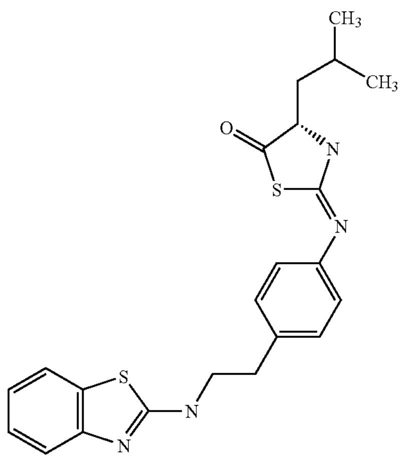 | C | 424 | 425.10 |
| 397 | 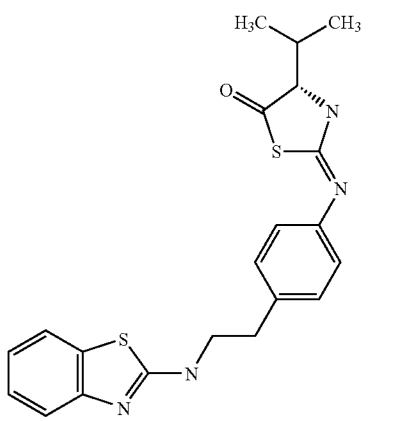 | C | 410 | 411.10 |
| 398 | 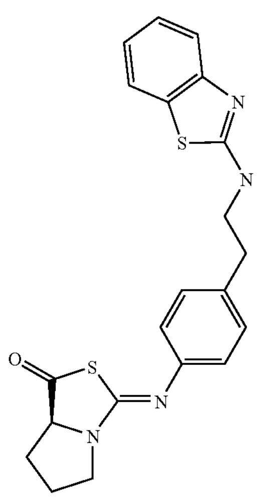 | C | 408 | 409.10 |

| Ex. No. | Structure | Ki | Exact Mass (g/mol) | Obs. Mass (M + 1) |
|---|---|---|---|---|
| 399 | 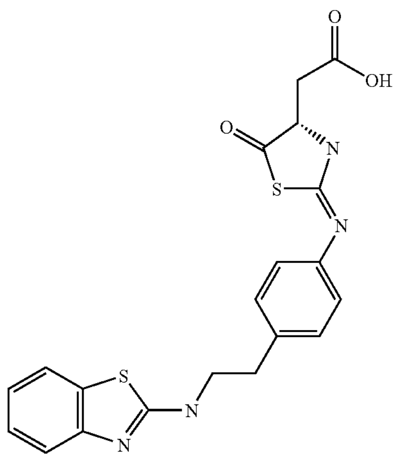 | C | 426 | 427.10 |
| 400 | 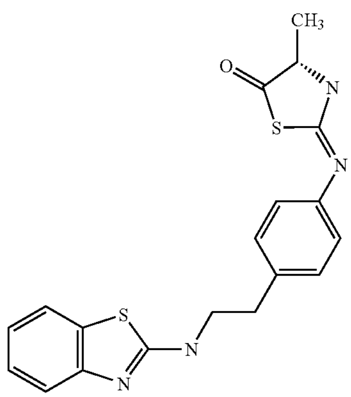 | C | 382 | 383.09 |
| 401 | 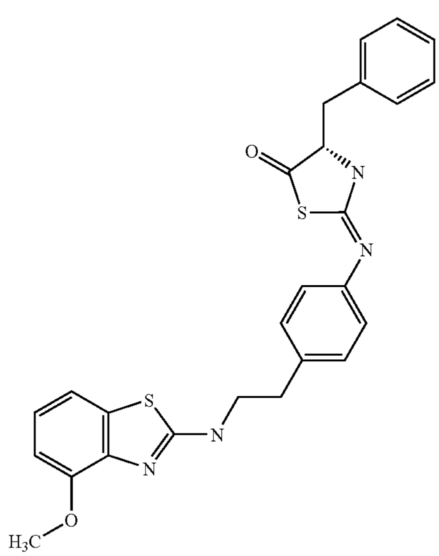 | C | 488 | 489.12 |

| Ex. No. | Structure | Ki | Exact Mass (g/mol) | Obs. Mass (M + 1) |
|---|---|---|---|---|
| 402 | 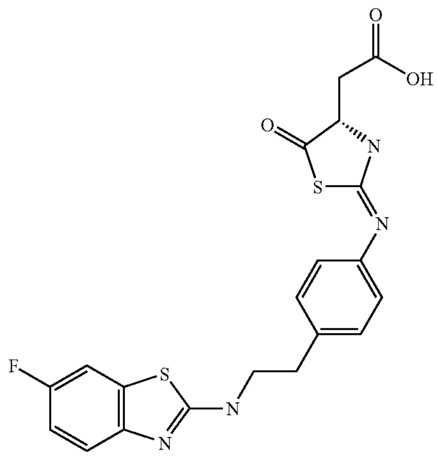 | C | 444 | 445.11 |
| 403 | 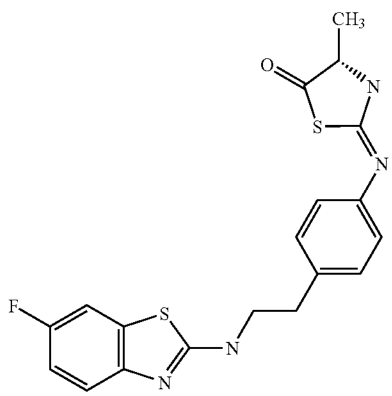 | C | 400 | 401.10 |
| 404 | 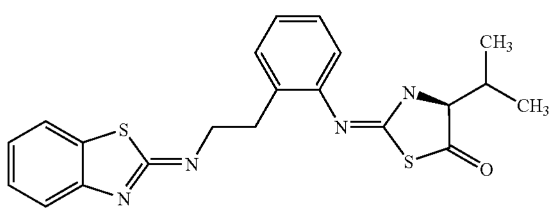 | C | 410 | 411.10 |
| 405 | 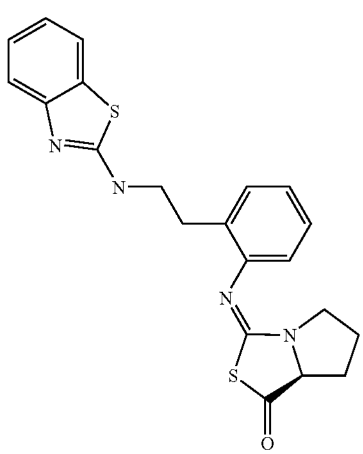 | C | 408 | 409.10 |

-continued

| Ex. No. | Structure | Ki | Exact Mass (g/mol) | Obs. Mass (M + 1) |
|---|---|---|---|---|
| 406 | 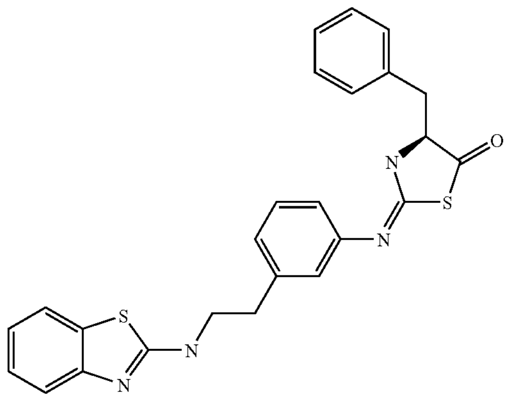 | C | 458 | 459.11 |
| 407 | 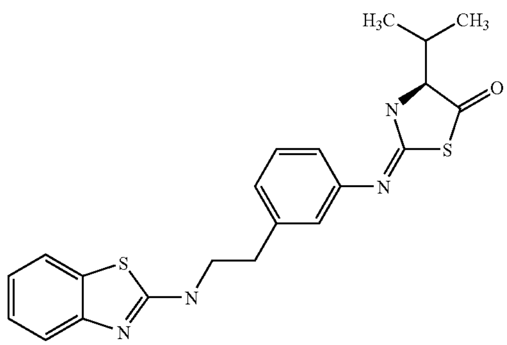 | C | 410 | 411.10 |
| 408 | 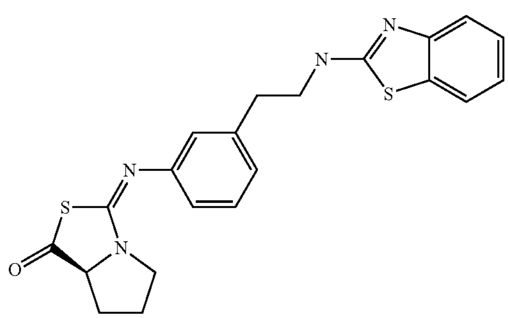 | C | 408 | 409.10 |
| 409 | 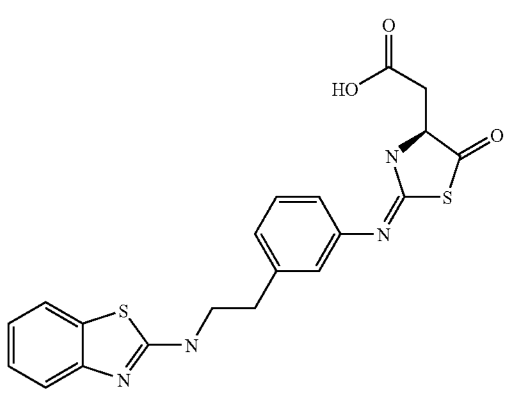 | C | 426 | 427.10 |

-continued

| Ex. No. | Structure | Ki | Exact Mass (g/mol) | Obs. Mass (M + 1) |
|---|---|---|---|---|
| 410 | 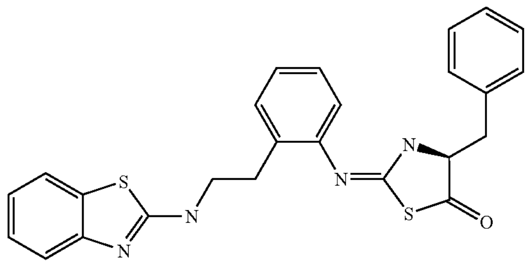 | C | 458 | 459.11 |
| 411 | 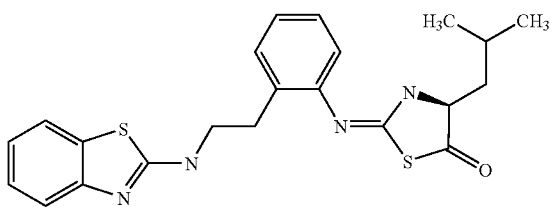 | C | 424 | 425.10 |
| 412 | 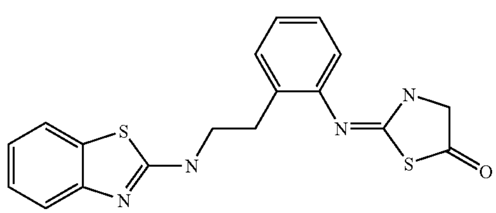 | C | 368 | 369.09 |
| 413 | 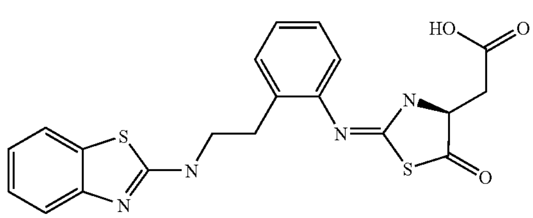 | C | 426 | 427.10 |

-continued

| Ex. No. | Structure | Ki | Exact Mass (g/mol) | Obs. Mass (M + 1) |
|---|---|---|---|---|
| 414 | 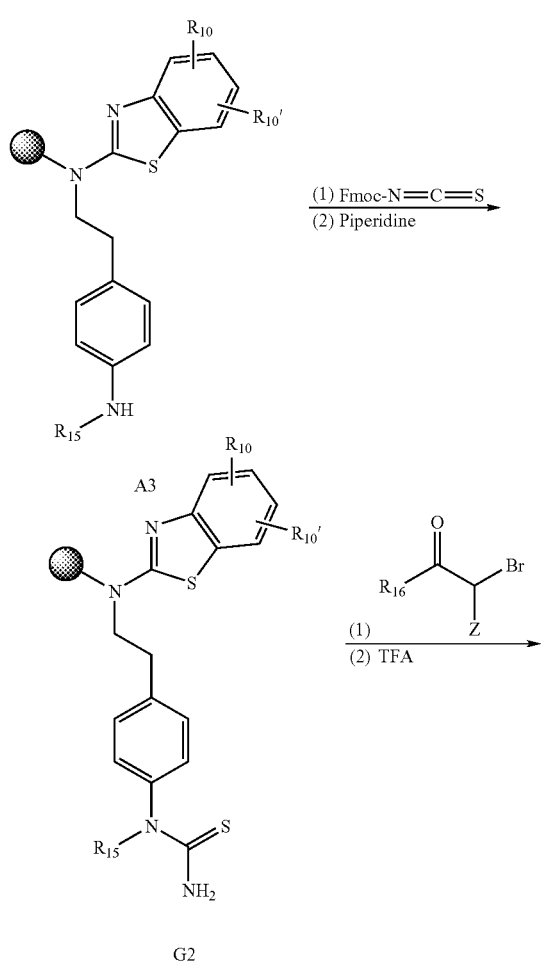 | C | 487 | 488.12 |

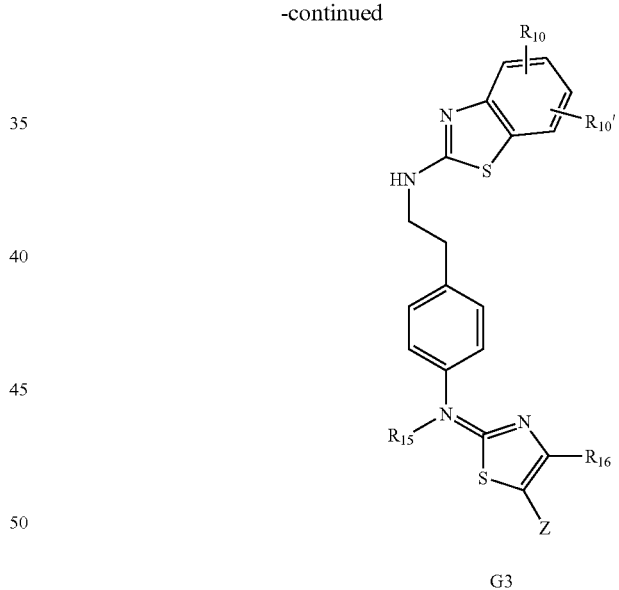

Procedure G, Step 1:

Fmoc thiocyanate (1.25 g, 4.45 mmol) was added to resin A3 ($R_{10}$ is H, $R_{10'}$ is H, and $R_{15}$ is H) (1 g). The reaction was shaken overnight. The resin was washed with THF (5×) and DCM (5×). The resin was treated with 20% piperidine in DMF (20 min×3). The resin was washed with DMF (3×), THF (3×), CH$_3$OH (3×) and DCM (3×) and dried to give G2 ($R_{10}$ is H, $R_{10'}$ is H and $R_{15}$ is H).

Procedure G, Step 2:

Pyridine (0.5 mL, 6.2 mmol) was added to preswelled resin G2 ($R_{10}$ is H, $R_{10'}$ is H, and $R_{15}$ is H) (60 mg). 2-Bromoacetophenone (100 mg, 0.50 mmol) was dissolved in DCM (0.5 mL) and added to the suspension. The reaction was shaken overnight. The resin was washed with DMF (3×), CH$_3$OH (3×), 10% HOAc in a 3:1 solvent mixture of DCM:CH$_3$OH (2×10 min), CH$_3$OH and THF (alternating wash cycle 3×), CH$_3$OH (2×) and DCM (4×). The resin was cleaved with 20% TFA in DCM for 1.5 h and the filtrate was concentrated to afford G3 ($R_{10}$ is H, $R_{10}$ is H, $R_{15}$ is H, $R_{16}$ is phenyl, and Z is H).

The following compounds were prepared using analogous methods:

| Ex. No. | Structure | Ki | Exact Mass (g/mol) | Obs. Mass (M + 1) |
|---|---|---|---|---|
| 415 | 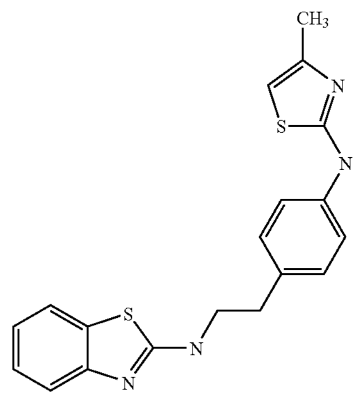 | C | 366 | 367.09 |
| 416 | 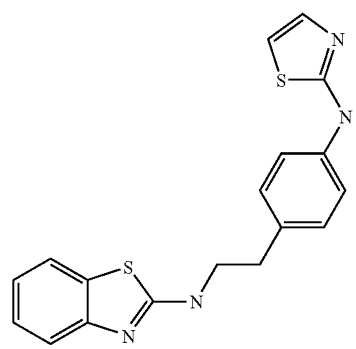 | C | 352 | 353.09 |
| 417 | 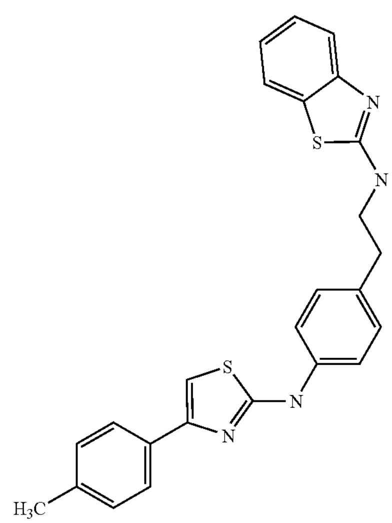 | C | 442 | 443.11 |

-continued
| Ex. No. | Structure | Ki | Exact Mass (g/mol) | Obs. Mass (M + 1) |
|---|---|---|---|---|
| 418 | 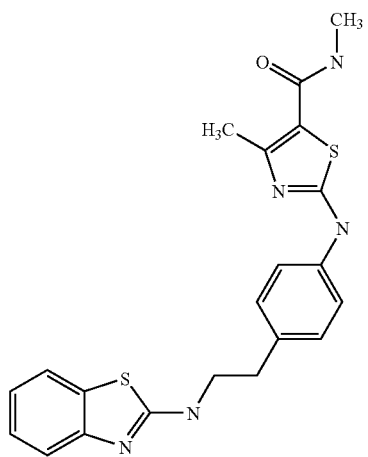 | C | 423 | 424.1 |
| 419 | 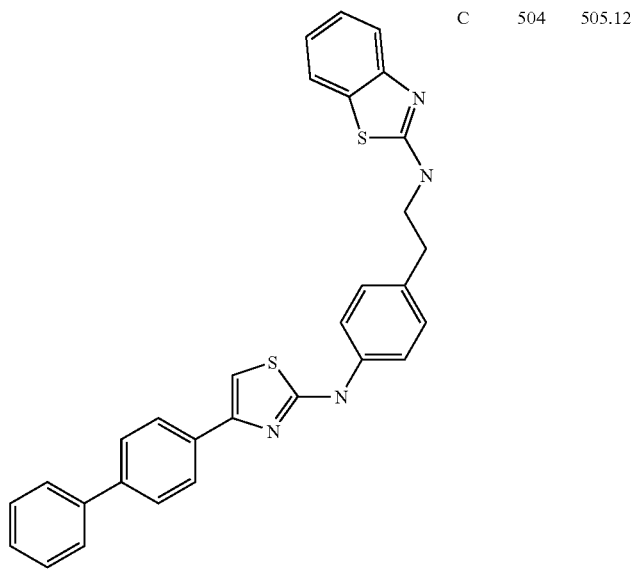 | C | 504 | 505.12 |
| 420 | 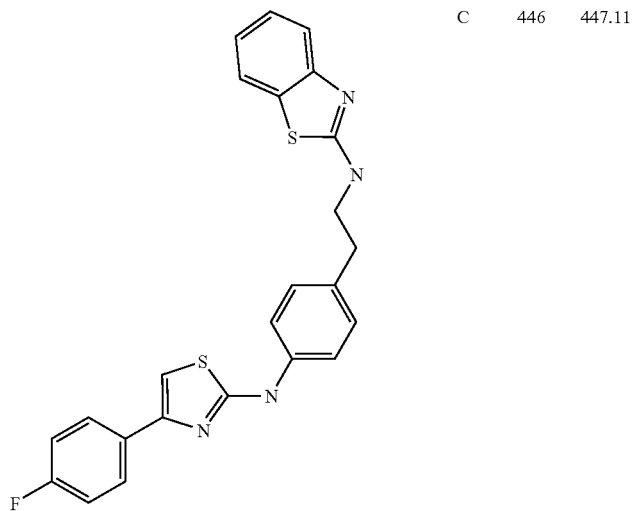 | C | 446 | 447.11 |

-continued

| Ex. No. | Structure | Ki | Exact Mass (g/mol) | Obs. Mass (M + 1) |
|---|---|---|---|---|
| 421 | 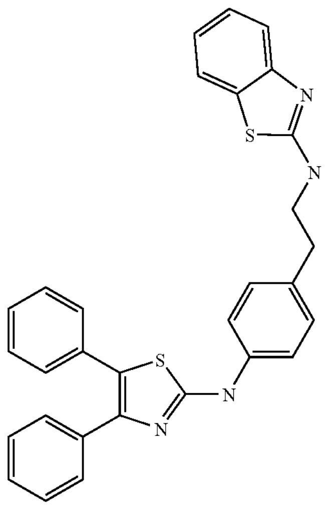 | C | 504 | 505.12 |
| 422 | 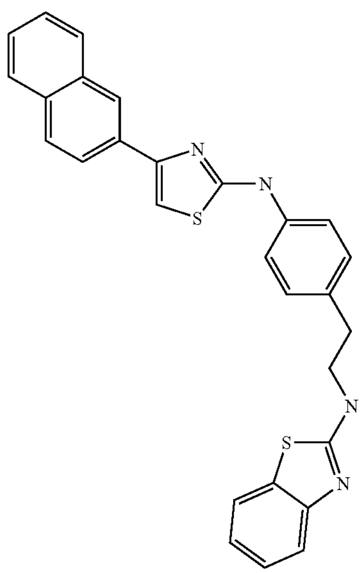 | C | 478 | 479.11 |
| 423 | 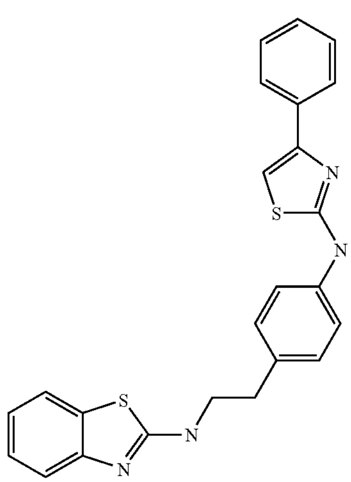 | C | 428 | 429.1 |

-continued
| Ex. No. | Structure | Ki | Exact Mass (g/mol) | Obs. Mass (M + 1) |
|---|---|---|---|---|
| 424 | 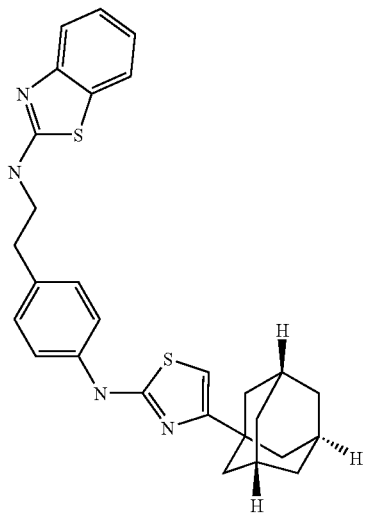 | C | 486 | 487.12 |
| 425 | 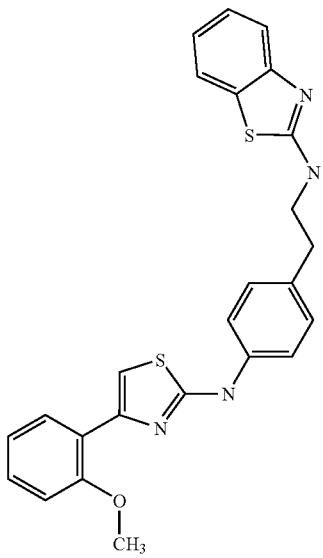 | C | 458 | 459.11 |

-continued
| Ex. No. | Structure | Ki | Exact Mass (g/mol) | Obs. Mass (M + 1) |
|---|---|---|---|---|
| 426 | 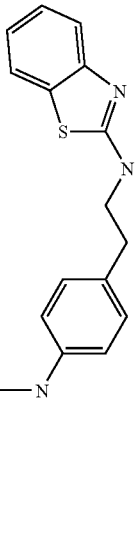 | C | 488 | 489.12 |
| 427 | 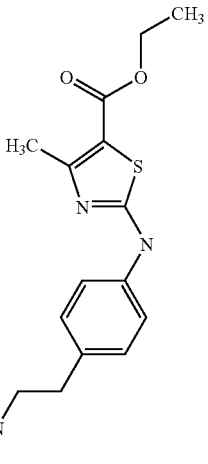 | C | 438 | 439.11 |
| 428 | 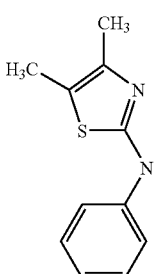 | C | 380 | 381.09 |

-continued

| Ex. No. | Structure | Ki | Exact Mass (g/mol) | Obs. Mass (M + 1) |
|---|---|---|---|---|
| 429 | 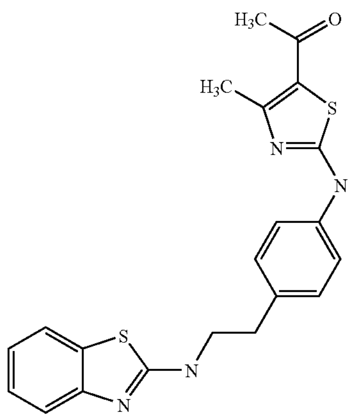 | C | 408 | 409.1 |
| 430 | 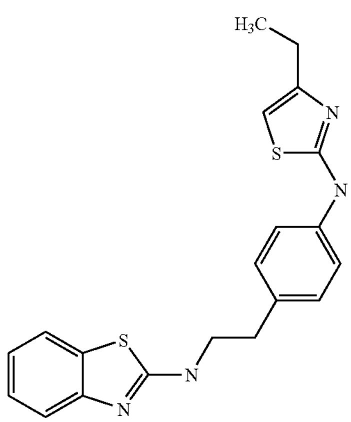 | C | 380 | 381.09 |
| 431 | 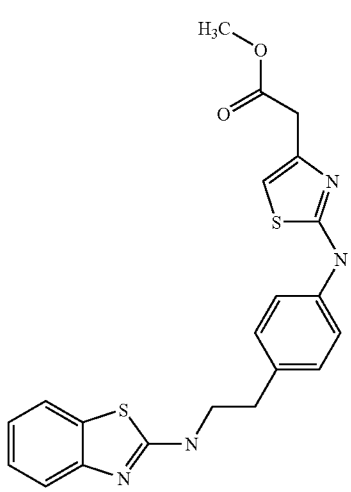 | C | 424 | 425.1 |

-continued

| Ex. No. | Structure | Ki | Exact Mass (g/mol) | Obs. Mass (M + 1) |
|---|---|---|---|---|
| 432 | 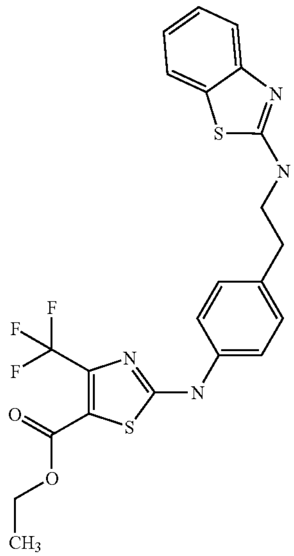 | C | 492 | 493.12 |
| 433 | 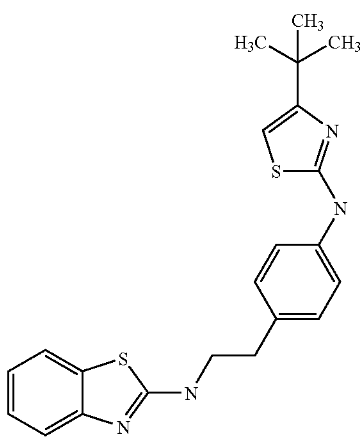 | C | 408 | 409.1 |
| 434 | 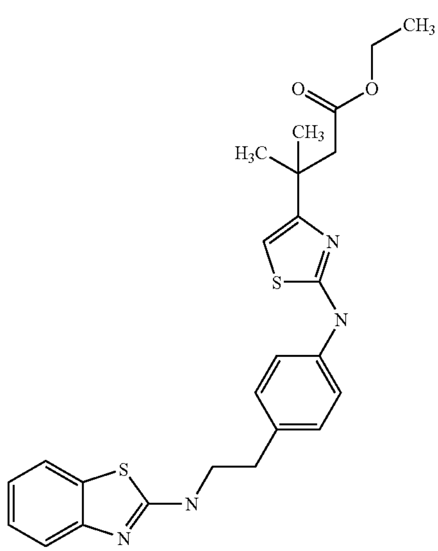 | C | 480 | 481.12 |

-continued

| Ex. No. | Structure | Ki | Exact Mass (g/mol) | Obs. Mass (M + 1) |
|---|---|---|---|---|
| 435 | 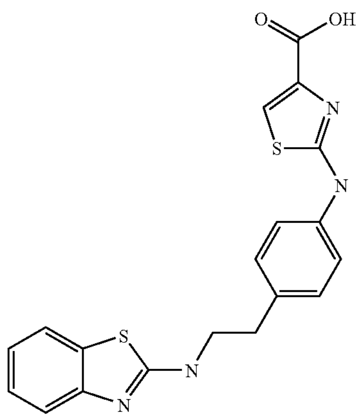 | C | 396 | 397.1 |
| 436 | 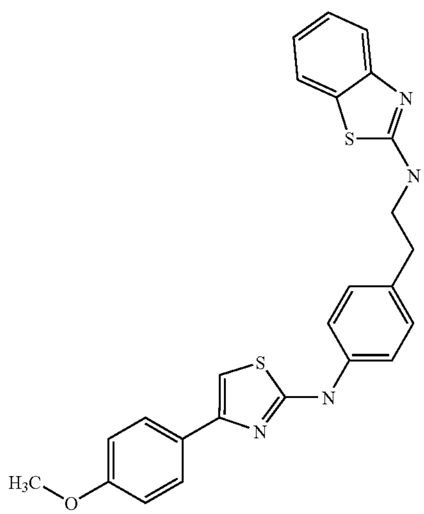 | C | 458 | 459.11 |
| 437 | 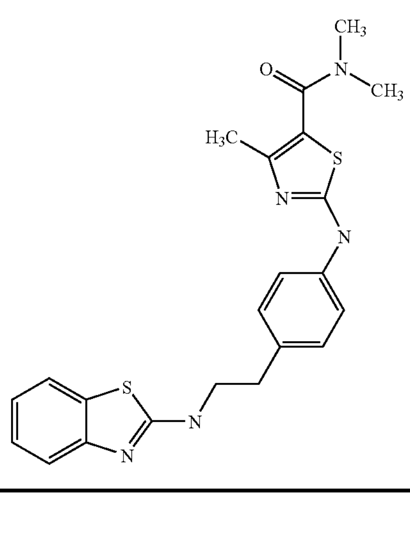 | C | 437 | 438.11 |

Procedure H
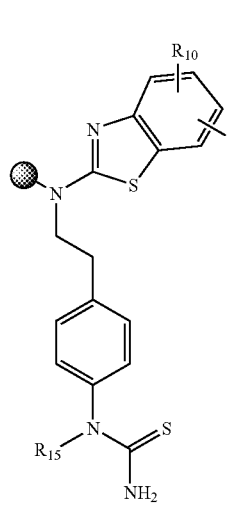
G2
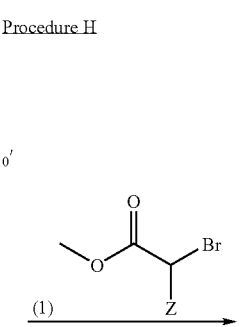
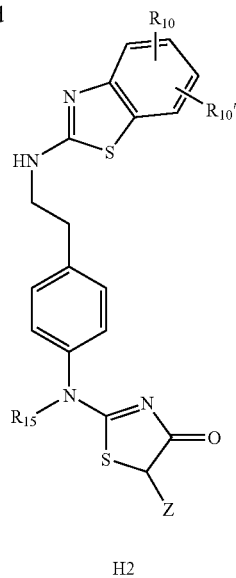
H2
Procedure H, Step 1:
H2 ($R_{10}$ is H, $R_{10'}$ is H, $R_{15}$ is H, and Z is phenyl) was prepared by a procedure similar to the one described for the synthesis of G3 ($R_{10}$ is H, $R_{10'}$ is H, $R_{15}$ is H, $R_{16}$ is phenyl, and Z is H) (Procedure G, Step 2).
The following compounds were prepared using analogous methods:
| Ex. No. | Structure | Ki | Exact Mass (g/mol) | Observed Mass (M + 1) |
|---|---|---|---|---|
| 439 | 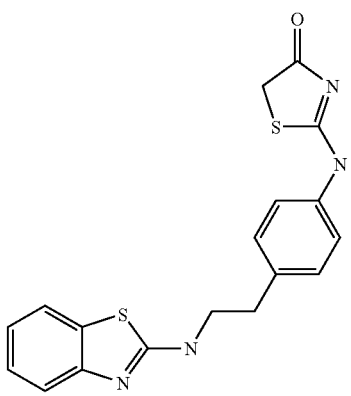 | C | 368 | 369.09 |

-continued

| Ex. No. | Structure | Ki | Exact Mass (g/mol) | Observed Mass (M + 1) |
|---|---|---|---|---|
| 440 | 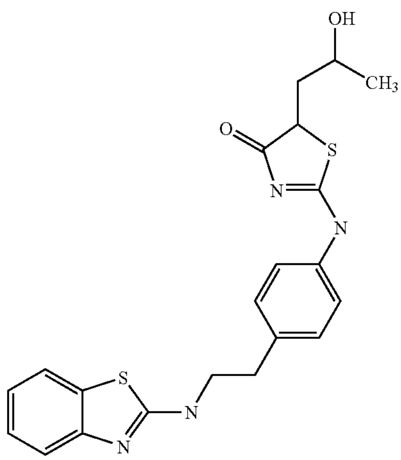 | C | 426 | 427.1 |
| 441 | 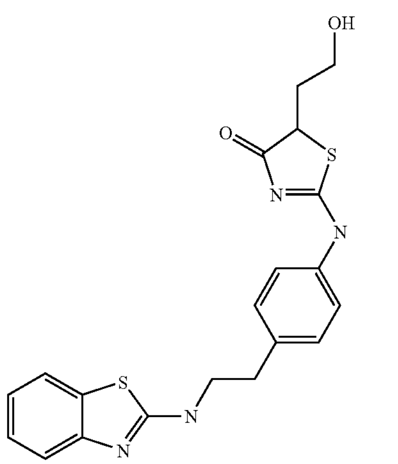 | C | 412 | 413.1 |
| 442 | 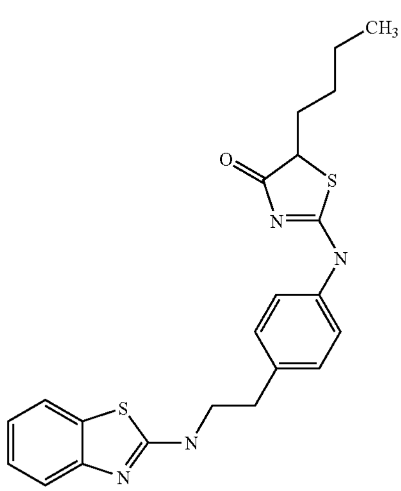 | C | 424 | 425.1 |

-continued

| Ex. No. | Structure | Ki | Exact Mass (g/mol) | Observed Mass (M + 1) |
|---|---|---|---|---|
| 443 | 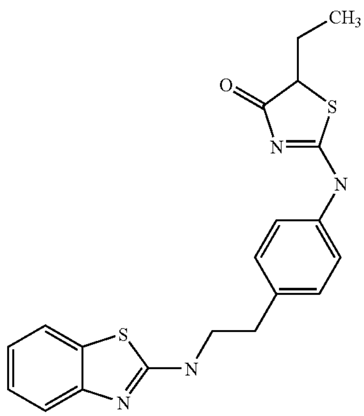 | C | 396 | 397.1 |
| 444 | 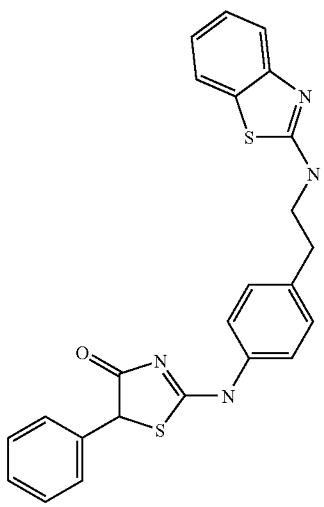 | C | 444 | 445.11 |
| 445 | 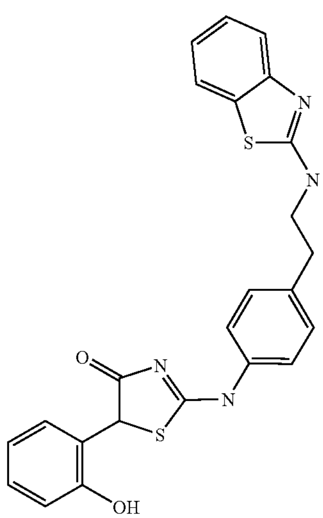 | C | 460 | 461.11 |

-continued
| Ex. No. | Structure | Ki | Exact Mass (g/mol) | Observed Mass (M + 1) |
|---|---|---|---|---|
| 446 | 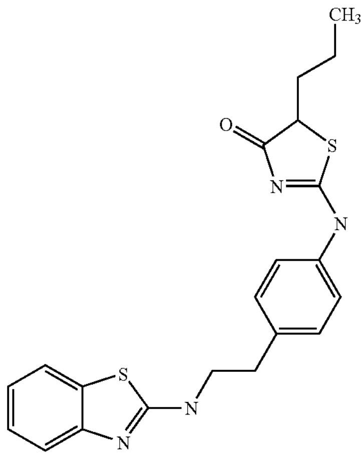 | C | 410 | 411.1 |
| 447 | 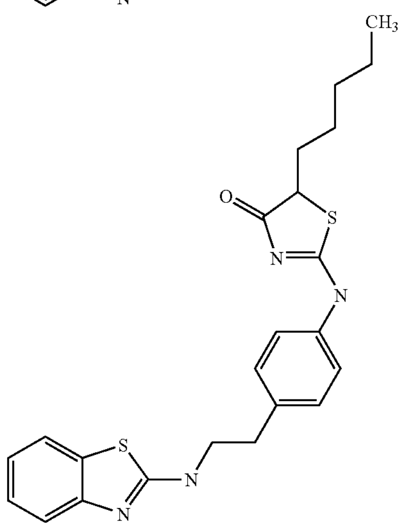 | C | 438 | 439.11 |
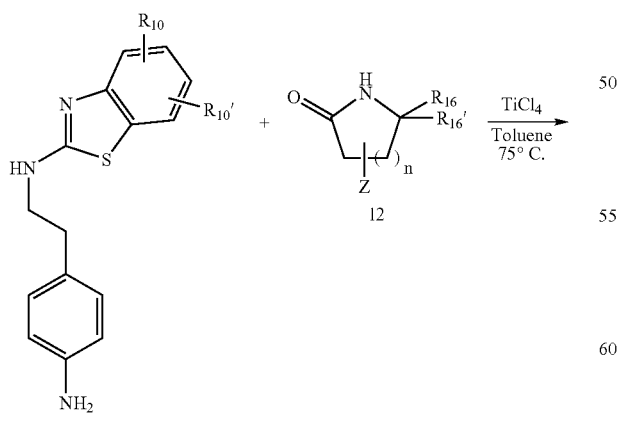
Procedure 1
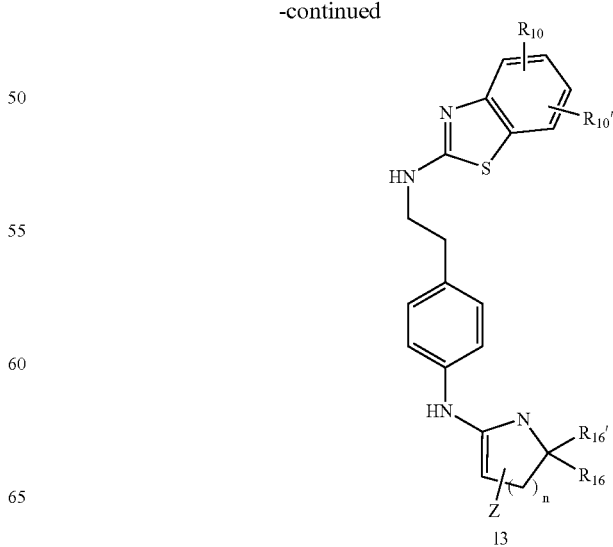
-continued Procedure I, Step 1:

A mixture of I1 ($R_{10}$ is H and $R_{10'}$ is H) (1 eq) and I2 ($R_{16}$ is phenyl, $R_{16'}$ is H, Z is H, and n is 3) (1 eq) was heated at 75° C. in toluene for 10 minutes. A 1 N solution of titanium tetrachloride in toluene (2 eq) was added drop wise to the mixture. Four hours later the TLC showed no product, as a result 6 eq of diisopropylethylamine was added and the mixture was heated at 75° C. overnight. The solution was diluted with ethyl acetate and a 1:1 mixture of $H_2O$ to a saturated $NaHCO_3$ solution. A solid precipitated. The suspension was filtered through celite and the filtrate was washed with a 1:1 mixture of $H_2O$ to a saturated $NaHCO_3$ solution (2×), and brine. The solution was dried over anhydrous $NaSO_4$, and concentrated to afford I3 ($R_{10}$ is H, $R_{10'}$ is H, $R_{16}$ is phenyl, $R_{16'}$ is H, Z is H, and n is 3).

The following compounds were-prepared using analogous methods:

compound of interest at 37° C. After 20 minutes the 1 mM IBMX-HH assay buffer (±antagonist compound) was removed and replaced with assay buffer containing 1.5 μM (CHO cells) or 5 μM (HEK-293 cells) forskolin (Sigma #F-6886) and various concentrations of NPY in the presence or absence of one concentration of the antagonist compound of interest. At the end of 10 minutes, the media were removed and the cell monolayers treated with 75 μl ethanol. The tissue culture plates were agitated on a platform shaker for 15 minutes, after which the plates were transferred to a warm bath in order to evaporate the ethanol. Upon bringing all wells to dryness, the cell residues were resolubilized with 250 μl FlashPlate® assay buffer. The amount of cAMP in each well was quantified using the [$^{125}$I]-cAMP FlashPlate® kit (NEN #SMP-001) and according to the protocol provided by the manufacturer. Data were expressed as either pmol cAMP/ml or as percent of control. All data points were determined in

| Example No. | Structure | | Exact Mass (g/mol) | Onserved Mass (M + 1) |
|---|---|---|---|---|
| 448 | 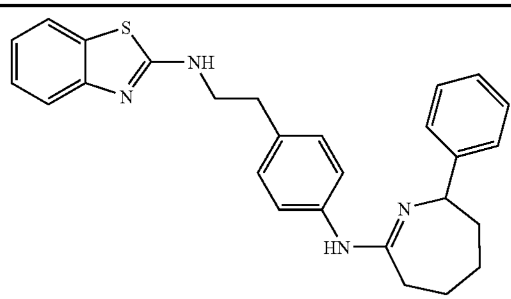 | B | 440 | 441.1 |
| 449 | | B | 426 | 427.1 | cAMP Assay

HEK-293 cells expressing the Y1 receptor subtype were maintained in Dulbecco's modified Eagles' media (Gico-BRL) supplemented with 10% FCS (ICN), 1% penicillin-streptomycin and 200 μg/ml Geneticin® (GibcoBRL #11811-031) under a humidified 5% $CO_2$ atmosphere. Two days prior to assay, cells were released from T-175 tissue culture flasks using cell dissociation solution (1×; non-enzymatic [Sigma #C-5914]) and seeded into 96-well, flat-bottom tissue culture plates at a density of 15,000 to 20,000 cells per well. After approximately 48 hours, the cell monolayers were rinsed with Hank's balanced salt solution (HBSS) then pre-incubated with approximately 150 μl/well of assay buffer (HBSS supplemented with 4 mM $MgCl_2$, 10 mM HEPES, 0.2% BSA [HH]) containing 1 mM 3-isobutyl-1-methylxanthine ([IBMX] Sigma #I-587) with or without the antagonist triplicate and $EC_{50}$'s (nM) were calculated using a nonlinear (sigmoidal) regression equation (GraphPad Prism™). The $K_B$ of the antagonist compound was estimated using the following formula:

$$K_B=[B]/(1-\{[A']/[A]\})$$

where

[A] is the $EC_{50}$ of the agonist (NPY) in the absence of antagonist;

[A'] is the $EC_{50}$ of the agonist (NPY) in the presence of antagonist; and

[B] is the concentration of the antagonist.

NPY Receptor Binding Assay

Human NPY Y1 receptors were expressed in CHO cells. Binding assays were performed in 50 mM HEPES, pH 7.2, 2.5 mM CaCl$_2$, 1 mM MgCl$_2$ and 0.1% BSA containing 5-10 µg of membrane protein and 0.1 nM $^{125}$L-peptide YY in a total volume of 200 µl. Non-specific binding was determined in the presence of 1 µM NPY. The reaction mixtures were incubated for 90 minutes at room temperature then filtered through Millipore MAFC glass fiber filter plates which had been pre-soaked in 0.5% polyethleneimine. The filters were washed with phosphate-buffered saline, and radioactivity was measured in a Packard TopCount scintillation counter.

If applicable, the Ki values for compounds shown in the tables below are rated, "A" for Ki values less than 1000 nanomolar (nM), "B" for Ki values greater than and including 1000 nM to and including 10,000 nM and "C" for Ki values greater than 10,000 nM.

What is claimed is:

1. A compound represented by the structural Formula 1:

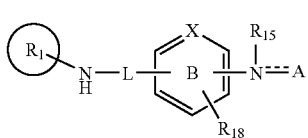

Formula 1 or a pharmaceutically acceptable salt thereof, wherein:

R$_1$ is N-arylaminocarbonyl, N-heteroarylaminocarbonyl, benzimidazolyl benzothiazolyl, or the moieties:

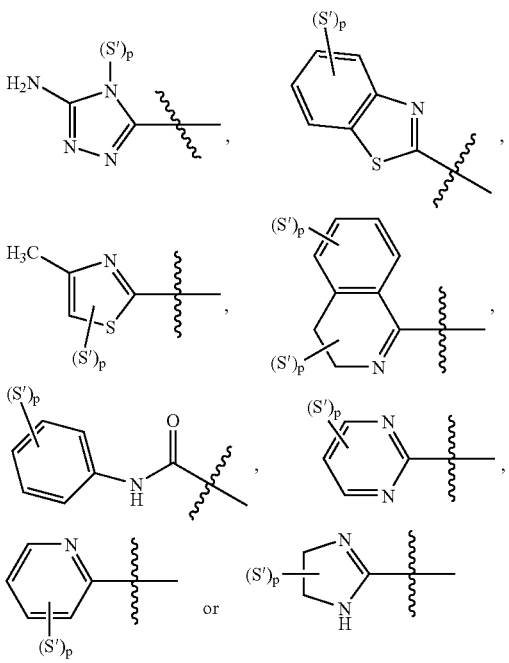

wherein the benzimidazolyl and benzothiazolyl are each optionally independently unsubstituted or substituted with 1 to 5 substituents and each substituent is independently selected from the group consisting of: halogen, alkyl, cycloalkyl, alkoxy, alkylsultonyl, thiol, alkoxyalkyl, cycloalkylalkyl, heterocycloalkyl, heterocycloalkylakyl, arylalkyl, heteroarylalkyl, aryl, heteroaryl, —OR$_{20}$, —CN, —NO$_2$, —NR$_{20}$R$_{21}$, —C(O)R$_{20}$, —C(O)OR$_{20}$, —C(O)NR$_{20}$R$_{21}$, —S(O)$_{0-2}$NR$_{20}$R$_{21}$, —CF$_3$, —OCF$_3$, —CF$_2$CF$_3$, —C(=N—OR$_{20}$)R$_{21}$, —N(R$_{20}$)S(O)$_{0-2}$R$_{21}$, —N(R$_{20}$)C(O)(R$_{21}$), —N(R$_{20}$)C(O)NR$_{21}$R$_{22}$, —C(O)N(R$_{20}$)(R$_{21}$), —SO$_2$R$_{20}$ and —SO$_2$N(R$_{20}$)(R$_{21}$);

R$_{20}$, R$_{21}$ and R$_{22}$ are independently alkyl, cycloalkyl, heterocycloalkyl, cycloalkylaikyl, hetercycloalkylalkyl, arylalkyl, heteroarylalkyl, aryl or heteroaryl, wherein each alkyl, cycloalkyl, cycloalkylalkyl, hetercycloalkylalkyl, arylalkyl, heteroarylalkyl, aryl and heteroaryl are unsubstituted or optionally independently substituted with 1-5 substituents which are the same or different and are independently selected from the group consisting of: halogen, —CF$_3$, —CN, —COOH, —C(O)Oalkyl, —C(O)Ocycloalkyl, —C(O)O-arylalkyl, —C(O)O-heteroarylalkyl, —C(O)NH$_2$, —C(O)N(H)(alkyl), —C(O)N(H)(arylalkyl), —C(O)N(H)(heteroarylalkyl), —C(O)N(H)(cycloalkyl), —C(O)N(H)(aryl), —C(O)N(H)(heteroaryl), —C(O)N(H)(arylalkyl), —C(O)N(H)(heteroarylalkyl), —C(O)N(alkyl)(alkyl), —C(O)N(alkyl)(aryl), —C(O)N(alkyl)(heteroaryl), —S-alkyl, —S-aryl, —S-arylalkyl, —S-heteroarylalkyl, —S(O)$_2$(alkyl), —S(O)$_2$(aryl), —S(O)$_2$(arylalkyl), —S(O)$_2$(heteroaryl), —S(O)$_2$(heteroarylalkyl), —S(O)$_2$(cycloalkyl), —S(O)$_2$N(H)(heterocycloalkyl), —S(O)NH$_2$, —S(O)N(alkyl)(alkyl), —S(O)N(H)(alkyl), —S(O)N(H)(aryl), —S(O)N(alkyl)(alkyl), —S(O)$_2$NH$_2$, —S(O)$_2$N(H)(alkyl), —S(O)$_2$N(H)(aryl), —S(O)$_2$N(H)(arylalkyl), —S(O)$_2$N(H)(heteroarylalkyl), —S(O)$_2$N(H)(cycloalkyl), —S(O)$_2$N(alkyl)(aryl), —S(O)$_2$N(alkyl)(alkyl), OH, —O(C$_1$-C$_6$)alkyl, —O-cycloalkyl, —O-heterocycloalkyl, —O-Cycloalkylalkyl, —O-heterocycloalkylalkyl, —O-arylalkyl, —O-heteroarylalkyl, —O-Aryl, —O-heteroaryl, —NH$_2$, —N(H)(alkyl), —N(H)(aryl), —N(H)(heteroaryl), —N(H)arylalkyl, —N(H)(heteroarylalkyl), —N(alkyl)(alkyl), —N(arylalkyl)(arylalkyl), —N(heteroarylalkyl)(arylalkyl), —N(H)C(O)-alkyl, —N(H)C(O)-arylalkyl, —N(H)C(O)-heteroarylalkyl, —N(H)C(O)—heteroaryl, —N(H)C(O)-aryl, —N(H)C(O)NH$_2$, —N(H)C(O)N(H)(alkyl), —N(H)C(O)N(alkyl)(alkyl), —N(alkyl)C(O)N(H)(alkyl), —N(alkyl)C(O)N(alkyl)(alkyl), —N(H)S(O)$_2$-alkyl, —N(H)S(O)$_2$-arylalkyl, —N(H)S(O)$_2$-heteroarylalkyl, —N(H)S(O)$_2$-aryl, —N(H)S(O)$_2$-heteroaryl, —N(H)S(O)$_2$N(H)(alkyl), —N(H)S(O)$_2$N(alkyl)(alkyl), —N(alkyl)S(O)$_2$N(H)(alkyl) and —N(alkyl)S(O)$_2$N(alkyl)(alkyl);

X is —CH or N;

L is an alkyl or heteroalkyl linker chain optionally independently linked with one or more selected from the group consisting of: alkyl, aryl, cycloalkyl, spiroalkyl, heteroaryl and combinations thereof;

R$_{15}$ is present or absent and if present is H, aryl, alkyl, arylalkyl, heterocycloalkyl or heteroarylalkyl;

R$_{18}$ is H, halogen, alkyl, cycloalkyl, cycloalkylalkyl, heterocycloalkyl, heterocycloalkylalkyl, arylalkyl, heteroarylalkyl, aryl, heteroaryl, —OR$_{20}$, —CN, —NO$_2$, —NR$_{20}$R$_{21}$, —C(O)R$_{20}$, —C(O)OR$_{20}$, —C(O)NR$_{20}$R$_{21}$, —S(O)$_{0-2}$NR$_{20}$R$_{21}$, —CF$_3$, —OCF$_3$, —CF$_2$CF$_3$, —C(=N—OR$_{20}$)R$_{21}$, —N(R$_{20}$)S(O)$_{0-2}$R$_{21}$, —N(R$_{20}$)C(O)(R$_{21}$), —N(R$_{20}$)C(O)NR$_{21}$R$_{22}$, —C(O)N(R$_{20}$)(R$_{21}$), —SO$_2$R$_{20}$ or SO$_2$N(R$_{20}$)(R$_{21}$);

A is represented by the structural Formula 2:

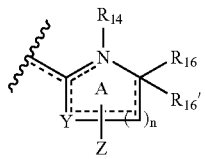

Formula 2

$R_{14}$ is present or absent and if present is H, aryl, alkyl, arylalkyl, carboxyl, alkylaryl, acyl, alkenyl, heteroarylalkyl, alkoxycarbonyl, heteroaryl, cyoloalkyl, alkenyl or aryloarbonyl;

or $R_{16}$ and $R_{16'}$ are independently present or absent, are the same or different and are independently selected from the group consisting of: H, aryl, alkyl, arylalkyl, heteroaryl, carboxyl, aroyl, heteroarylalkyl, cyclohexanyl, cycloalkyl, alkylthio, alkoxycarbonyl, cycloalkylalkyl, alkylaminocarbonyl, haloaryl, haloalkyl, phenylalkyl, alkoxy, acyl, aroyl, alkylcarboxyl, alkylcycloalkyl, alkylamino, adamantyl, alkylthioether, biphenyl, alkanol, dialkylisocyanate and alkylimidiazole, with the proviso that at least one of $R_{16}$ and $R_{16'}$ is present;

or $R_{16}$ and $R_{16'}$ taken together forms =O;

Y is S;

Z is either present or absent and if present is H, aryl, alkyl, alkoxy, arylalkyl, phenylalkyl, cycloalkyl, spiroalkyl, alkylaryl, alkylaminocarbonyl, haloaryl, haloalkyl, $(CH_3)_2NC(O)$—, alkylcarboxyl, acyl, heteroarylalkyl, alkoxycarbonyl, carboxyl, alkylcycloalkyl, alkylamino, alkylthioether, biphenyl, alkanol, dialkylisocyanate, alkylimidiazole or =O;

B is a six membered ring;

and n is 2;

with the proviso that when condition (ii) is satisfied, then at least one of $R_{16}$, $R_{16'}$, $R_{18}$ and Z is present and is a substituent other than H;

condition (ii) is satisfied when the compound of Formula 1 is

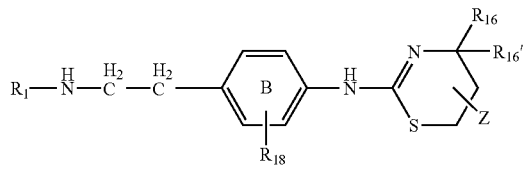

and

S' is independently selected from the group consisting of: H, alkyl, halogen, methoxy, carboxyaminomethyl, alkoxy, oxo and alkanoylaminomethyl.

2. The compound of claim 1, wherein $R_{14}$ is present or absent and if present is selected from the group consisting of: H,

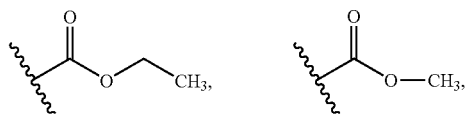

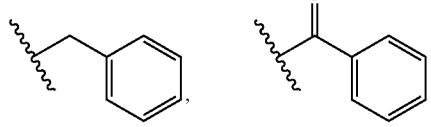

3. The compound of claim 1, wherein $R_{14}$ is H.

4. The compound of claim 1, wherein, $R_{15}$ is H.

5. The compound of claim 1, wherein $R_{16}$ and $R_{16'}$ are selected from the group consisting of H,

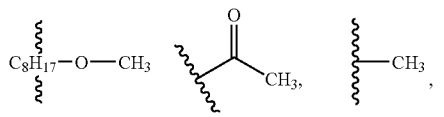

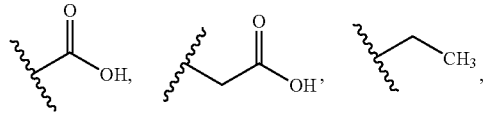

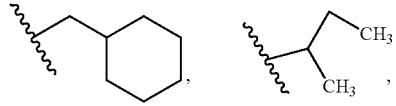

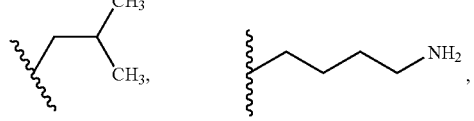

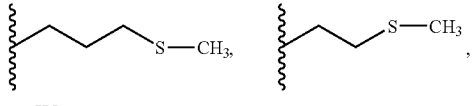

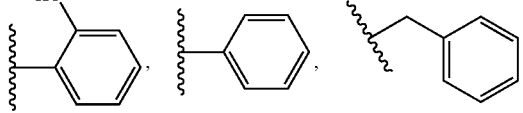

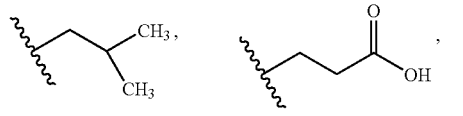

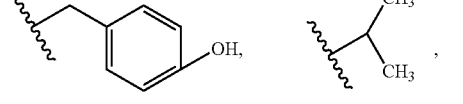

-continued
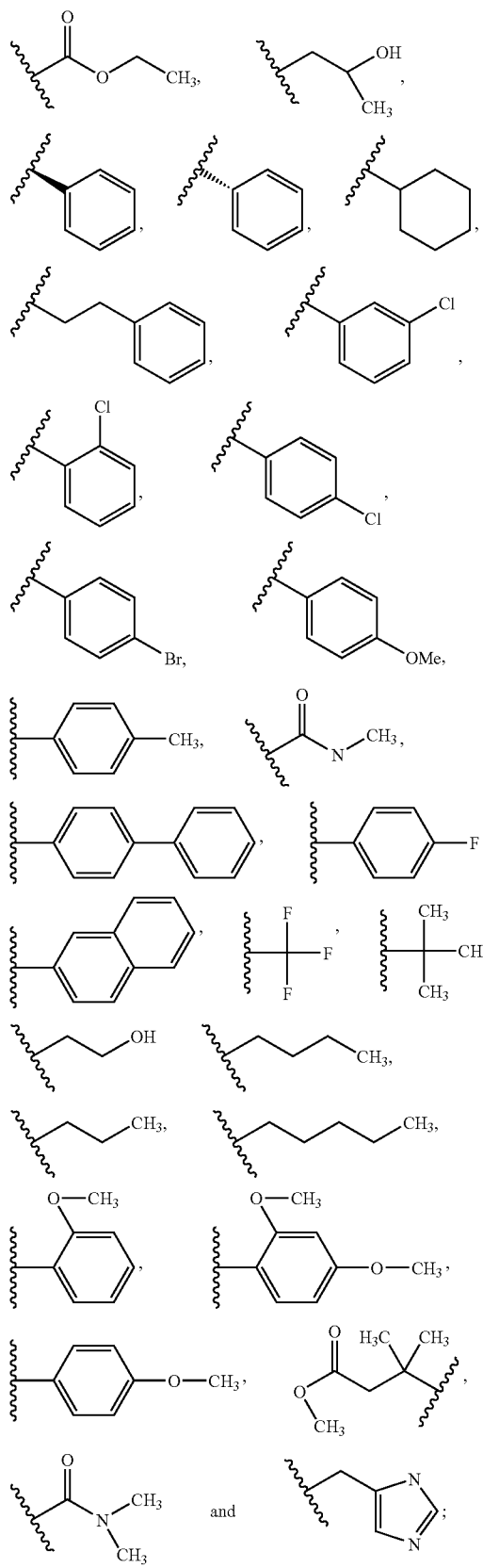
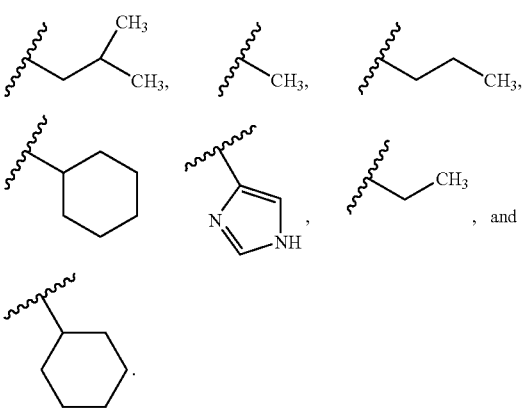
or
$R_{16}$ and $R_{16'}$ taken together is
6. The compound of claim 5, wherein $R_{16}$ and $R_{16'}$ are selected from the group consisting of:
7. The compound of claim 1, wherein Z is present or absent and if present is selected from the group consisting of: H,
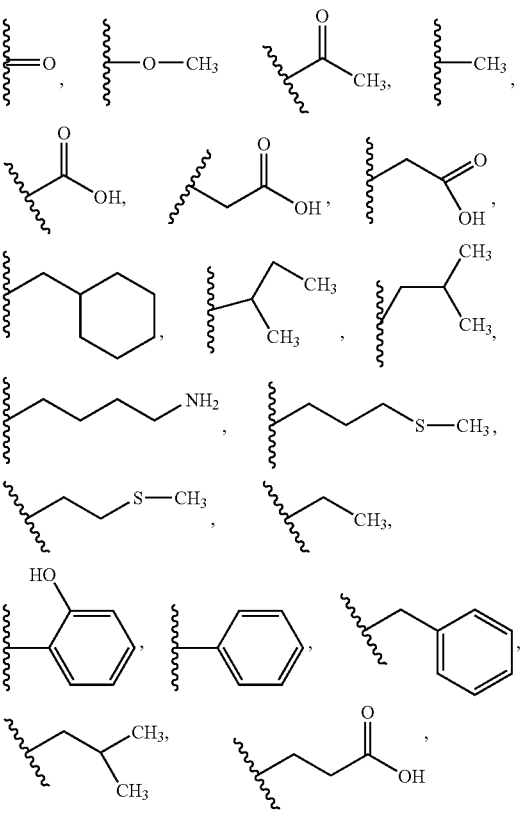

-continued

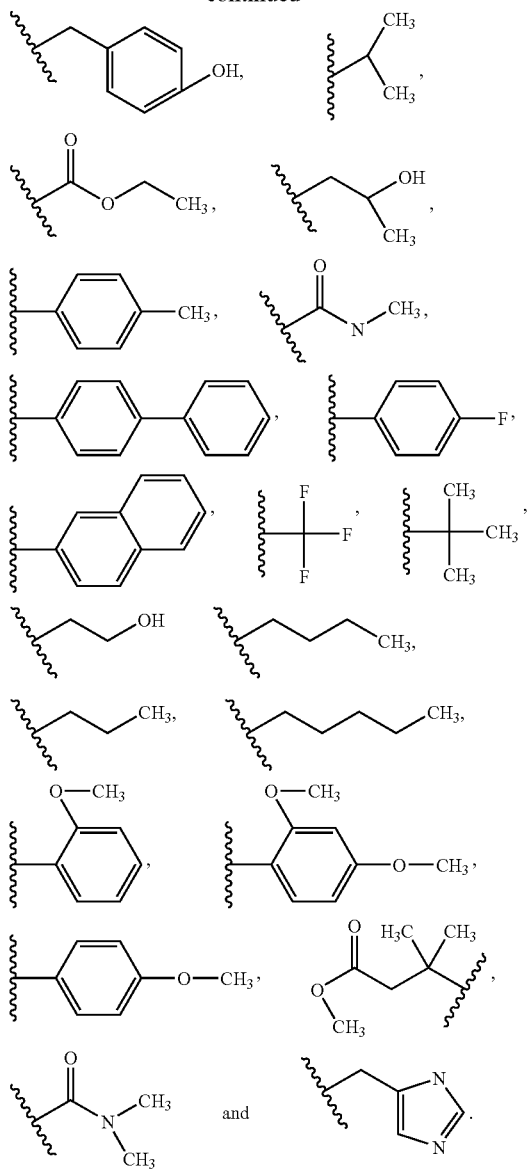

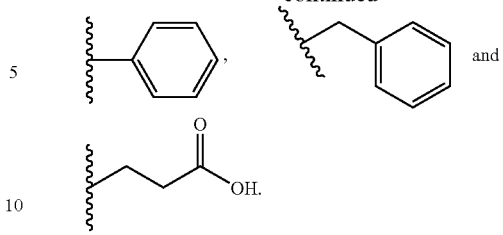

8. The compound of claim 7, wherein Z is selected from the group consisting of: H,

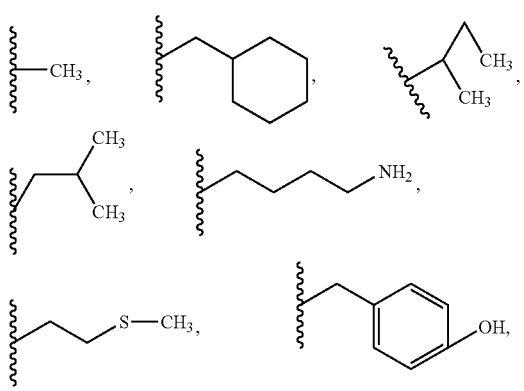

9. The compound of claim 1, wherein L is alkyl.

10. The compound of claim 1, wherein L is —CH$_2$CH$_2$—.

11. The compound of claim 1, wherein X is —CH.

12. The compound of claim 1, wherein R$_{18}$ is H.

13. The compound of claim 1 represented by the structural Formula 3:

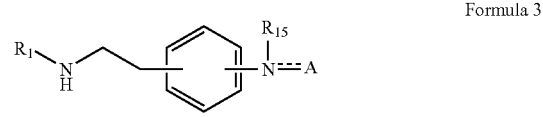

Formula 3 wherein R$_1$, R$_{15}$ and A are herein defined.

14. The compound of claim 1 represented by structural Formula 4:

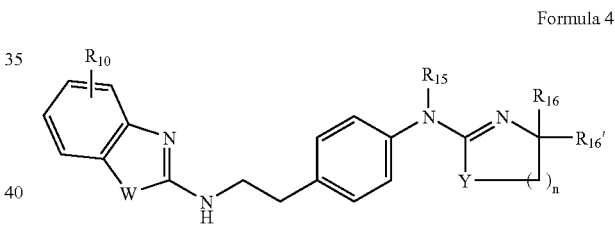

Formula 4 wherein R$_{10}$ is selected from the group consisting of: H, halogen, alkyl, aryl, arylalkyl, heteroaryl, heteroarylalkyl, alkoxyalkyl, hydroxy, nitro, cyano, thiol, alkylcarbonyl, alkylsulfonyl and alkoxy; and W is S or N with the proviso that when W is N, N is substituted with H, alkyl, arylalkyl, heteroarylalkyl, aryl or heteroaryl.

15. The compound of claim 14 represented by structural Formula 5:

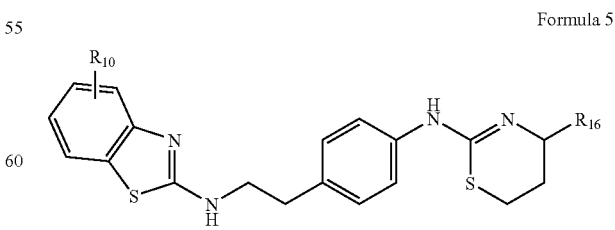

Formula 5 wherein R$_{10}$ and R$_{16}$ are herein defined.

16. The compound of claim 15, wherein R$^{16}$ is selected from the group consisting of: CH$_3$,

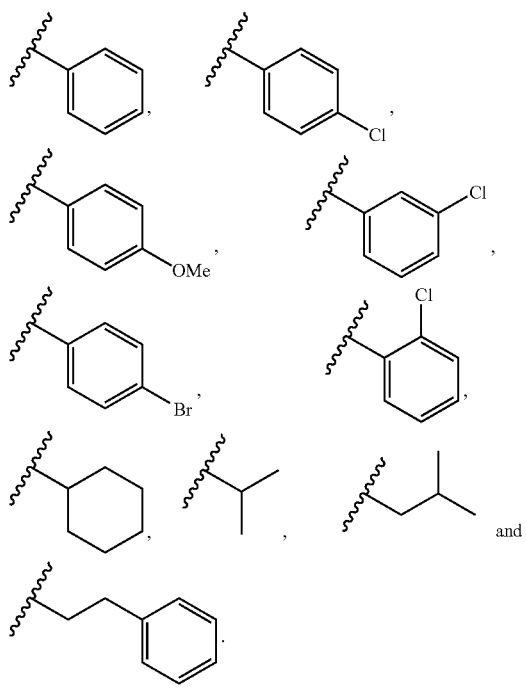

17. The compound of claim 1, wherein $R_1$ is

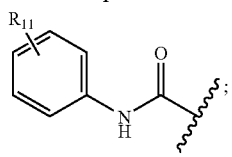

and $R_{11}$ is selected from the group consisting of: H, halogen, alkyl, aryl, aralkyl, heteroaryl, heteroarylalkyl, alkoxyalkyl, hydroxy, nitro, cyano, thiol and alkylcarbonyl.

18. The compound of claim 1 represented by structural Formula 7:

Formula 7

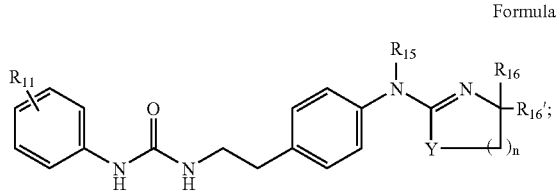

and $R_{11}$ is selected from the group consisting of: H, halogen, alkyl, aryl, aralkyl, heteroaryl, heteroarylalkyl, alkoxyalkyl, hydroxy, nitro, cyano, thiol and alkylcarbonyl.

19. The compound of claim 1, wherein $R_1$ is

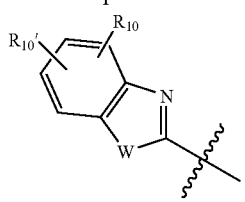

$R_{10}$ and $R_{10'}$ are the same or different and are independently selected from the group consisting of: H, halogen, alkyl, aryl, arylalkyl, heteroaryl, heteroarylalkyl, alkoxyalkyl, hydroxy, nitro, cyano, thiol, alkylcarbonyl, alkylsulfonyl and alkoxy;

and

W is S, or N and when W is N, N is unsubstituted or substituted with alkyl, arylalkyl, heteroarylalkyl, aryl or heteroaryl.

20. The compound of claim 19, wherein W is S.

21. The compound of claim 19, wherein $R_{10}$ is selected from the group consisting of: H

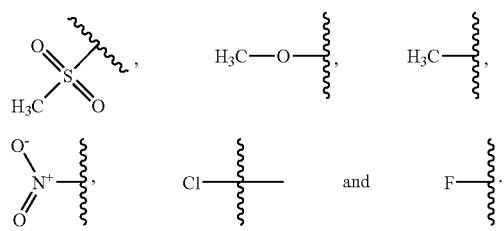

22. The compound of claim 19, wherein $R_{10'}$ is H or Cl.

23. The compound of claim 1, represented by structural Formula 8:

Formula 8

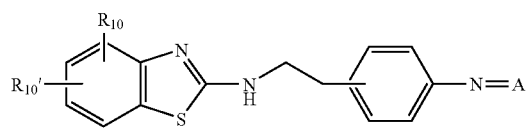

wherein:

$R_{10}$ is H, —OCH$_3$, —CH$_3$, Cl or F;

$R_{10'}$ is H or Cl;

and

A is selected from the following structures:

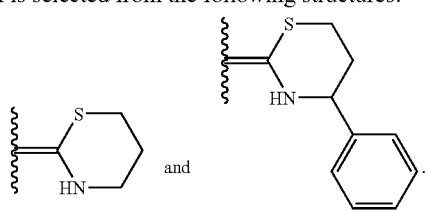

24. The compound of claim 1, represented by the structural Formulas 9, 10 and 11 below:

Formula 9

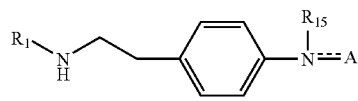

Formula 10

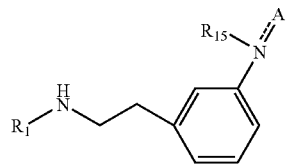

-continued

Formula 11

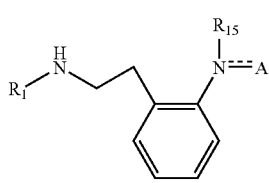

25. The compound of claim 1, with the proviso that when condition (iv) is satisfied, then at least one of $R_{16}$, $R_{16'}$, $R_{18}$, and Z is present and is a substituent other than H;
condition (iv) is satisfied when the compound of Formula 1 is

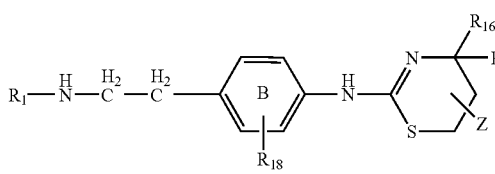

wherein

S' is independently selected from the group consisting of: H, halogen, alkyl, cycloalkyl, cycloalkylalkyl, alkoxy, thiol, alkylsulfonyl, alkoxyalkyl, heterocycloalkyl, heterocycloalkylalkyl, arylalkyl, heteroarylalkyl, aryl, heteroaryl, —$OR_{20}$, —CN, —$NO_2$, —$NR_{20}R_{21}$, —$C(O)R_{20}$, —$C(O)OR_{20}$, —$C(O)NR_{20}R_{21}$, —$S(O)_{0-2}NR_{20}R_{21}$, —$CF_3$, —$OCF_3$, —$CF_2CF_3$, —$C(=N—OR_{20})R_{21}$, —$N(R_{20})S(O)_{0-2}R_{21}$, —$N(R_{20})C(O)(R_{21})$, —$N(R_{20})C(O)NR_{21}R_{22}$, —$C(O)N(R_{20})(R_{21})$, —$SO_2R_{20}$ and —$SO_2N(R_{20})(R_{21})$.

26. A compound represented by the structural Formulas 12, 13, 14, 15, and 16.

Formula 12

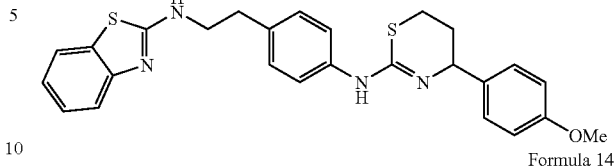

Formula 13

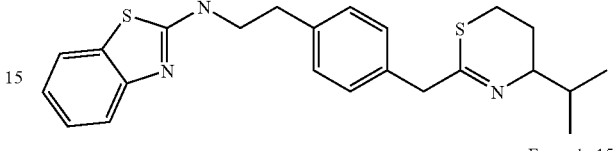

Formula 14

Formula 15

Formula 16

27. A pharmaceutical composition comprising a therapeutically effective amount of at least one compound according to claim 1 in combination with at least one pharmaceutically acceptable carrier.

28. A pharmaceutical composition comprising a therapeutically effective amount of at least one compound according to claim 25 in combination with at least one pharmaceutically acceptable carrier.

29. A process for making a pharmaceutical composition comprising combining at least one compound according to claim 25, and at least one pharmaceutically acceptable carrier.

* * * * *

UNITED STATES PATENT AND TRADEMARK OFFICE
CERTIFICATE OF CORRECTION

PATENT NO. : 7,459,450 B2  Page 1 of 3
APPLICATION NO. : 11/117584
DATED : December 2, 2008
INVENTOR(S) : Zhaoning Zhu et al.

It is certified that error appears in the above-identified patent and that said Letters Patent is hereby corrected as shown below:

In the Claims:

Claim 1, col. 336, line 5:   Please correct "cycioalkyl" to --cycloalkyl--.

Claim 1, col. 336, line 6:   Please correct "cycloalkylaikyl" to --cycloalkylalkyl--.

Claim 1, col. 336, line 6:   Please correct "hetercycloalkyl" to --heterocycloalkyl--.

Claim 5, col. 338, lines 32-34:   Please change

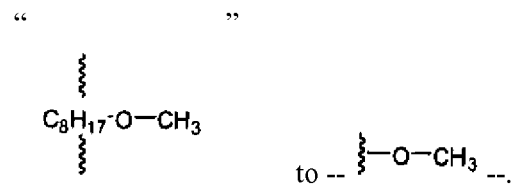

Claim 6, col. 340, lines 20-24:   Please correct

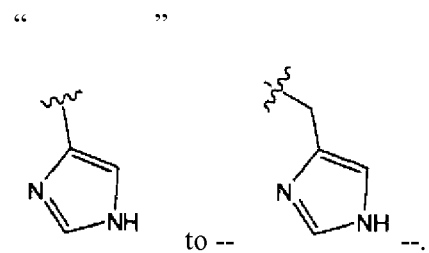

Claim 6, col. 340, lines 25-30:   Please correct

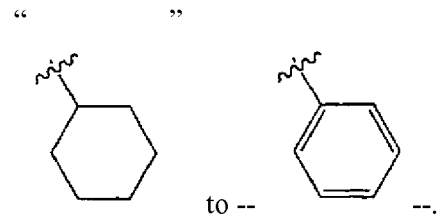

UNITED STATES PATENT AND TRADEMARK OFFICE
CERTIFICATE OF CORRECTION

PATENT NO.        : 7,459,450 B2
APPLICATION NO.   : 11/117584
DATED             : December 2, 2008
INVENTOR(S)       : Zhaoning Zhu et al.

It is certified that error appears in the above-identified patent and that said Letters Patent is hereby corrected as shown below:

Claim 7, col. 340, line 38:    Please add --,-- between  and .

Claim 19, col. 343, lines 59-65:    Please correct

"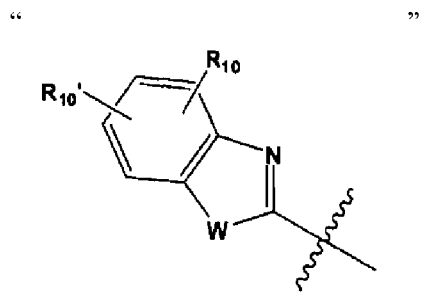"

to

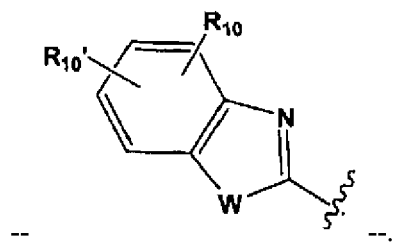

--    --.

UNITED STATES PATENT AND TRADEMARK OFFICE
CERTIFICATE OF CORRECTION

PATENT NO.        : 7,459,450 B2
APPLICATION NO.   : 11/117584
DATED             : December 2, 2008
INVENTOR(S)       : Zhaoning Zhu et al.

It is certified that error appears in the above-identified patent and that said Letters Patent is hereby corrected as shown below:

<u>Claim 19, col. 343, lines 59-65</u>: Please correct

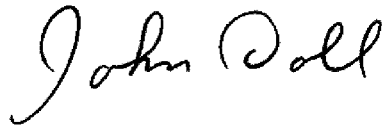

Signed and Sealed this

Twenty-fourth Day of March, 2009

JOHN DOLL
*Acting Director of the United States Patent and Trademark Office*